United States Patent
Ray, II

(10) Patent No.: US 10,813,908 B2
(45) Date of Patent: *Oct. 27, 2020

(54) COMPOSITIONS AND METHODS FOR TREATING AN INFECTION

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/167,047

(22) Filed: Oct. 22, 2018

(65) Prior Publication Data

US 2019/0054061 A1 Feb. 21, 2019

Related U.S. Application Data

(63) Continuation of application No. 15/597,936, filed on May 17, 2017, now Pat. No. 10,105,342, which is a continuation-in-part of application No. 15/440,800, filed on Feb. 23, 2017, and a continuation-in-part of application No. 14/975,172, filed on Dec. 18, 2015, now Pat. No. 9,707,229, and a continuation-in-part of application No. 14/819,342, filed on Aug. 5, 2015.

(60) Provisional application No. 62/298,994, filed on Feb. 23, 2016, provisional application No. 62/298,991, filed on Feb. 23, 2016.

(51) Int. Cl.
| | |
|---|---|
| *A61K 31/351* | (2006.01) |
| *A61K 9/00* | (2006.01) |
| *A61K 9/06* | (2006.01) |
| *A61K 31/506* | (2006.01) |
| *A61K 31/7048* | (2006.01) |
| *A61K 31/65* | (2006.01) |
| *A61K 31/7036* | (2006.01) |
| *A61K 38/12* | (2006.01) |
| *A61K 45/06* | (2006.01) |
| *A61K 9/08* | (2006.01) |
| *A61K 31/496* | (2006.01) |
| *A61K 31/431* | (2006.01) |

(52) U.S. Cl.
CPC .......... *A61K 31/351* (2013.01); *A61K 9/0014* (2013.01); *A61K 9/06* (2013.01); *A61K 9/08* (2013.01); *A61K 31/431* (2013.01); *A61K 31/496* (2013.01); *A61K 31/506* (2013.01); *A61K 31/65* (2013.01); *A61K 31/7036* (2013.01); *A61K 31/7048* (2013.01); *A61K 38/12* (2013.01); *A61K 45/06* (2013.01)

(58) Field of Classification Search
CPC ...... A61K 31/351; A61K 38/12; A61K 45/06; A61K 9/08; A61K 9/0014; A61K 9/06; A61K 31/506; A61K 31/7048; A61K 31/65; A61K 31/7036
See application file for complete search history.

(56) References Cited

U.S. PATENT DOCUMENTS

| | | | |
|---|---|---|---|
| 2009/0016990 A1* | 1/2009 | Alberte | A61K 31/185 424/85.5 |
| 2014/0256826 A1* | 9/2014 | Lemire | A61K 47/10 514/703 |

* cited by examiner

*Primary Examiner* — Sahar Javanmard
(74) *Attorney, Agent, or Firm* — Akerman LLP

(57) ABSTRACT

The present application relates to compounded compositions, methods of making compounded compositions, and methods of using compounded compositions. For example, disclosed herein are compounded compositions and methods of making compounded compositions comprising one or more anti-infective agents such as mupirocin.

17 Claims, No Drawings

COMPOSITIONS AND METHODS FOR TREATING AN INFECTION

CROSS-REFERENCE TO RELATED APPLICATIONS

The present application is a continuation application of U.S. patent application Ser. No. 15/597,936, filed 17 May 2017, which is a continuation-in-part application of U.S. patent application Ser. No. 15/440,800, filed 23 Feb. 2017, and also a continuation-in-part application of U.S. patent application Ser. No. 14/975,172, filed 18 Dec. 2015, now U.S. Pat. No. 9,707,229 and also a continuation-in-part application of U.S. patent application Ser. No. 14/819,342, filed Aug. 5, 2015, each of which is incorporated by reference in its entirety. U.S. patent application Ser. No. 15/440,800 claims priority to U.S. Provisional Patent Application No. 62/298,991, filed 23 Feb. 2016, and to U.S. Provisional Patent Application No. 62/298,994, filed 23 Feb. 2016, each of which is incorporated by reference in its entirety.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Despite advances in the understanding of the pathology of bacterial infections and fungal infections, there is still a need for compositions and methods that efficiently treat or prevent the progression and reoccurrence of bacterial infections and fungal infections that affect the skin, the respiratory system, or the feet.

SUMMARY

In one aspect, a method of making a compounded composition includes combining anti-infective powder and mupirocin ointment, and mixing the combined powder and ointment to form a homogeneous compounded composition. For example the compounded composition may include mupirocin and an anti-infective selected from doxycycline, streptomycin, polymyxin B, piperacillin/tazobactam, colistimethate, bacitracin, amphotericin B, voriconazole, tobramycin, ketoconazole, or combination thereof. Mupirocin may be a mupirocin ointment. One or more of the anti-infectives may comprise an anti-infective powder comprising crushed tablets or anti-infective for injection powder. In various embodiments, the compounded composition comprises anti-infective for injection in an amount from about 1% to about 20% w/w. In an aspect, the anti-infective for injection comprises one or more of bacitracin for injection, colistimethate sodium for injection, pentasodium colistin methanesulfonate for injection, piperacillin-tazobactam for injection, polymyxin B for injection USP, streptomycin sulfate for injection, tobramycin sulfate for injection, voriconazole for injection, or amphotericin B for injection. In one example, the anti-infective powder may comprise one or more crushed doxycycline hyclate tablets and the mupirocin ointment may comprise mupirocin 2% ointment. In a further aspect, the method may include generating the doxycycline powder comprising crushing one or more doxycycline hyclate tablets.

In various embodiments, the compounded composition may comprise about 1.7% w/w mupirocin and about 2% w/w doxycycline. In various aspects, the anti-infective powder further includes a ketoconazole powder. The ketoconazole powder may include ketoconazole or a pharmaceutically acceptable salt thereof, and the compounded composition may comprise from about 0.5% to about 5.0% w/w ketoconazole. The ketoconazole powder may comprise a ground ketoconazole tablet powder. In one aspect, the method may include (a) crushing one or more doxycycline hyclate tablets to generate doxycycline hyclate tablet powder, (b) crushing one or more ketoconazole tablets to generate ketoconazole tablet powder, or (c) both (a) and (b). In one example, the compounded composition may include about 1.7% w/w mupirocin, about 2% w/w doxycycline, and about 2.5% w/w ketoconazole. In one aspect, the anti-infective powder may further include a streptomycin powder comprising streptomycin or a pharmaceutically acceptable salt thereof, and the compounded homogeneous composition may comprise from about 0.5% to about 5.0% w/w streptomycin. The streptomycin powder may comprise streptomycin sulfate for injection USP powder. The compounded homogeneous composition may comprise about 1.7% w/w mupirocin, about 2% w/w doxycycline, about 2.5% w/w ketoconazole, and about 4% w/w streptomycin.

In another aspect, a compounded composition comprises an ointment including mupirocin ointment, such as mupirocin 2% ointment, in an amount at least 60% w/w and crushed doxycycline hyclate tablet. The homogeneous compounded composition may comprise from about 0.5% to about 1.8% w/w mupirocin and from about 0.5% to about 6.0% w/w doxycycline. In an aspect, the compounded composition comprises a homogeneous compounded ointment comprising mupirocin 2% ointment and an anti-infective for injection. The mupirocin 2% ointment may be present in an amount at least 60% w/w of the compounded ointment and the anti-infective for injection may be present in an amount from about 1% to about 20% w/w of the compounded ointment. The anti-infective for injection may comprise one or more of bacitracin for injection, colistimethate sodium for injection, pentasodium colistin methanesulfonate for injection, piperacillin-tazobactam for injection, polymyxin B for injection USP, streptomycin sulfate for injection, tobramycin sulfate for injection, voriconazole for injection, or amphotericin B for injection.

In various embodiments, the compounded ointment may further include crushed doxycycline hyclate 100 mg tablet in an amount from about 2% to about 10% w/w of the compounded ointment. The compounded ointment may further include crushed ketoconazole 200 mg tablet in an amount from 1% to 9% w/w of the compounded ointment. In an embodiment, the compounded ointment comprises about 2% doxycycline w/w and about 2.5% w/w ketoconazole w/w. In an embodiment, the anti-infective for injection comprises streptomycin sulfate for injection. In one example, the compounded ointment may include about 2% w/w doxycycline, about 2.5% w/w ketoconazole, about 4% w/w streptomycin, and about 1.71% w/w mupirocin.

In some aspects, the compounded composition may comprise from about 60% to about 98% w/w mupirocin 2% ointment and from about 2% to about 14% w/w crushed doxycycline hyclate 100 mg tablet. The compounded composition may further include crushed ketoconazole tablet in an amount such that the compounded composition comprises from about 0.5% to about 5.0% w/w ketoconazole. The compounded composition may include from about 70% to about 97% w/w mupirocin 2% ointment, from about 2% to 14% w/w crushed doxycycline hyclate 100 mg tablet, and from about 1% to about 9% w/w crushed ketoconazole 200 mg tablet.

In various aspects, the compounded composition comprises a compounded ointment that may be directly applied to infected skin.

In some aspects, the compounded composition may comprise a footbath composition for addition to an aqueous diluent for administration to infected skin within a footbath. In various aspects, a compounded composition for a footbath includes mupirocin and an anti-infective. In one embodiment, the compounded ointment may comprise a footbath composition for addition to an aqueous diluent. In one aspect, the anti-infective may be selected from doxycycline, streptomycin, polymyxin B, piperacillin/tazobactam, colistimethate, bacitracin, amphotericin B, voriconazole, tobramycin, ketoconazole, or combination thereof. Mupirocin may be a 2% mupirocin ointment. One or more of the anti-infectives may comprise an anti-infective powder comprising crushed oral tablet or anti-infective for injection. Components of the compounded composition may be mixed with the diluent separately or with all or a portion of one or more other components of the compounded composition.

In an aspect, a method of treating or preventing one or both of a bacterial infection or fungal infection of a foot of a subject includes combining (i) an antibacterial agent comprising mupirocin, (ii) at least one of an additional antibacterial or an antifungal agent, and (iii) an aqueous diluent to form a footbath. The method may further include contacting a skin area of a foot of a subject that is infected or suspected to be infected with the footbath solution.

In various embodiments, the mupirocin comprises a mupirocin ointment, which may be a mupirocin 2% ointment. Combining may comprise adding a compounded composition comprising the antibacterial agent comprising mupirocin and the at least one of an additional antibacterial or an antifungal agent to the aqueous diluent. In one example, at least one of an additional antibacterial or an antifungal agent comprises at least one antibacterial or pharmaceutically acceptable salt thereof selected from doxycycline, bacitracin, colistimethate, piperacillin-tazobactam, polymyxin B, tobramycin, or streptomycin. In one example, the antibacterial or pharmaceutically acceptable salt thereof may comprise one or more of bacitracin for injection, colistimethate sodium for injection, pentasodium colistin methanesulfonate for injection, piperacillin-tazobactam for injection, polymyxin B for injection USP, or streptomycin sulfate for injection, or tobramycin sulfate for injection. The at least one of an additional antibacterial or an antifungal agent may include at least one antifungal or pharmaceutically acceptable salt thereof selected from voriconazole or amphotericin B. In one example, at least one antifungal or pharmaceutically acceptable salt thereof may comprise one or more of voriconazole for injection or amphotericin B for injection. In one embodiment, the at least one of an additional antibacterial or an antifungal agent comprises one or more of doxycycline, bacitracin, colistimethate, piperacillin-tazobactam, polymyxin B, streptomycin, voriconazole, tobramycin, amphotericin B, or pharmaceutically acceptable salt thereof. The at least one of an additional antibacterial or an antifungal agent may comprise one or more of bacitracin for injection, colistimethate sodium for injection, pentasodium colistin methanesulfonate for injection, piperacillin-tazobactam for injection, polymyxin B for injection, streptomycin sulfate for injection, tobramycin sulfate for injection, voriconazole for injection, or amphotericin B for injection. In one embodiment, the at least one of an additional antibacterial or an antifungal agent comprises doxycycline, streptomycin, and ketoconazole. In one example, combining comprises adding to the doxycycline, streptomycin, and ketoconazole to the diluent, wherein the doxycycline, streptomycin, and ketoconazole comprise crushed doxycycline hyclate tablet, crushed ketoconazole tablet, and streptomycin sulfate for injection. In one embodiment, the method comprises further combining (iv) an excipient base powder comprising micronized xylitol, poloxamers, or a blend of micronized xylitol and poloxamers. In some embodiments, the aqueous diluent may include sodium hypochlorite or Dakin's solution.

In one aspect, a method of making a homogeneous compounded ointment includes combining mupirocin 2% ointment in an amount at least 60% w/w of the compounded ointment and an anti-infective for injection in an amount from about 1% to about 20% w/w of the compounded ointment. The anti-infective for injection may comprise one or more of bacitracin for injection, colistimethate sodium for injection, pentasodium colistin methanesulfonate for injection, piperacillin-tazobactam for injection, polymyxin B for injection, streptomycin sulfate for injection, voriconazole for injection, tobramycin sulfate for injection, or amphotericin B for injection.

In various embodiments of the method, the anti-infective for injection may include voriconazole for injection. In one example, combining may comprise combining mupirocin 2% ointment in an amount about 86% w/w of the compounded ointment and voriconazole for injection in an amount about 0.8% w/w of the compounded ointment. The anti-infective for injection may further comprise streptomycin sulfate for injection. In one example, combining comprises combining mupirocin 2% ointment in an amount about 80% w/w of the compounded ointment, voriconazole for injection in an amount about 0.8% w/w of the compounded ointment, and streptomycin sulfate for injection in an amount about 5.528% w/w of the compounded ointment. The method may include combining crushed doxycycline hyclate tablet powder. In one example, combining comprises combining mupirocin 2% ointment in an amount about 77.6% w/w of the compounded ointment, voriconazole for injection in an amount about 0.8% w/w of the compounded ointment, and streptomycin sulfate for injection in an amount about 5.528% w/w of the compounded ointment, and a sufficient amount of crushed doxycycline hyclate tablet powder to obtain about 1% w/w doxycycline in the compounded ointment. In some embodiments, the anti-infective for injection comprises tobramycin for injection and the method further comprises combining crushed doxycycline hyclate tablet powder. In one example, combining comprises combining mupirocin 2% ointment in an amount about 81.3% w/w of the compounded ointment, voriconazole for injection in an amount about 0.8% w/w of the compounded ointment, tobramycin sulfate for injection in an amount about 1.8% w/w of the compounded ointment, and a sufficient amount of crushed doxycycline hyclate tablet powder to obtain about 1% w/w doxycycline in the compounded ointment.

In some embodiments of the method, the anti-infective for injection comprises streptomycin sulfate for injection and the method further comprises combining crushed doxycycline hyclate tablet powder and crushed ketoconazole tablet powder. In one example of the method, combining comprises combining mupirocin 2% ointment in an amount about 85.7% w/w of the compounded ointment, streptomycin sulfate for injection in an amount about 5.528% w/w of the compounded ointment, a sufficient amount of crushed doxycycline hyclate tablet powder to obtain about 2% w/w doxycycline in the compounded ointment, and a sufficient amount of crushed ketoconazole tablet powder to obtain about 2.5% w/w ketoconazole in the compounded ointment.

In another aspect, a homogeneous compounded ointment includes mupirocin 2% ointment in an amount at least 60% w/w, and an anti-infective for injection in an amount from about 1% to about 20% w/w. The anti-infective for injection may comprise one or more of bacitracin for injection, colistimethate sodium for injection, pentasodium colistin methanesulfonate for injection, piperacillin-tazobactam for injection, polymyxin B for injection, streptomycin sulfate for injection, voriconazole for injection, tobramycin sulfate for injection, or amphotericin B for injection.

In various embodiments, the anti-infective for injection comprises voriconazole for injection and the compounded ointment comprises about 86% w/w mupirocin 2% ointment and about 0.8% w/w voriconazole for injection. In another embodiment, the anti-infective for injection comprises voriconazole for injection and streptomycin sulfate for injection and the compounded ointment comprises about 80% w/w mupirocin 2% ointment, about 0.8% w/w voriconazole for injection, and about 5.528% w/w streptomycin sulfate for injection. In another embodiment, the anti-infective for injection comprises voriconazole for injection and streptomycin sulfate for injection and the compounded ointment further comprises about 1% w/w doxycycline. In one example, the compounded ointment comprises about 77.6% w/w mupirocin 2% ointment, about 0.8% w/w voriconazole for injection, about 5.528% w/w streptomycin sulfate for injection, and about 2.435% w/w doxycycline hyclate 100 mg tablet. In another embodiment, the anti-infective for injection comprises voriconazole for injection and tobramycin sulfate for injection and the compounded ointment further comprises about 1% w/w doxycycline. In one example, the compounded ointment comprises about 81.3% w/w mupirocin 2% ointment, about 0.8% w/w voriconazole for injection, about 1.8% w/w tobramycin sulfate for injection, and about 2.435% w/w doxycycline hyclate 100 mg tablet. In one embodiment, the anti-infective for injection comprises streptomycin sulfate for injection and the compounded ointment further comprises about 2% doxycycline and about 2.5% ketoconazole. In one example, the compounded ointment comprises about 85.7% w/w mupirocin 2% ointment, about 5.528% w/w streptomycin sulfate for injection, about 4.87% w/w doxycycline hyclate 100 mg tablet, and about 3.875% ketoconazole 200 mg tablet.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. In an aspect, a disclosed method can optionally comprise one or more additional steps, such as, for example, repeating an administering step or altering an administering step.

As used herein, the term "subject" refers to the target of administration, e.g., a human being. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and child subjects, as well as fetuses, whether male or female, are intended to be covered. In an aspect, a subject can be a human patient. In an aspect, the subject can have diabetes, can be obese, can be immunocompromised, can be non-ambulatory, or can have poor blood flow, or a combination thereof. In an aspect, the subject can routinely wear thick socks or wear heavy boots. In an aspect, the subject can have been diagnosed with or can be suspected of having (i) cancer that affects at least a part of the respiratory tract, (ii) emphysema, (iii) pneumonia, (iv) bronchitis, (v) tuberculosis, (vi) asthma, or (vii) a combination thereof.

A subject can have a bacterial infection, be suspected of having a bacterial infection, or be at risk of developing a bacterial infection. A subject can have a fungal infection, be suspected of having a fungal infection, or be at risk of developing a fungal infection. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have a chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have a chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

A "patient" refers to a subject afflicted with one or more infections. In an aspect, a patient can refer to a subject that has been diagnosed with or is suspected of having a bacterial infection. In an aspect, a bacterial infection or suspected bacterial infection can affect at least a portion of one or both feet of the subject, the subject's skin, the subject's respiratory system, or another appendage, such as at least a portion of one or both of the subject's hands. In an aspect, a patient can refer to a subject that has been diagnosed with or is suspected of having a fungal infection. In an aspect, a fungal infection or suspected fungal infection can affect at least a portion of one or both feet of the subject, the subject's skin, the subject's respiratory system, or another appendage, such as at least a portion of one or both of the subject's hands.

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

In an aspect, "treating" means eradicating a bacterial infection, a fungal infection, a suspected bacterial infection, a suspected fungal infection, or a combination thereof. In an aspect, treating means reducing the effects of a bacterial infection or a fungal infection or symptoms of a bacterial infection or a fungal infection. For example, treating an infection can reduce the severity of an established infection in a subject by 1%-100% as compared to a control. In an aspect, treating can refer to a 1%, 2%, 3%, 4%, 5%, 6%, 7%, 8%, 9%, 10%, 20%, 30%, 40%, 50%, 60%, 70%, 80%, 90%, or 100% reduction in the severity of an established bacterial infection or an established fungal infection. For example, treating an infection can reduce one or more symptoms of an infection in a subject by 1%-100% as compared to a control. In an aspect, treating can refer to 1%, 2%, 3%, 4%, 5%, 6%, 7%, 8%, 9%, 10%, 20%, 30%, 40%, 50%, 60%, 70%, 80%, 90%, 100% reduction of one or more symptoms of an established bacterial infection or an established fungal infection. It is understood that treatment does not necessarily refer to a cure or complete ablation or eradication of the bacterial infection, the fungal infection, or both. However, in an aspect, treatment can refer to a cure or complete ablation or eradication of the bacterial infection, the fungal infection, or both.

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed. In an aspect, preventing a bacterial infection, fungal infection, or both is intended.

As used herein, the term "diagnosed" means having been subjected to a physical examination by a person of skill, for example, a physician, and found to have a condition that can be diagnosed or treated by the disclosed compounded composition or the disclosed methods. For example, "diagnosed with a bacterial infection" means having been subjected to a physical examination by a person of skill, for example, a physician, and found to have a condition that can be treated by a disclosed compounded composition or a disclosed method. For example, "suspected of having a bacterial infection" can mean having been subjected to a physical examination by a person of skill, for example, a physician, and found to have a condition that can likely be treated by a disclosed compounded composition or a disclosed method. For example, "diagnosed with a fungal infection" means having been subjected to a physical examination by a person of skill, for example, a physician, and found to have a condition that can likely be treated by a disclosed compounded composition or a disclosed method. For example, "suspected of having a fungal infection" can mean having been subjected to a physical examination by a person of skill, for example, a physician, and found to have a condition that can be likely be treated by a disclosed compounded composition or a disclosed method.

As used herein, the terms "administering" and "administration" refer to any method of providing a disclosed compounded composition or a pharmaceutical preparation comprising a disclosed compounded composition to a subject. Such methods are well known to those skilled in the art and include, but are not limited to: oral administration, transdermal administration, administration by inhalation, nasal administration, topical administration, intravaginal administration, ophthalmic administration, intra-aural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed compounded composition, or anti-infective agent can be administered therapeutically; that is, administered to treat an existing disease or condition. In further various aspects, a disclosed compounded composition or a pharmaceutical preparation comprising a disclosed compounded composition can be administered prophylactically; that is, administered for prevention of a disease or condition. In an aspect, the skilled person can determine an efficacious dose, an efficacious schedule, and an efficacious route of administration for a disclosed compounded composition or a disclosed pharmaceutical preparation comprising a disclosed compounded composition so as to treat or prevent an infection. In an aspect, the skilled person can also alter, change, or modify an aspect of an administering step so as to improve efficacy of a disclosed compounded composition or a disclosed pharmaceutical preparation comprising a disclosed compounded composition. In an aspect, administering means contacting at least a portion of one foot or both feet of a subject with agitated water comprising a disclosed compounded composition or a disclosed pharmaceutical preparation comprising a disclosed compounded composition. In an aspect, administering means contacting at least a portion of the subject's skin with disclosed compounded composition or a disclosed pharmaceutical preparation comprising a disclosed compounded composition. In an aspect, administering means contacting at least a portion of the subject's respiratory system with a disclosed compounded composition or a disclosed pharmaceutical preparation comprising a disclosed compounded composition. In an aspect, administering means contacting at least a portion of one foot or both feet of a subject with agitated water comprising a solution or suspension comprising a disclosed compounded composition. In an aspect, administering means contacting at least a portion of the subject's skin with a solution or suspension comprising a disclosed compounded composition. In an aspect, administering means contacting at least a portion of the subject's respiratory system with a solution or suspension comprising a disclosed compounded composition.

As used herein, a "footbath" refers to a container that can hold some volume (e.g., about 1.0 liters to about 10 liters) of an aqueous solution or suspension (e.g., water) and is designed to physically accommodate at least a portion of one or both feet of a subject. Footbaths are known to the skilled person. A footbath can comprise several features or agents that effect various functions. For example, a footbath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or feet of the subject, a massage agent (e.g., a roller) that provides massaging contact to at least a portion of one or both feet, a pedicure agent that can clean or contact a foot or feet with a pumice, or a combination thereof. In an aspect, a footbath can have a water fall element. In an aspect, an agitation agent or an agitator can be coupled to both a motor and the footbath. Motors and agitators are known to the art. In an aspect, a footbath can comprise one or more splash guards and other spill-resistant features to ensure that the water remains enclosed within a container. A footbath may also accommodate a subject's calves, meaning that the container is "deep" so as to allow the enclosed water to contact both the feet and at least a portion of the calves of the subject. Several manufacturers market footbaths including PIBB, Dr. Scholl's, Kendal, Conair (e.g., Model FB5X, FB3, FB27R, FB30, FB52, etc.), and Brookstone.

As used herein, a "mixing container" can be a container that can accommodate one more liquids (such as a diluent, for example) and one or more disclosed compounded compositions or disclosed anti-infective agents. A mixing container can have a lid or a cover, which facilitates the mixing of any liquid with any solid that has been added to the container. A mixing container can be used to generate a solution or suspension. In an aspect, a mixing container can contain about 2 ounces to about 30 ounces. In an aspect, a mixing container can contain about 6 ounces. In an aspect, a mixing container can contain about 16 ounces. The art is familiar with mixing containers and mixing containers are commercially available.

As used herein, "modifying the method" can comprise modifying or changing one or more features or aspects of one or more steps of a disclosed method. For example, in an aspect, a method can be altered by changing the amount of a disclosed compounded composition applied to a subject's skin, or by changing the frequency of the subject's use of the compounded composition, or by changing the duration of time that the subject uses the compounded composition, or a combination thereof. In an aspect, a method can be altered by changing the amount of a disclosed compounded composition added to a footbath, by changing the frequency of the subject's use of the footbath, or by changing the duration of time that the subject's foot or feet contact the water contained within the footbath, or a combination thereof. The same modifications can be applied to a method comprising intranasally administering a disclosed compounded composition or a disclosed pharmaceutical preparation comprising a disclosed compounded composition to the subject's nares or topically administering a disclosed compounded composition or a disclosed pharmaceutical preparation comprising a disclosed compounded composition to the subject's skin.

The term "contacting" as used herein refers to bringing at least one disclosed compounded compositions or a disclosed pharmaceutical preparation comprising a disclosed compounded composition together with a target area or intended target area in such a manner that the disclosed compounded composition or the disclosed pharmaceutical preparation comprising a disclosed compounded composition can exert an effect on the intended target or targeted area either directly or indirectly. A target or intended target area can be at least a portion of one or both feet of a subject or at least portion of the subject's skin or an area diagnosed with, suspected of having a bacterial infection or a fungal infection, or susceptible to developing a bacterial infection or a fungal infection. In an aspect, "contacting" means to insert or immerse at least a portion of one or both feet of a subject into the water contained within a footbath. In an aspect, "contacting" means topically applying a disclosed compounded composition to the skin of a subject or intranasally administering a disclosed compounded composition to the nares of a subject.

The term "mixing" as used in a disclosed method means to physically combine the recited components so as to achieve a homogeneous compounded composition (which, for example, can be a dry powder formulation or an ointment). In an aspect, the recited components can be shaken, or stirred, or agitated so as to achieve a homogeneous compounded composition. In an aspect, "mixing" can also include sifting the homogeneous compounded composition though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogeneous compounded composition. In an aspect, mixing a powder and an ointment may include combining one or more powders and the ointment. One or more of the powders or portions thereof may be wetted prior to addition to the ointment. Thus, in an aspect, adding, combining, or mixing a powder and an ointment may include adding, combining, or mixing wetted powder and the ointment.

In an aspect, "mixing" can be used to describe the process of making a solution or suspension by adding one or more disclosed compounded compositions to a diluent. For example, mixing means to physically combine a disclosed compounded composition with a diluent to make a solution or a suspension. Such mixing can occur in a disclosed mixing container.

As used herein, "ointment" refers to a homogeneous, viscous preparation that can be applied to a subject. In aspect, the term "ointment" can be considered synonymous to a lotion, a cream, an emulsion, a gel, an emollient, etc. In an aspect, an ointment comprises a disclosed compounded composition. An ointment can be applied in a variety of ways, included, for example, but not limited to, direct topical application to the subject's skin or contact with skin in an enclosed environment, such as a footbath.

As used herein, LoxaSperse™ refers to an excipient base powder comprising a blend of micronized xylitol and poloxamers. Such base compositions are known to those skilled in the art. LoxaSperse™ is manufactured by PCCA (Houston, Tex.) and is used as a chemical dispersing or solubilizing agent, thereby improving the solubility and dispersibility of poorly water soluble active pharmaceutical ingredients (APIs) or agents. LoxaSperse™ can be obtained from a bulk source.

As used herein, XyliFos™ refers to an excipient base powder comprising xylitol, poloxamer 407, hydroxylpropyl betadex, and epigallocatechin gallate. XyliFos™ is manufactured by PCCA (Houston, Tex.) and is used as a chemical dispersing or solubilizing agent, thereby improving the solubility and dispersibility of poorly water soluble active pharmaceutical ingredients (APIs) or agents. XyliFos™ can be obtained from a bulk source.

In an aspect, xylitol can comprise an ointment or can comprise a dry powder. In an aspect, xylitol can be xylitol NF (20-80 MESH).

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, or suspensions, which may include dispersions, colloids, or emulsions, as well as sterile powders for reconstitution into sterile injectable solutions, suspensions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, "determining" can refer to measuring or ascertaining the presence and severity of an infection, such as, for example, a bacterial infection or a fungal infection that affects a subject's skin, a subject's respiratory system, or affects one or more of a subject's appendages (e.g., at least a portion of one or both feet). Methods and techniques used to determining the presence and/or severity of an infection are typically known to the medical arts. For example, the art is familiar with the ways to identify and/or diagnose the presence, severity, or both of a bacterial infection, a fungal infection, or both.

As used herein, "effective amount" and "amount effective" can refer to an amount that is sufficient to achieve the desired result such as, for example, the treatment and/or prevention of a bacterial infection or a suspected bacterial infection or a fungal infection or a suspected fungal infection. As used herein, the terms "effective amount" and "amount effective" can refer to an amount that is sufficient to achieve the desired an effect on an undesired condition (e.g., a bacterial or a fungal infection). For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific compounded composition employed; the age, body weight, general health, sex and diet of the patient; the time of administration; the route of administration; the rate of excretion of the specific compounded composition employed; the duration of the treatment; drugs used in combination or coincidental with the specific compounded composition employed and like factors well known in the medical arts. For example, it is well within the skill of the art to start doses of a compounded composition at levels lower than those required to achieve the desired therapeutic effect and to gradually increase the dosage until the desired effect is achieved. If desired, then the effective daily dose can be divided into multiple doses for purposes of administration. Consequently, single dose compounded compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition, such as, for example, a bacterial infection or a fungal infection.

Disclosed are the components to be used to prepare a disclosed compounded compositions as well as the disclosed compounded compositions to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Anti-Infective Agents

As used herein, an anti-infective agent can be an antibacterial agent, an antifungal agent, a combination of antibacterial agents, a combination of antifungal agents, or a combination of antibacterial agents and antifungal agents.

Antibacterial agents are known to the art. For example, the art generally recognizes several categories of antibacterial agents including (1) enicillins, (2) cephalosporins, (3) fluoroquinolones, (4) aminoglycosides, (5) monobactams, (6) carbapenems, (7) macrolides, and (8) other agents. For example, as used herein, an antibacterial agent can comprise afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, and moxifloxacin.

Antifungal agents may include (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents. For example, as used herein, an antifungal agent can comprise abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, and voriconazole.

In an aspect, an antifungal agent or antibacterial agent can comprise an ointment or can comprise a dry powder. In an aspect, the dry powder can be obtained from crushed tablets comprising an antifungal agent or from a container comprising the antifungal agent as a dry powder. In an aspect, an antifungal agent can be pure or substantially pure and can be obtained from a bulk source. In an aspect, an antifungal agent can be commercially available as, for example, a tablet, a cream, an ointment, or a powder.

Azithromycin is a semi-synthetic macrolide antibiotic structurally related to erythromycin. In an aspect, the azithromycin can comprise an ointment or can comprise a dry powder. In an aspect, the dry powder can be obtained from crushed tablets comprising azithromycin or from a container comprising azithromycin as a dry powder. The azithromycin can be pure or substantially pure and can be obtained from a bulk source. In an aspect, azithromycin can be azithromycin powder for injection USP. In an aspect, azithromycin can be commercially available, for example, as a vial comprising 500 mg.

Ciprofloxacin is a synthetic broad spectrum fluoroquinolone antibiotic that binds and inhibits DNA gyrase. In an aspect, ciprofloxacin can comprise an ointment or can comprise a dry powder. In an aspect, the dry powder can be obtained from crushed tablets comprising ciprofloxacin or from a container comprising ciprofloxacin as a dry powder. In an aspect, ciprofloxacin can be pure or substantially pure and can be obtained from a bulk source. In an aspect, ciprofloxacin can be commercially available.

Ciprofloxacin hydrochloride is the hydrochloride salt form of ciprofloxacin. The molecular formula for ciprofloxacin hydrochloride is $C_{17}H_{21}CkFN_3O_4$. In an aspect, ciprofloxacin hydrochloride can comprise an ointment or can comprise a dry powder. In an aspect, the dry powder can be obtained from crushed tablets comprising ciprofloxacin hydrochloride or from a container comprising ciprofloxacin hydrochloride as a dry powder. In an aspect, ciprofloxacin hydrochloride can be pure or substantially pure and can be obtained from a bulk source. In an aspect, ciprofloxacin hydrochloride can be commercially available. In an aspect, ciprofloxacin hydrochloride can be ciprofloxacin HCl monohydrate USP. In an aspect, about 291.1 mg of ciprofloxacin HCl is approximately equivalent to about 250.0 mg of pure or substantially pure ciprofloxacin.

Clindamycin is a semisynthetic broad spectrum antibiotic produced by chemical modification of the parent compound lincomycin. In an aspect, clindamycin can comprise an ointment or can comprise a dry powder. In an aspect, the dry powder can be obtained from crushed tablets comprising clindamycin or from a container comprising clindamycin as a dry powder. In an aspect, clindamycin can be pure or substantially pure and can be obtained from a bulk source. In an aspect, clindamycin can be commercially available.

Clindamycin hydrochloride is the hydrochloride salt form of clindamycin. In an aspect, clindamycin hydrochloride can comprise an ointment or can comprise a dry powder. In an aspect, the dry powder can be obtained from crushed tablets comprising clindamycin hydrochloride or from a container comprising clindamycin hydrochloride as a dry powder. In an aspect, clindamycin hydrochloride can be pure or substantially pure and can be obtained from a bulk source. In an aspect, clindamycin hydrochloride can be commercially available. In an aspect, clindamycin hydrochloride can be clindamycin hydrochloride USP 83.22. In an aspect, about 1.13 g of clindamycin HCl is approximately equivalent to 1.0 g of pure or substantially pure clindamycin.

Clindamycin phosphate is the phosphate salt form of clindamycin. In an aspect, clindamycin phosphate can comprise an ointment or can comprise a dry powder. In an aspect, the dry powder can be obtained from crushed tablets comprising clindamycin phosphate or from a container comprising clindamycin phosphate as a dry powder. In an aspect, clindamycin phosphate can be pure or substantially pure and can be obtained from a bulk source. In an aspect, clindamycin can be commercially available, as for example, a clindamycin phosphate 1.0% gel.

Clobetasol propionate is the propionate salt form of clobetasol, which is a topical synthetic corticosteroid. In an aspect, clobetasol propionate can comprise an ointment or can comprise a dry powder. In an aspect, the dry powder can be obtained from crushed tablets comprising clobetasol propionate or from a container comprising clobetasol propionate as a dry powder. In an aspect, clobetasol propionate can be pure or substantially pure and can be obtained from a bulk source. In an aspect, clobetasol propionate can be commercially available as, for example, a clobetasol propionate 0.05% ointment.

Doxycycline is a synthetic tetracycline derivative. In an aspect, doxycycline can comprise an ointment or can comprise a dry powder. In an aspect, the dry powder can be obtained from crushed tablets comprising doxycycline, e.g., a doxycycline salt such as doxycycline hyclate or doxycycline monohydrate. Doxycycline powder may also be obtained from capsules containing doxycycline, e.g., doxycycline salts, or a container comprising doxycycline as a dry powder. In an aspect, doxycycline can be pure or substantially pure and can be obtained from a bulk source. In an aspect, doxycycline can be commercially available.

Doxycycline hyclate is a salt form of doxycycline. In an aspect, doxycycline hyclate can comprise an ointment or can comprise a dry powder. In an aspect, the dry powder can be obtained from crushed tablets comprising doxycycline hyclate or from a container comprising doxycycline hyclate as a dry powder. In an aspect, doxycycline hyclate can be pure or substantially pure and can be obtained from a bulk source. In an aspect, doxycycline hyclate can be commercially available, for example, as 50 mg, 75 mg, 100 mg, and 150 mg In an aspect, about 131.75 mg of a crushed doxycycline hyclate 100 mg tablet is approximately equivalent to about 50 mg pure or substantially pure doxycycline. Various example formulations described herein may be described with respect to 100 mg tablets of doxycycline hyclate; however, it will be appreciated that in various aspects other strength tablets may be substituted by using equivalent amounts of doxycycline in such other strength tablets. Amounts of other components may similarly be adjusted as necessary.

Doxycycline monohydrate is another salt form of doxycycline. Doxycycline monohydrate can comprise an ointment or can comprise a dry powder. In an aspect, the dry powder can be obtained from crushed tablets comprising doxycycline monohydrate or from a container comprising doxycycline monohydrate as a dry powder. In an aspect, doxycycline monohydrate can be pure or substantially pure and can be obtained from a bulk source. In an aspect, doxycycline monohydrate can be commercially available, for example, as 50 mg, 75 mg, 100 mg, and 150 mg. Various example formulations described herein may be described with respect to 100 mg tablets of doxycycline hyclate; however, it will be appreciated that in various aspects doxycycline monohydrate tablets may be substituted by using equivalent amounts of doxycycline in such doxycycline monohydrate tablets of various strengths. Amounts of other components may similarly be adjusted as necessary.

Econazole is an imidazole derivative. In an aspect, econazole can comprise an ointment or can comprise a dry powder. In an aspect, the dry powder can be obtained from crushed tablets comprising econazole or from a container comprising econazole as a dry powder. In an aspect, econazole can be pure or substantially pure and can be obtained from a bulk source. In an aspect, econazole can be commercially available.

Econazole nitrate is an imidazole derivative. In an aspect, econazole nitrate can comprise an ointment or can comprise a dry powder. In an aspect, the dry powder can be obtained from crushed tablets comprising econazole nitrate or from a container comprising econazole nitrate as a dry powder. In an aspect, econazole can be pure or substantially pure and can be obtained from a bulk source. In an aspect, econazole nitrate can be commercially available as, for example, an econazole nitrate 1.0% cream.

Fluconazole is a synthetic triazole with antifungal activity. In an aspect, fluconazole can comprise an ointment or can comprise a dry powder. In an aspect, the dry powder can be obtained from crushed tablets comprising fluconazole or from a container comprising fluconazole as a dry powder. The fluconazole can be pure or substantially and can be obtained from a bulk source. In an aspect, fluconazole can be commercially available, for example, as 200 mg tablets.

Gentamicin is a complex of closely related aminoglycosides. In an aspect, gentamicin can comprise an ointment or can comprise a dry powder. In an aspect, the dry powder can be obtained from crushed tablets comprising gentamicin or from a container comprising gentamicin as a dry powder. In an aspect, gentamicin can be pure or substantially pure and can be obtained from a bulk source. In an aspect, gentamicin can be commercially available.

Gentamicin sulfate is a complex of closely related aminoglycosides. In an aspect, gentamicin sulfate can comprise an ointment or can comprise a dry powder. In an aspect, the dry powder can be obtained from crushed tablets comprising gentamicin sulfate or from a container comprising gentamicin sulfate as a dry powder. The gentamicin sulfate can be pure or substantially and can be obtained from a bulk source. In an aspect, gentamicin sulfate can be commercially available as, for example, a gentamicin sulfate 0.1% ointment.

Ketoconazole is a synthetic derivative of phenylpiperazine with broad antifungal properties. In an aspect, ketoconazole can comprise an ointment or can comprise a dry powder. In an aspect, the dry powder can be obtained from crushed tablets comprising ketoconazole or from a container comprising ketoconazole as a dry powder. In an aspect, ketoconazole can be pure or substantially pure and can be obtained from a bulk source. In an aspect, ketoconazole can be commercially available, for example, as 200 mg tablets.

Mupirocin is an antibacterial agent that has excellent activity against gram-positive staphylococci and streptococci. In an aspect, mupirocin can comprise mupirocin ointment, which may include mupirocin cream, or can comprise a dry powder. In an aspect, the dry powder can be obtained from crushed tablets comprising mupirocin or from a container comprising mupirocin as a dry powder. In an aspect, mupirocin can be pure or substantially pure and can be obtained from a bulk source. In an aspect, each gram of mupirocin 2.0% ointment can contain 20 mg mupirocin in a bland water miscible ointment base (polyethylene glycol ointment, NF) comprising polyethylene glycol 400 and polyethylene glycol 3350. In an aspect, mupirocin can be commercially available, for example, as a mupirocin 2.0% ointment. In an aspect, a mupirocin 2.0% ointment can be provided in a tube, such as, for example, a 22 g tube. In an aspect, mupirocin ointment may include mupirocin cream USP containing 2.15% w/w mupirocin calcium USP (equivalent to 2% mupirocin free acid) in an oil- and water-based emulsion supplied in 15-gram and 30-gram tubes.

Nystatin is a macrolide antifungal antibiotic complex produced by *Streptomyces noursei*. In an aspect, the nystatin can comprise an ointment or can comprise a dry powder. In an aspect, the dry powder can be obtained from crushed tablets comprising nystatin or from a container comprising nystatin as a dry powder. In an aspect, nystatin can be pure or substantially pure and can be obtained from a bulk source. In an aspect, nystatin can be a powder having about 100,000 units per gram. In an aspect, nystatin can be provided in a container. In an aspect, nystatin can be commercially available, for example, as a 15 g container of nystatin.

Tobramycin is an aminoglycoside, broad-spectrum antibiotic produced by *Streptomyces tenebrarius*. In an aspect, tobramycin can comprise an ointment or can comprise a dry powder. In an aspect, the dry powder can be obtained from crushed tablets comprising tobramycin or from a container comprising tobramycin as a dry powder. In an aspect, tobramycin can be pure or substantially pure and can be obtained from a bulk source. In an aspect, tobramycin can be commercially available.

Tobramycin sulfate is the sulfate salt of tobramycin. In an aspect, tobramycin sulfate can comprise an ointment or can comprise a dry powder. In an aspect, the dry powder can be obtained from crushed tablets comprising tobramycin sulfate or from a container comprising tobramycin sulfate as a dry powder. In an aspect, tobramycin sulfate can be pure or substantially pure and can be obtained from a bulk source. In an aspect, tobramycin sulfate can be tobramycin sulfate for injection USP powder. In an aspect, tobramycin sulfate can be commercially available.

Urea is a compound formed in the liver from ammonia produced by the deamination of amino acids. In an aspect, urea can comprise an ointment or can comprise a dry powder. In an aspect, the dry powder can be obtained from crushed tablets comprising urea or from a container comprising dry powder. In an aspect, urea can be pure or substantially pure and can be obtained from a bulk source. In an aspect, urea can be urea powder USP 99.6. In an aspect, urea can be commercially available. In an aspect, urea can be REA LO 40®, which is a 40.0% urea cream. Each gram of REA LO 40® contains 400 mg urea as the active ingredient and the following inactive ingredients: purified water, emulsifying wax, glycerin, isopropyl myristate, sorbitol, neopentyl glycol dicaprylate/dicaprate, tridecyl stearate, tridecyl trimellitate and dimethyl isosorbide.

As used herein, the recitation of any anti-infective agent inherently encompasses the pharmaceutically acceptable salts thereof.

C. Compounded Compositions

Disclosed herein are compounded compositions for treating an infection.

1. A First Antibacterial Agent and a Second Antibacterial Agent

Disclosed herein is a compounded composition comprising a therapeutically effective amount of a first antibacterial agent and a therapeutically effective amount of a second antibacterial agent. A disclosed compounded composition can comprise a dry powder formulation or can comprise an ointment.

In an aspect, a disclosed compounded composition can comprise from about 1.0% w/w to about 9.0% w/w, from about 2.0% w/w to about 8.0% w/w, from about 3.0% w/w to about 7.0% w/w, or from about 4.0% w/w to about 7.0% w/w of the first antibacterial agent. In an aspect, a disclosed compounded composition can comprise from about 1.0% w/w to about 9.0% w/w, from about 2.0% w/w to about 8.0% w/w, from about 3.0% w/w to about 7.0% w/w, or from about 4.0% w/w to about 7.0% w/w of the second antibacterial agent.

The antibacterial agent may include one or more antibacterials or pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin, as discussed supra.

In an aspect, the first antibacterial agent can comprise mupirocin. Mupirocin is known to the art and discussed supra. In an aspect, the first antibacterial agent can comprise mupirocin. Disclosed herein is a compounded composition comprising a therapeutically effective amount of mupirocin and a therapeutically effective amount of an antibacterial agent. In an aspect, a disclosed compounded composition comprising mupirocin and an antibacterial agent can comprise a dry powder formulation or can comprise an ointment.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.7% w/w, or about 1.8% w/w mupirocin. In an aspect, a disclosed compounded composition comprising mupirocin and an antibacterial agent can comprise from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the antibacterial agent. In an aspect, a disclosed compounded composition comprising mupirocin and an antibacterial agent can comprise about 2.5% w/w, about 5.0% w/w, about 6.0%, or about 7.5% w/w of the antibacterial agent (which is in addition to the amount of mupirocin). Greater or lesser amounts of mupirocin or doxycycline may be used, e.g., less than about 4%, about 3%, about 2%, or about 1% doxycycline.

In an aspect, the second antibacterial agent can comprise tobramycin or a pharmaceutically acceptable salt thereof. In an aspect, a disclosed compounded composition can comprise mupirocin and tobramycin. In an aspect, the mupirocin can comprise an ointment (for example, a mupirocin 2.0% ointment) and the tobramycin or a pharmaceutically acceptable salt thereof can comprise a dry powder. In an aspect, a disclosed compounded composition can comprise about 1.775% w/w mupirocin and about 7.5% w/w tobramycin or a pharmaceutically acceptable salt thereof.

In an aspect, the second antibacterial agent can comprise tobramycin sulfate. In an aspect, a disclosed compounded composition can comprise mupirocin and tobramycin sulfate. In an aspect, the mupirocin can comprise an ointment (for example, a mupirocin 2.0% ointment) and the tobramycin sulfate can comprise a dry powder.

In an aspect, the second antibacterial agent can comprise doxycycline or a pharmaceutically acceptable salt thereof. In an aspect, a disclosed compounded composition can comprise mupirocin and doxycycline or a pharmaceutically acceptable salt thereof. In an aspect, the mupirocin can comprise an ointment (for example, a mupirocin 2.0% ointment) and the doxycycline or a pharmaceutically acceptable salt thereof can comprise a dry powder. In an aspect, a disclosed compounded composition can comprise about 1.756% w/w mupirocin and about 5.0% w/w doxycycline or a pharmaceutically acceptable salt thereof.

In an aspect, the second antibacterial agent can comprise doxycycline hyclate. In an aspect, a disclosed compounded composition can comprise mupirocin and doxycycline hyclate. In an aspect, the mupirocin can comprise an ointment (for example, a mupirocin 2.0% ointment) and the doxycycline hyclate can comprise a dry powder.

In an aspect, the second antibacterial agent can comprise azithromycin. In an aspect, a disclosed compounded composition can comprise mupirocin and azithromycin. In an aspect, the mupirocin can comprise an ointment (for example, a mupirocin 2.0% ointment) and the azithromycin can comprise a dry powder. In an aspect, a disclosed compounded composition can comprise about 1.8% w/w mupirocin and about 5.0% w/w azithromycin.

In an aspect, the first antibacterial agent can comprise mupirocin and the second antibacterial agent can comprise one or more of bacitracin, colistimethate, piperacillin-tazobactam, polymyxin B, streptomycin or pharmaceutically acceptable salts thereof. The mupirocin can comprise an ointment (for example, a mupirocin 2.0% ointment) and the second antibacterial agent may comprise a dry powder. In one embodiment, the second antibacterial agent comprises bacitracin. In one example, the bacitracin comprises bacitracin for injection (USP). In another embodiment, the second antibacterial agent comprises colistimethate. In one example, the colistimethate comprises colistimethate for injection. In a further example, the colistimethate includes colistimethate for injection comprising colistimethate sodium or pentasodium colistin methanesulfonate. In another embodiment, the second antibacterial agent comprises piperacillin-tazobactam. In one example, the piperacillin-tazobactam comprises piperacillin-tazobactam for injection USP. In a further example, the piperacillin-tazobactam comprises piperacillin-tazobactam for injection USP selected from 2.25 gram, 3.375 gram, and 4.5 gram vials. In another embodiment, the second antibacterial agent comprises polymyxin B. In one example, the polymyxin B comprises Polymyxin B for Injection USP. In another embodiment, the second antibacterial agent comprises streptomycin. In one example, the streptomycin comprises streptomycin for injection USP. In a further example, the streptomycin comprises streptomycin sulfate for injection USP. In these or another embodiment, the second antibacterial agent comprises streptomycin and doxycycline.

In an aspect, a disclosed compounded composition can comprise a therapeutically effective amount of one or more additional anti-infective agents. In an aspect, the additional anti-infective agent can be an antibacterial agent. Antibacterial agents are known to the art and discussed supra. In an aspect, the additional anti-infective agent can be an antifungal agent.

In an aspect, the antifungal agent can comprise ketoconazole. In an aspect, a disclosed compounded composition can comprise mupirocin, doxycycline or a pharmaceutically acceptable salt thereof), and ketoconazole. In an aspect, the mupirocin can comprise an ointment (for example, a mupirocin 2.0% ointment), the doxycycline or a pharmaceutically acceptable salt thereof can comprise a dry powder, and the ketoconazole can comprise a dry powder. In an aspect, a disclosed compounded composition can comprise about 1.6% w/w mupirocin, about 5.0% w/w doxycycline or a pharmaceutically acceptable salt thereof, and about 5.0% w/w ketoconazole.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a compounded composition comprising a therapeutically effective amount of a first antibacterial agent, a therapeutically effective amount of a second antibacterial agent, and a therapeutically effective amount of an antifungal agent. In an aspect, a disclosed compounded composition can comprise mupirocin, doxycycline or a pharmaceutically acceptable salt thereof, and ketoconazole. In an aspect, the mupirocin can comprise an ointment, the doxycycline can comprise a dry powder, and the ketoconazole can comprise a dry powder. In an aspect, a disclosed compounded composition can comprise about 1.6% w/w mupirocin, about 5.0% w/w doxycycline or a pharmaceutically acceptable salt thereof, and about 5.0% w/w ketoconazole.

2. Mupirocin and an Antibacterial Agent

Disclosed herein is a compounded composition comprising a therapeutically effective amount of mupirocin and a therapeutically effective amount of an antibacterial agent. In an aspect, a disclosed compounded composition comprising mupirocin and an antibacterial agent can comprise a dry powder formulation or can comprise an ointment.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.756% w/w, or about 1.77% w/w, or about 1.775% w/w, or about 1.8% w/w mupirocin. In an aspect, a disclosed compounded composition comprising mupirocin and an antibacterial agent can comprise from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the antibacterial agent. In an aspect, a disclosed compounded composition comprising mupirocin and an antibacterial agent can comprise about 2.5% w/w, about 5.0% w/w, or about 7.5% w/w of the antibacterial agent. Antibacterial agents are known to the art and discussed supra.

Disclosed herein is a compounded composition comprising a therapeutically effective amount of mupirocin and a therapeutically effective amount of an antibacterial agent (in addition to mupirocin) comprising one or more antibacterials. A disclosed compounded composition can comprise a dry powder formulation, an ointment, or combinations thereof. For example, the antibacterial agent may comprise a dry powder compounded with mupirocin ointment. The dry powder formulation, ointment, or combination thereof may be formulated for mixing with an aqueous diluent for irrigation, e.g., administration to infected skin in a footbath. In some embodiments, a compounded composition may include mupirocin ointment compounded with the second antibacterial agent comprising a dry powder to form a compounded ointment, which may be applied directly to infected skin or may be further combined with an aqueous diluent for irrigation administration, e.g., in a footbath.

In various embodiments, mupirocin comprises a mupirocin ointment. The mupirocin ointment may be a 2% mupirocin ointment. In an aspect, the compounded composition may include from about 20% to about 98%, about 60% to about 90%, about 70% to about 88%, about 75% to about 88% mupirocin 2% ointment w/w.

The antibacterial agent may include one or more antibacterials or pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin, as discussed supra. In an aspect, the antibacterial agent can comprise tobramycin or a pharmaceutically acceptable salt thereof. In an aspect, a disclosed compounded composition can comprise mupirocin and tobramycin. In an aspect, the mupirocin can comprise an ointment (for example, a mupirocin 2.0% ointment) and the tobramycin or a pharmaceutically acceptable salt thereof can comprise a dry powder. In an aspect, a disclosed compounded composition can comprise about 1.775% w/w mupirocin and about 7.5% w/w tobramycin or a pharmaceutically acceptable salt thereof.

In an aspect, the antibacterial agent can comprise tobramycin sulfate. In an aspect, a disclosed compounded composition can comprise mupirocin and tobramycin sulfate. In an aspect, the mupirocin can comprise an ointment (for example, a mupirocin 2.0% ointment) and the tobramycin sulfate can comprise a dry powder. In various embodiments, the antibacterial agent can comprise one or more of bacitracin, colistimethate, piperacillin-tazobactam, polymyxin B, streptomycin or pharmaceutically acceptable salts thereof. The mupirocin can comprise an ointment (for example, a mupirocin 2.0% ointment) and the second antibacterial agent may comprise a dry powder. In one embodiment, the antibacterial agent comprises bacitracin. In one example, the bacitracin comprises Bacitracin for Injection (USP). In another embodiment, the antibacterial agent comprises colistimethate. In one example, the colistimethate comprises Colistimethate for Injection USP. In a further example, the colistimethate includes Colistimethate for Injection comprising colistimethate sodium or pentasodium colistin methanesulfonate. In another embodiment, the antibacterial agent comprises piperacillin-tazobactam. In one example, the piperacillin-tazobactam comprises Piperacillin-Tazobactam for Injection USP. In a further example, the piperacillin-tazobactam comprises Piperacillin-Tazobactam for Injection USP selected from 2.25 gram, 3.375 gram, and 4.5 gram vials. In another embodiment, the antibacterial agent comprises polymyxin B. In one example, the polymyxin B comprises Polymyxin B for Injection USP. In another embodiment, the antibacterial agent comprises streptomycin. In one example, the streptomycin comprises Streptomycin for Injection USP. In a further example, the streptomycin comprises Streptomycin Sulfate for Injection USP. In these or another embodiment, the antibacterial agent comprises streptomycin and doxycycline.

Disclosed herein is a compounded composition comprising a therapeutically effective amount of mupirocin and a therapeutically effective amount of streptomycin or a pharmaceutically acceptable salt thereof. A disclosed compounded composition comprising mupirocin and streptomycin or a salt thereof can comprise a dry powder formulation or can comprise an ointment. In an aspect, a disclosed compounded composition comprising mupirocin and streptomycin or salt thereof can comprise from about 1.0% w/w to about 3.0% w/w, from about 1.2% w/w to about 2.5% w/w, from about 1.4% w/w to about 2.3% w/w, from about 1.4% w/w to about 2.2% w/w, from about 1.5% w/w to about 2.1% w/w, from about 1.6% w/w to about 2.0% w/w, from about 1.7% w/w to about 2.0% w/w, or from about 1.8% w/w to about 2.0% w/w mupirocin. In an aspect, a disclosed compounded composition comprising mupirocin and streptomycin or salt thereof can comprise from about 1.0% w/w to about 5.0% w/w, from about 1.0% w/w to about 3.0% w/w, or from about 1.5% w/w to about 2.5% w/w streptomycin or a pharmaceutically acceptable thereof. In an aspect, a disclosed compounded composition comprising mupirocin and streptomycin or salt thereof can comprise from about 1.8% w/w to about 2.0% w/w mupirocin and from about 3.0% w/w to about 4.0% w/w streptomycin or a pharmaceutically acceptable thereof. In an aspect, a disclosed compounded composition comprising mupirocin and streptomycin or salt thereof can comprise about 1.7% w/w mupirocin and about 4.0% w/w streptomycin or a pharmaceutically acceptable salt thereof.

Disclosed herein is a compounded composition comprising a therapeutically effective amount of mupirocin and an antibacterial agent comprising a therapeutically effective amount of doxycycline or a pharmaceutically acceptable salt thereof. The antibacterial agent may further include one or more additional antibacterials, such as those identified herein. A disclosed compounded composition comprising mupirocin and doxycycline or a salt thereof can comprise a dry powder formulation or can comprise an ointment. In an aspect, a disclosed compounded composition comprising mupirocin and doxycycline or a salt thereof can comprise from about 1.0% w/w to about 3.0% w/w mupirocin. In an aspect, a disclosed compounded composition comprising mupirocin and doxycycline or a salt thereof can comprise about 1.7% w/w mupirocin. In an aspect, a disclosed compounded composition comprising mupirocin and doxycycline or a salt thereof can comprise from about 4.0% to about 6.0% w/w doxycycline or a pharmaceutically acceptable salt thereof. In an aspect, a disclosed compounded composition comprising mupirocin and doxycycline or a salt thereof can comprise about 5.0% w/w doxycycline or a pharmaceutically acceptable salt thereof. In an aspect, a disclosed compounded composition comprising mupirocin and doxycycline or a salt thereof can comprise about 1.7% w/w mupirocin and about 5.0% w/w doxycycline or a pharmaceutically acceptable salt thereof.

Disclosed herein is a compounded composition comprising a therapeutically effective amount of mupirocin and a therapeutically effective amount of tobramycin or a pharmaceutically acceptable salt thereof. A disclosed compounded composition comprising mupirocin and tobramycin or a salt thereof can comprise a dry powder formulation or can comprise an ointment. In an aspect, a disclosed compounded composition comprising mupirocin and tobramycin or a salt thereof can comprise from about 1.0% w/w to about 3.0% w/w of mupirocin. In an aspect, a disclosed compounded composition comprising mupirocin and tobramycin or a salt thereof can comprise about 1.775% w/w of mupirocin. In an aspect, a disclosed compounded composition comprising mupirocin and tobramycin or a salt thereof can comprise from about 7.0% to about 9.0% w/w of tobramycin or a pharmaceutically acceptable salt thereof. In an aspect, a disclosed compounded composition comprising mupirocin and tobramycin or a salt thereof can comprise about 7.5% w/w of tobramycin or a pharmaceutically acceptable salt thereof. In an aspect, a disclosed compounded composition comprising mupirocin and tobramycin or a salt thereof can comprise about 1.775% w/w mupirocin and about 7.5% w/w tobramycin or a pharmaceutically acceptable salt thereof. In an aspect, a disclosed compounded composition comprising mupirocin and tobramycin or a pharmaceutically acceptable salt thereof can comprise ketoconazole or fluconazole.

Disclosed herein is a compounded composition comprising a therapeutically effective amount of mupirocin and a therapeutically effective amount of doxycycline or a pharmaceutically acceptable salt thereof. A disclosed compounded composition comprising mupirocin and doxycycline or a salt thereof can comprise a dry powder formulation or can comprise an ointment. In an aspect, a disclosed compounded composition comprising mupirocin and doxycycline or a salt thereof can comprise from about 1.0% w/w to about 3.0% w/w mupirocin. In an aspect, a disclosed compounded composition comprising mupirocin and doxycycline or a salt thereof can comprise about 1.756% w/w mupirocin. In an aspect, a disclosed compounded composition comprising mupirocin and doxycycline or a salt thereof can comprise from about 4.0% to about 6.0% w/w doxycycline or a pharmaceutically acceptable salt thereof. In an aspect, a disclosed compounded composition comprising mupirocin and doxycycline or a salt thereof can comprise about 5.0% w/w doxycycline or a pharmaceutically acceptable salt thereof. In an aspect, a disclosed compounded composition comprising mupirocin and doxycycline or a salt thereof can comprise about 1.756% w/w mupirocin and about 5.0% w/w doxycycline or a pharmaceutically acceptable salt thereof.

In an aspect, a disclosed compounded composition comprising mupirocin and doxycycline or a salt thereof can comprise ketoconazole. In an aspect, a disclosed compounded composition can comprise about 1.6% w/w mupirocin, about 5.0% w/w doxycycline or a pharmaceutically acceptable salt thereof, and about 5.0% w/w ketoconazole. In an aspect, a disclosed compounded composition can comprise about 1.8% w/w mupirocin, about 2.5% w/w doxycycline or a pharmaceutically acceptable salt thereof, and about 2.5% w/w ketoconazole.

Disclosed herein is a compounded composition comprising a therapeutically effective amount of mupirocin and a therapeutically effective amount of azithromycin. A disclosed compounded composition comprising mupirocin and azithromycin can comprise a dry powder formulation or can comprise an ointment. In an aspect, a disclosed compounded composition comprising mupirocin and azithromycin can comprise from about 1.0% w/w to about 3.0% w/w mupirocin. In an aspect, a disclosed compounded composition comprising mupirocin and azithromycin can comprise about 1.8% w/w mupirocin. In an aspect, a disclosed compounded composition comprising mupirocin and azithromycin can comprise from about 4.0% w/w to about 6.0% w/w azithromycin. In an aspect, a disclosed compounded composition comprising mupirocin and azithromycin can comprise about 5.0% w/w azithromycin. In an aspect, a disclosed compounded composition can comprise about 1.8% w/w mupirocin and about 5.0% w/w azithromycin.

Disclosed herein is a compounded composition comprising a therapeutically effective amount of mupirocin and a therapeutically effective amount of ciprofloxacin or a pharmaceutically acceptable salt thereof. A disclosed compounded composition comprising mupirocin and ciprofloxacin or a salt thereof can comprise a dry powder formulation or can comprise an ointment. In an aspect, a disclosed compounded composition comprising mupirocin and ciprofloxacin or salt thereof can comprise from about 1.0% w/w to about 3.0% w/w, from about 1.2% w/w to about 2.5% w/w, from about 1.4% w/w to about 2.3% w/w, from about 1.4% w/w to about 2.2% w/w, from about 1.5% w/w to about 2.1% w/w, from about 1.6% w/w to about 2.0% w/w, from about 1.7% w/w to about 2.0% w/w, or from about 1.8% w/w to about 2.0% w/w mupirocin. In an aspect, a disclosed compounded composition comprising mupirocin and ciprofloxacin or salt thereof can comprise from about 1.0% w/w to about 5.0% w/w, from about 1.0% w/w to about 3.0% w/w, or from about 1.5% w/w to about 2.5% w/w ciprofloxacin or a pharmaceutically acceptable thereof. In an aspect, a disclosed compounded composition comprising mupirocin and ciprofloxacin or salt thereof can comprise from about 1.8% w/w to about 2.0% w/w mupirocin and from about 1.0% w/w to about 3.0% w/w ciprofloxacin or a pharmaceutically acceptable thereof. In an aspect, a disclosed compounded composition comprising mupirocin and ciprofloxacin or salt thereof can comprise about 1.95% w/w mupirocin and about 2.0% w/w ciprofloxacin or a pharmaceutically acceptable salt thereof.

Disclosed herein is a compounded composition comprising a therapeutically effective amount of mupirocin and a therapeutically effective amount of clindamycin or a pharmaceutically acceptable salt thereof. In an aspect, a disclosed compounded composition comprising mupirocin and clindamycin or a salt thereof can comprise a dry powder formulation or can comprise an ointment. In an aspect, a disclosed compounded composition comprising mupirocin and clindamycin or a salt thereof can comprise from about 1.0% w/w to about 3.0% w/w mupirocin. In an aspect, a disclosed compounded composition comprising mupirocin and clindamycin or a salt thereof can comprise about 1.88% w/w mupirocin. In an aspect, a disclosed compounded composition can comprise from about 4.0% to about 6.0% w/w clindamycin or a pharmaceutically acceptable salt thereof. In an aspect, a disclosed compounded composition comprising mupirocin and clindamycin or a salt thereof can comprise about 5.0% w/w clindamycin or a pharmaceutically acceptable salt thereof. In an aspect, a disclosed compounded composition comprising mupirocin and clindamycin or a salt thereof can comprise about 1.88% w/w mupirocin and about 5.0% w/w clindamycin or a pharmaceutically acceptable salt thereof.

Mupirocin is known to the art and is discussed supra. Antibacterial agents are known to the art and discussed supra. Azithromycin is known to the art and is discussed supra. Ciprofloxacin as well as pharmaceutically acceptable salts thereof are known to the art and are discussed supra. Clindamycin as well as pharmaceutically acceptable salts thereof are known to the art and are discussed supra. Doxycycline as well as pharmaceutically acceptable salts thereof are known to the art and are discussed supra. Ketoconazole is known to the art and is discussed supra. Tobramycin as well as pharmaceutically acceptable salts thereof are known to the art and are discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition can comprise a therapeutically effective amount of one or more additional anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

3. An Antibacterial Agent and an Antifungal Agent

Disclosed herein is a compounded composition comprising a therapeutically effective amount of an antibacterial agent and a therapeutically effective amount of an antifungal agent. A disclosed compounded composition comprising the antibacterial agent and the antifungal agent can comprise a dry powder formulation or can comprise an ointment. The antibacterial agent may include one or more antibacterials pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin, as discussed supra.

The antifungal agent may comprise one or more antifungals pharmaceutically acceptable salts thereof selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole, as discussed supra. The antifungal agent may be in addition to or instead of the second antibacterial agent.

4. Mupirocin and an Antifungal Agent

Disclosed herein is a compounded composition comprising a therapeutically effective amount of mupirocin and a therapeutically effective amount of an antifungal agent. A disclosed compounded composition comprising mupirocin and the antifungal agent can comprise a dry powder formulation or can comprise an ointment.

The antifungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole, as discussed supra. The antifungal agent may be in addition to or instead of the second antibacterial agent.

In an aspect, a disclosed compounded composition comprising mupirocin and an antifungal agent can comprise from about 1.0% w/w to about 3.0% w/w mupirocin. A disclosed compounded composition comprising mupirocin and the antifungal agent can comprise a dry powder formulation or can comprise an ointment. In an aspect, a disclosed compounded composition comprising mupirocin and an antifungal agent can comprise about 1.6% w/w, or about 1.7% w/w, or about 1.8% w/w mupirocin. In an aspect, a disclosed compounded composition comprising mupirocin and an antifungal agent can comprise from about 1.0% w/w to about 9.0% w/w or from about 6.0% w/w to about 8.0% w/w of an antifungal agent. In an aspect, a disclosed compounded composition comprising mupirocin and an antifungal agent can comprise about 2.5% w/w, about 5.0% w/w, or about 7.5% w/w of an antifungal agent.

Disclosed herein is a compounded composition comprising a therapeutically effective amount of mupirocin and a therapeutically effective amount of ketoconazole. In an aspect, a disclosed compounded composition comprising mupirocin and ketoconazole can comprise a dry powder formulation or can comprise an ointment. In an aspect, a disclosed compounded composition comprising mupirocin and ketoconazole can comprise from about 1.0% w/w to about 3.0% w/w mupirocin. In an aspect, a disclosed compounded composition comprising mupirocin and ketoconazole can comprise about 1.77% w/w mupirocin. In an aspect, a disclosed compounded composition comprising mupirocin and ketoconazole can comprise from about 6.5% w/w to about 8.5% w/w ketoconazole. In an aspect, a disclosed compounded composition comprising mupirocin and ketoconazole can comprise about 7.5% w/w ketoconazole. In an aspect, a disclosed compounded composition comprising mupirocin and ketoconazole can comprise about 1.77% w/w mupirocin and about 7.5% w/w ketoconazole.

Disclosed herein is a compounded composition comprising a therapeutically effective amount of mupirocin and a therapeutically effective amount of nystatin. A disclosed compounded composition comprising mupirocin and nystatin can comprise a dry powder formulation or can comprise an ointment. In an aspect, a disclosed compounded composition comprising mupirocin and nystatin can comprise from about 1.0% w/w to about 3.0% w/w mupirocin. In an aspect, a disclosed compounded composition comprising mupirocin and nystatin can comprise about 1.60% w/w mupirocin. In an aspect, a disclosed compounded composition comprising mupirocin and nystatin can comprise from about 15,000 units per gram to about 25,000 units per gram nystatin. In an aspect, a disclosed compounded composition comprising mupirocin and nystatin can comprise about 20,000 units per gram nystatin. In an aspect, a disclosed compounded composition comprising mupirocin and nystatin can comprise about 1.60% w/w mupirocin and about 20,000 units per gram nystatin.

In various embodiments, the antifungal agent may comprise one or more of ketoconazole, voriconazole, or amphotericin B. The antifungal agent may comprise a powder including the antifungal or a pharmaceutically acceptable salt thereof. In one embodiment, the antifungal agent comprises voriconazole. The voriconazole may comprise a dry powder compounded with mupirocin ointment. The voriconazole may comprise Voriconazole for Injection. In a further embodiment, the voriconazole comprises Voriconazole for Injection in 200 mg vials of lyophilized powder. In one embodiment, the antifungal agent comprises amphotericin B. The amphotericin B may comprise Amphotericin B for Injection USP. In one embodiment, the antifungal agent comprises ketoconazole.

In various embodiments, first antibacterial comprises about 1% to about 1.9% w/w mupirocin and the antifungal comprises from about 0.2% to about 6% w/w voriconazole. In one example, the compounded composition comprises about 1.71% w/w mupirocin and 0.8% w/w voriconazole. The mupirocin may be mupirocin 2% ointment in an amount approximately 85.7% w/w of the compounded composition and the voriconazole may include voriconazole for injection in an amount about 0.8% w/w of the compounded composition.

Mupirocin is known to the art and is discussed supra. Antifungal agents are known to the art and is discussed supra. Ketoconazole is known to the art and is discussed supra. Nystatin is known to the art and is discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition can comprise a therapeutically effective amount of one or more additional anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed compounded composition can comprise mupirocin and a therapeutically effective amount of one or more additional anti-infective agents, such as additional second antibacterial agents, as noted above. Additionally or alternatively, the additional anti-infective may include an antifungal agent.

5. Mupirocin, an Antibacterial Agent, and an Antifungal Agent

Disclosed herein is a compounded composition comprising a therapeutically effective amount of mupirocin, a therapeutically effective amount of an antibacterial agent or second antibacterial agent (in addition to mupirocin), and a therapeutically effective amount of an antifungal agent. A disclosed compounded composition comprising mupirocin, an antibacterial agent, and an antifungal agent can comprise a dry powder formulation or can comprise an ointment.

The antifungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole, as discussed supra. The antifungal agent may be in addition to or instead of the second antibacterial agent.

Disclosed herein is a compounded composition comprising a therapeutically effective amount of mupirocin, a therapeutically effective amount of doxycycline or a pharmaceutically acceptable salt thereof, and a therapeutically effective amount of fluconazole. A disclosed compounded composition comprising mupirocin, doxycycline or a salt thereof, and fluconazole can comprise a dry powder formulation or can comprise an ointment.

In an aspect, a disclosed compounded composition comprising mupirocin, doxycycline or a salt thereof, and fluconazole can comprise from about 1.0% w/w to about 3.0% w/w mupirocin. In an aspect, a disclosed compounded composition comprising mupirocin, doxycycline or a salt thereof, and fluconazole can comprise about 1.655% w/w mupirocin. In an aspect, a disclosed compounded composition comprising mupirocin, doxycycline or a salt thereof, and fluconazole can comprise from about 1.5% w/w to about 3.5% w/w fluconazole. In an aspect, a disclosed compounded composition comprising mupirocin, doxycycline or a salt thereof, and fluconazole can comprise about 2.5% w/w fluconazole. In an aspect, a disclosed compounded composition comprising mupirocin, doxycycline or a salt thereof, and fluconazole can comprise from about 4.0% to about 6.0% w/w doxycycline or a pharmaceutically acceptable salt thereof. In an aspect, a disclosed compounded composition comprising mupirocin, doxycycline or a salt thereof, and fluconazole can comprise about 5.0% w/w doxycycline or a pharmaceutically acceptable salt thereof. In an aspect, a disclosed compounded composition comprising mupirocin, doxycycline or a salt thereof, and fluconazole can comprise about 1.655% w/w mupirocin, about 5.0% w/w doxycycline or a pharmaceutically acceptable salt thereof, and about 2.5% w/w fluconazole.

Disclosed herein is a compounded composition comprising a therapeutically effective amount of mupirocin, a therapeutically effective amount of doxycycline or a pharmaceutically acceptable salt thereof, and a therapeutically effective amount of ketoconazole. A disclosed compounded composition comprising mupirocin, doxycycline or a salt thereof, and ketoconazole can comprise a dry powder formulation or can comprise an ointment.

In an aspect, a disclosed compounded composition comprising mupirocin, doxycycline or a salt thereof, and ketoconazole can comprise from about 1.0% w/w to about 3.0% w/w mupirocin. In an aspect, a disclosed compounded composition comprising mupirocin, doxycycline or salt thereof, and ketoconazole can comprise about 1.6% w/w or about 1.8% w/w mupirocin. In an aspect, a disclosed compounded composition comprising mupirocin, doxycycline or a salt thereof, and ketoconazole can comprise from about 1.5% to about 3.5% w/w or from about 4.0% to about 6.0% w/w doxycycline or a pharmaceutically acceptable salt thereof. In an aspect, a disclosed compounded composition comprising mupirocin, doxycycline or a salt thereof, and ketoconazole can comprise about 2.5% w/w or 5.0% w/w doxycycline or a pharmaceutically acceptable salt thereof. In an aspect, a disclosed compounded composition comprising mupirocin, doxycycline or a salt thereof, and ketoconazole can comprise from about 1.5% w/w to about 3.5% w/w or from about 4.0% to about 6.0% w/w ketoconazole. In an aspect, a disclosed compounded composition comprising mupirocin, doxycycline or a salt thereof, and ketoconazole can comprise about 2.5% w/w or about 5.0% w/w ketoconazole. In an aspect, a disclosed compounded composition comprising mupirocin, doxycycline or salt thereof, and ketoconazole can comprise about 1.6% w/w mupirocin, about 5.0% w/w doxycycline or a pharmaceutically acceptable salt thereof, and about 5.0% w/w ketoconazole. In an aspect, a disclosed compounded composition comprising mupirocin, doxycycline or a salt thereof, and ketoconazole can comprise about 1.8% w/w mupirocin, about 2.5% w/w doxycycline or a pharmaceutically acceptable salt thereof, and about 2.5% w/w ketoconazole.

Disclosed herein is a compounded composition comprising a therapeutically effective amount of mupirocin, a therapeutically effective amount of tobramycin or a pharmaceutically acceptable salt thereof, and ketoconazole or fluconazole. A disclosed compounded composition comprising mupirocin, tobramycin or a salt thereof, and ketoconazole or fluconazole can comprise a dry powder formulation or can comprise an ointment.

In an aspect, a disclosed compounded composition comprising mupirocin, tobramycin or a salt thereof, and ketoconazole can comprise from about 1.4% w/w to about 2.0% w/w, from about 1.5% w/w to about 1.9% w/w, or from about 1.6% w/w to about 1.8% w/w mupirocin. In an aspect, a disclosed compounded composition comprising mupirocin, tobramycin or a salt thereof, and ketoconazole can comprise about 1.695% w/w or about 1.8475% w/w mupirocin. In an aspect, a disclosed compounded composition comprising mupirocin, tobramycin or a salt thereof, and ketoconazole can comprise from about 1.0% w/w to about 7.0% w/w or from about 2.0% to about 6.0% w/w tobramycin or a pharmaceutically acceptable salt thereof. In an aspect, a disclosed compounded composition comprising mupirocin, tobramycin or a salt thereof, and ketoconazole can comprise about 2.5% w/w or about 5.0% w/w tobramycin or a pharmaceutically acceptable salt thereof. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w ketoconazole. In an aspect, a disclosed compounded composition comprising mupirocin, tobramycin or a salt thereof, and ketoconazole can comprise about 2.5% w/w or 5.0% w/w ketoconazole.

In an aspect, a disclosed compounded composition comprising mupirocin, tobramycin or a salt thereof, and ketoconazole can comprise about 1.695% w/w mupirocin, about 5.0% tobramycin or a pharmaceutically acceptable salt thereof, and about 5.0% ketoconazole.

In an aspect, a disclosed compounded composition comprising mupirocin, tobramycin or a salt thereof, and ketoconazole can comprise about 1.8475% w/w mupirocin, about 2.5% tobramycin or a pharmaceutically acceptable salt thereof, and about 2.5% ketoconazole.

In an aspect, a disclosed compounded composition comprising mupirocin, tobramycin or a salt thereof, and fluconazole can comprise about 1.7% w/w mupirocin, about 5% w/w tobramycin or a pharmaceutically acceptable salt thereof, and about 2.5% w/w fluconazole.

Disclosed herein is a compounded composition comprising a therapeutically effective amount of mupirocin, a therapeutically effective amount of fluoroquinolone, and a therapeutically effective amount of an azole. A disclosed compounded composition comprising mupirocin, a fluoroquinolone, and an azole can comprise a dry powder formulation or can comprise an ointment. In an aspect, a fluoroquinolone can comprise enoxacin, ciprofloxacin, norfloxacin, ofloxacin, levofloxacin, trovafloxacin, gatifloxacin, or moxifloxacin. In an aspect, a fluoroquinolone can comprise ciprofloxacin. In an aspect, an azole can comprise clotrimazole, econazole, oxiconazole, ketoconazole, miconazole, sulconazole, fluconazole, itraconazole, or voriconazole. In an aspect, an azole can comprise ketoconazole.

In an aspect, a disclosed compounded composition comprising mupirocin, a fluoroquinolone, and an azole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, a fluoroquinolone, and an azole can comprise about 1.8453% w/w mupirocin. In an aspect, a disclosed compounded composition comprising mupirocin, a fluoroquinolone, and an azole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w of a fluoroquinolone. In an aspect, a disclosed compounded composition comprising mupirocin, a fluoroquinolone, and an azole can comprise about 2.5% w/w of a fluoroquinolone. In an aspect, a disclosed compounded composition comprising mupirocin, a fluoroquinolone, and an azole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w of an azole. In an aspect, a disclosed compounded composition comprising mupirocin, a fluoroquinolone, and an azole can comprise about 2.5% w/w of an azole. In an aspect, an azole can comprise ketoconazole.

In an aspect, a disclosed compounded composition comprising mupirocin, a fluoroquinolone, and an azole can comprise about the same amount of both an azole and a fluoroquinolone. In an aspect, a disclosed compounded composition comprising mupirocin, a fluoroquinolone, and an azole can comprise about 1.8453% w/w mupirocin, about 2.5% w/w of a fluoroquinolone, and about 2.5% w/w of an azole.

Disclosed herein is a compounded composition comprising a therapeutically effective amount of mupirocin, a therapeutically effective amount of ciprofloxacin or a pharmaceutically acceptable salt thereof, and a therapeutically effective amount of ketoconazole. A disclosed compounded composition comprising mupirocin, ciprofloxacin or a salt thereof, and ketoconazole can comprise a dry powder formulation or can comprise an ointment.

In an aspect, a disclosed compounded composition comprising mupirocin, ciprofloxacin or a salt thereof, and ketoconazole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, ciprofloxacin or a salt thereof, and ketoconazole can comprise about 1.768% w/w or 1.8453% w/w mupirocin. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ciprofloxacin or a pharmaceutically acceptable salt thereof. In an aspect, a disclosed compounded composition comprising mupirocin, ciprofloxacin or a salt thereof, and ketoconazole can comprise about 2.5% w/w or about 5.0% w/w ciprofloxacin or a pharmaceutically acceptable salt thereof. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ketoconazole. In an aspect, a disclosed compounded composition comprising mupirocin, ciprofloxacin or a salt thereof, and ketoconazole can comprise about 2.5% w/w or about 5.0% w/w ketoconazole. In an aspect, a disclosed compounded composition can comprise about 1.8453% w/w mupirocin, about 2.5% w/w ciprofloxacin or a pharmaceutically acceptable salt thereof, and about 2.5% w/w ketoconazole. In an aspect, a disclosed compounded composition can comprise from about 1.768% w/w to about 1.8% w/w mupirocin, about 5% w/w ciprofloxacin or a pharmaceutically acceptable salt thereof, and about 2.5% w/w ketoconazole.

Disclosed herein is a compounded composition comprising a therapeutically effective amount of mupirocin, a therapeutically effective amount of an additional or second antibacterial agent, and a therapeutically effective amount of an antifungal agent selected from one or more antifungals described herein, such as one or more of ketoconazole, voriconazole, or amphotericin B. The second antibacterial agent may comprise one or more of doxycycline, bacitracin, colistimethate, piperacillin-tazobactam, polymyxin B, or streptomycin. In one embodiment, the second antibacterial agent comprises doxycycline and one or more of bacitracin, colistimethate, piperacillin-tazobactam, polymyxin B, or streptomycin. Other antibacterials may be used in addition to or instead of doxycycline, bacitracin, colistimethate, piperacillin-tazobactam, polymyxin B, or streptomycin, such as the antibacterials described herein.

In one embodiment, a disclosed compounded composition comprising mupirocin and doxycycline or a salt thereof comprises an antifungal agent comprising ketoconazole. In an aspect, a disclosed compounded composition can comprise about 1.6% w/w mupirocin, about 5.0% w/w doxycycline or a pharmaceutically acceptable salt thereof, and about 5.0% w/w ketoconazole. In an aspect, a disclosed compounded composition can comprise about 1.8% w/w mupirocin, about 2.5% w/w doxycycline or a pharmaceutically acceptable salt thereof, and about 2.5% w/w ketoconazole.

In an aspect, a disclosed compounded composition can comprise mupirocin, an antifungal agent, and a second antibacterial agent. In one example, the antifungal agent includes ketoconazole and the second antibacterial agent includes one or more antibacterials (which may include pharmaceutically acceptable salts) selected from bacitracin, colistimethate, piperacillin-tazobactam, polymyxin B, streptomycin, or doxycycline. In one such example, the antifungal agent includes ketoconazole and the second antibacterial agent includes doxycycline and one or more antibacterials selected from bacitracin, colistimethate, piperacillin-tazobactam, polymyxin B, or streptomycin. In an aspect, the mupirocin can comprise an ointment (for example, a mupirocin 2.0% ointment), the doxycycline or a pharmaceutically acceptable salt thereof can comprise a dry powder, and the ketoconazole can comprise a dry powder. In an aspect, a disclosed compounded composition can comprise from about 1.6% to about 1.8% w/w mupirocin, from about 1.0% to about 5.0% w/w doxycycline or a pharmaceutically acceptable salt thereof, and from about 1.0% to about 5.0% w/w ketoconazole. In an aspect, a disclosed compounded composition can comprise from about 1.6 to about 1.7% w/w mupirocin, from about 1.0% to about 5.0% w/w doxycycline, from about 2% to about 6% w/w streptomycin, and from about 1.0% to about 5.0% w/w ketoconazole. In another embodiment, streptomycin may be replaced by about antibacterial. For example, streptomycin may be replaced by an antibacterial selected from bacitracin, colistimethate, piperacillin-tazobactam, or polymyxin B in an amount from about 2% to about 6% w/w. In another embodiment, streptomycin may be replaced by an antifungal. For example, streptomycin may be replaced by an antifungal selected from voriconazole or amphotericin B in an amount from about 1% to about 5% w/w. In one example, a disclosed compounded composition can comprise about 1.7% w/w mupirocin, about 2% w/w doxycycline, about 4% w/w streptomycin, and about 2.5% w/w ketoconazole.

In one aspect, a disclosed compounded composition comprises a compounded ointment comprising doxycycline, tobramycin, mupirocin, and ketoconazole. The doxycycline may comprise crushed doxycycline hyclate tablets, e.g., 100 mg tablets. The tobramycin may comprise tobramycin sulfate for injection powder. The mupirocin may comprise mupirocin 2% ointment. The ketoconazole may comprise crushed ketoconazole tablets, e.g., 200 mg tablets.

In various aspects, the compounded composition may comprise between about 0.5% and about 5.0%, about 0.5% and about 4.0%, about 0.5% and about 3.0%, about 0.5% and about 2.5%, about 0.5% and about 2.0%, about 0.5% and about 1.5%, about 1.0% and about 5.0%, about 1.0% and about 4.0%, about 1.0% and about 3.0%, about 1.0% and about 2.5%, about 1.0% and about 2.0%, about 1.5% and about 5.0%, about 1.5% and about 4.0%, about 1.5% and about 3.0%, about 1.5% and about 2.5%, about 1.5% and about 2.0%, about 2.0% and about 5.0%, about 2.0% and about 4.0%, about 2.0% and about 3.0%, about 2.0% and about 2.5%, about 2.5% and about 5.0%, about 2.5% and about 4.0%, about 2.5% and about 3.0%, about 3.0% and about 4.0%, or about 4.0% and 5.0% (w/w) doxycycline; between about 0.5% and about 5.0%, about 0.5% and about 4.0%, about 0.5% and about 3.0%, about 0.5% and about 2.5%, about 0.5% and about 2.0%, about 0.5% and about 1.5%, about 1.0% and about 5.0%, about 1.0% and about 4.0%, about 1.0% and about 3.0%, about 1.0% and about 2.5%, about 1.0% and about 2.0%, about 1.5% and about 5.0%, about 1.5% and about 4.0%, about 1.5% and about 3.0%, about 1.5% and about 2.5%, about 1.5% and about 2.0%, about 2.0% and about 5.0%, about 2.0% and about 4.0%, about 2.0% and about 3.0%, about 2.0% and about 2.5%, about 2.5% and about 5.0%, about 2.5% and about 4.0%, about 2.5% and about 3.0%, about 3.0% and about 5.0%, about 3.0% and about 4.0%, or about 4.0% and 5.0% (w/w) tobramycin; between about 0.5% and about 5.0%, about 0.5% and about 4.0%, about 0.5% and about 3.0%, about 0.5% and about 2.5%, about 0.5% and about 2.0%, about 0.5% and about 1.5%, about 1.0% and about 5.0%, about 1.0% and about 4.0%, about 1.0% and about 3.0%, about 1.0% and about 2.5%, about 1.0% and about 2.0%, about 1.5% and about 5.0%, about 1.5% and about 4.0%, about 1.5% and about 3.0%, about 1.5% and about 2.5%, about 1.5% and about 2.0%, about 2.0% and about 5.0%, about 2.0% and about 4.0%, about 2.0% and about 3.0%, about 2.0% and about 2.5%, about 2.5% and about 5.0%, about 2.5% and about 4.0%, about 2.5% and about 3.0%, about 3.0% and about 5.0%, about 3.0% and about 4.0%, or about 4.0% and 5.0% (w/w) ketoconazole; and between about 0.5% and about 1.8%, about 0.5% and about 1.5%, about 0.5% and about 1.0%, about 1.0% and about 1.8%, about 1.0% and about 1.8%, about 1.0% and about 1.5%, or about 1.5% and about 1.8% (w/w) mupirocin. In a further aspect, the tobramycin is replaced by the same weight percent of ciprofloxacin. The bulk or remainder of the compounded ointment may be provided by the mupirocin ointment. In some aspects, additional base or carrier ointments may be added.

In various embodiments, the compounded ointment comprises about 1% to about 1.9% w/w mupirocin and from about 0.2% to about 6% w/w voriconazole. In one example, the compounded ointment comprises about 1.71% w/w mupirocin and 0.8% w/w voriconazole. The mupirocin may be mupirocin 2% ointment in an amount approximately 85.7% w/w of the compounded ointment and the voriconazole may include voriconazole for injection in an amount about 0.8% w/w of the compounded ointment.

In various embodiments, the compounded ointment comprises about 1% to about 1.9% w/w mupirocin, from about 0.2% to about 6% w/w voriconazole, and from about 0.2% to about 6% w/w streptomycin. In one example, the compounded ointment comprises about 1.6% w/w mupirocin, about 0.8% w/w voriconazole, and about 4% w/w streptomycin. The mupirocin may be mupirocin 2% ointment in an amount approximately 80% w/w of the compounded ointment, the voriconazole may include voriconazole for injection in an amount about 0.8% w/w of the compounded ointment, and the streptomycin may comprise streptomycin sulfate for injection in an amount about 5.528% w/w of the compounded ointment.

In various embodiments, the compounded ointment comprises about 1% to about 1.9% w/w mupirocin, from about 0.2% to about 6% w/w voriconazole, from about 0.2% to about 6% w/w streptomycin, and from about 0.2% to about 6% doxycycline. In one example, the compounded ointment comprises about 1.55% w/w mupirocin, about 0.8% w/w voriconazole, about 4% w/w streptomycin, and about 1% w/w doxycycline. The mupirocin may be mupirocin 2% ointment in an amount approximately 77.6% w/w of the compounded ointment, the voriconazole may include voriconazole for injection in an amount about 0.8% w/w of the compounded ointment, the streptomycin may comprise streptomycin sulfate for injection in an amount about 5.528% w/w of the compounded ointment, and the doxycycline may comprise doxycycline hyclate 100 mg tablets in an amount about 2.435% w/w of the compounded ointment. Other strength tablets may be used.

In various embodiments, the compounded ointment comprises about 1% to about 1.9% w/w mupirocin, from about 0.2% to about 6% w/w voriconazole, from about 0.2% to about 6% w/w tobramycin, and from about 0.2% to about 6% doxycycline. In one example, the compounded ointment comprises about 1.62% w/w mupirocin, about 0.8% w/w voriconazole, about 1.2% w/w tobramycin, and about 1% w/w doxycycline. The mupirocin may be mupirocin 2% ointment in an amount approximately 81.3% w/w of the compounded ointment, the voriconazole may include voriconazole for injection in an amount about 0.8% w/w of the compounded ointment, the tobramycin may comprise tobramycin sulfate for injection in an amount about 1.8% w/w of the compounded ointment, and the doxycycline may comprise doxycycline hyclate 100 mg tablets in an amount about 2.435% w/w of the compounded ointment. Other strength tablets may be used.

In various embodiments, the compounded ointment comprises about 1% to about 1.9% w/w mupirocin, from about 0.2% to about 6% w/w ketoconazole, from about 0.2% to about 6% w/w streptomycin, and from about 0.2% to about 6% doxycycline. In one example, the compounded ointment comprises about 1.71% w/w mupirocin, about 2% w/w ketoconazole, about 4% w/w streptomycin, and about 2% w/w doxycycline. The mupirocin may be mupirocin 2% ointment in an amount approximately 85.7% w/w of the compounded ointment, the ketoconazole may include ketoconazole 200 mg tablets in an amount about 3.875% w/w of the compounded ointment, the streptomycin may comprise streptomycin sulfate for injection in an amount about 5.528% w/w of the compounded ointment, and the doxycycline may comprise doxycycline hyclate 100 mg tablets in an amount about 4.87% w/w of the compounded ointment. Other strength tablets may be usedAs described further below, a method of compounding the compounded composition may comprise grinding a suitable amount of doxycycline hyclate tablets and ketoconazole tablets and combining the powder from the crushed tablets with a suitable amount of tobramycin sulfate for injection powder and a suitable volume of mupirocin 2% ointment. For example, compounding a compounded composition comprising about 2.5% (w/w) doxycycline, about 2.5% (w/w) tobramycin, about 1.726% (w/w) mupirocin, and about 2.5% (w/w) ketoconazole may include crushing doxycycline hyclate tablets and ketoconazole tablets and combining the powder from the crushed tablets with a suitable amount of tobramycin sulfate for injection powder and a suitable volume of mupirocin 2% ointment. Each gram of the compounded composition contains about 2.5% doxycycline (or 25 mg doxycycline), which is equivalent to 0.25 tablets of 100 mg doxycycline tablets, which is equivalent to 60.875 mg (25% of 243.5 mg total weight of a 100 mg doxycycline tablet). Each gram of compounded composition contains about 2.5% ketoconazole (or 25 mg ketoconazole) which is equivalent to about 0.125 tablets of 200 mg ketoconazole tablets, which is equivalent to about 38.75 mg (25% of 310 mg total weight of a 100 mg ketoconazole tablet). Each gram of compounded composition contains about 2.5% tobramycin, equivalent to about 25 mg tobramycin USP, equivalent to about 37.5 mg of tobramycin sulfate, which may reflect usage of about 2% of 1 vial of tobramycin 1.2 g vials per gram of compounded composition. The powders may be added to a suitable amount of mupirocin ointment to formulate the desired concentration of the compounded composition ointment. For example, for every gram of compounded composition ointment, the powders may be combined with about 0.863 g of mupirocin 2% ointment. The combined mixture may be suitably processed in an ointment mill as described elsewhere herein. The compounded composition may be packaged in suitable packaging, e.g., tubes or syringes. As noted elsewhere herein, the term "about" means a value falling within a range that is ±10% of the stated value. Thus, in an aspect, the skilled person can combine 0.863 g±10% mupirocin 2.0% ointment (e.g., from about 0.7767 g-0.9493 g), 0.060875 g±10% powder from crushed doxycycline hyclate 100 mg tablets (e.g., from about 0.0547875 g-0.0669625 g), 0.0375 g±10% tobramycin sulfate USP powder for injection (e.g., from about 0.03375 g-0.04125 g), and 0.03875 g±10% powder from crushed ketoconazole 200 mg tablets (e.g., from about 0.034875 g-0.042625 g) and mix together according to a method described above to make about 1.0 g±10% of the compounded composition. Other strength tablets and ointments may be used wherein amounts combined are suitably adjusted.

In these or other embodiments, the compounded composition may comprise between 5.5% and 6.5% w/w crushed doxycycline hyclate 100 mg tablets. The compounded composition may further comprise between 3.3% and 4.3% w/w crushed ketoconazole 200 mg tablets. The compounded composition may further comprise between 3.2% and 4.2% w/w tobramycin sulfate USP powder for injection. In any of the above combinations, the compounded composition may comprise at least 60%, 75%, 80%, 85%, or 89% mupirocin ointment. In one example, mupirocin ointment makes up the remaining weight of the composition. For example, the compounded composition may comprise between 84.9% and 88.9% mupirocin ointment.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin. In one example, the compounded composition comprises about 1.6% w/w mupirocin, about 0.8% w/w voriconazole, and about 4% w/w streptomycin. The mupirocin may be mupirocin 2% ointment in an amount approximately 80% w/w of the compounded composition, the voriconazole may include voriconazole for injection in an amount about 0.8% w/w of the compounded composition, and the streptomycin may comprise streptomycin sulfate for injection in an amount about 5.528% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin and about 0.2% to about 6% w/w doxycycline. In one example, the compounded composition comprises about 1.55% w/w mupirocin, about 0.8% w/w voriconazole, about 4% w/w streptomycin, and about 1% w/w doxycycline. The mupirocin may be mupirocin 2% ointment in an amount approximately 77.6% w/w of the compounded composition, the voriconazole may include voriconazole for injection in an amount about 0.8% w/w of the compounded composition, the streptomycin may comprise streptomycin sulfate for injection in an amount about 5.528% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w tobramycin and about 0.2% to about 6% w/w doxycycline. In one example, the compounded composition comprises about 1.62% w/w mupirocin, about 0.8% w/w voriconazole, about 1.2% w/w tobramycin, and about 1% w/w doxycycline. The mupirocin may be mupirocin 2% ointment in an amount approximately 81.3% w/w of the compounded composition, the voriconazole may include voriconazole for injection in an amount about 0.8% w/w of the compounded composition, the tobramycin may comprise tobramycin sulfate for injection in an amount about 1.8% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w ketoconazole, and the second antibacterial comprises from about 0.2% to about 6% w/w streptomycin and about 0.2% to about 6% w/w doxycycline. In one example, the compounded composition comprises about 1.71% w/w mupirocin, about 2% w/w ketoconazole, about 4% w/w streptomycin, and about 2% w/w doxycycline. The mupirocin may be mupirocin 2% ointment in an amount approximately 85.7% w/w of the compounded composition, the ketoconazole may include ketoconazole 200 mg tablets in an amount about 3.875% w/w of the compounded composition, the streptomycin may comprise streptomycin sulfate for injection in an amount about 5.528% w/w of the compounded composition, and the doxycycline may comprise doxycycline hyclate 100 mg tablets in an amount about 4.87% w/w of the compounded composition.

As another example, a method of compounding the compounded composition may comprise grinding a suitable amount of doxycycline hyclate tablets, ketoconazole tablets, and ciprofloxacin tablets and combining the powder from the crushed tablets with a suitable volume of mupirocin 2% ointment. For example, compounding a compounded composition comprising about 2.5% (w/w) doxycycline, about 2.5% (w/w) ciprofloxacin, about 1.724% (w/w) mupirocin, and about 2.5% (w/w) ketoconazole may include crushing tablets of doxycycline hyclate, ketoconazole, and ciprofloxacin and combining the powder from the crushed tablets with a volume of mupirocin 2% ointment. Each gram of the compounded composition contains about 2.5% doxycycline (or 25 mg doxycycline), which is equivalent to 0.25 tablets of 100 mg doxycycline tablets, which is equivalent to 60.875 mg (25% of 243.5 mg total weight of a 100 mg doxycycline tablet). Each gram of compounded composition contains about 2.5% ketoconazole (or 25 mg ketoconazole) which is equivalent to about 0.125 tablets of 200 mg ketoconazole tablets, which is equivalent to about 38.75 mg (25% of 310 mg total weight of a 100 mg ketoconazole tablet). Each gram of compounded composition contains about 2.5% ciprofloxacin (or 25 mg ketoconazole) which is equivalent to about 0.033 tablets of 750 mg ciprofloxacin tablets, which is equivalent to about 39.9 mg (25% of 1.137 g total weight of a 750 mg ciprofloxacin tablet). The powders may be added to a suitable amount of mupirocin ointment to formulate the desired concentration of the compounded composition ointment. For example, for every gram of compounded composition ointment, the powders may be combined with about 0.863 g of mupirocin 2% ointment. The combined mixture may be suitably processed in an ointment mill as described elsewhere herein. The compounded composition may be packaged in suitable packaging, e.g., tubes or syringes. As noted elsewhere herein, the term "about" means a value falling within a range that is ±10% of the stated value. Thus, in an aspect, the skilled person can combine 0.862 g±10% mupirocin 2.0% ointment (e.g., from about 0.7758 g-0.9482 g), 0.060875 g±10% powder from crushed doxycycline hyclate 100 mg tablets (e.g., from about 0.0547875 g-0.0669625 g), 0.0379 g±10% powder from ciprofloxacin 750 mg tablets (e.g., from about 0.03411 g-0.04169 g), and 0.03875 g±10% powder from crushed ketoconazole 200 mg tablets (e.g., from about 0.034875 g-0.042625 g) and mix together according to a method described above to make about 1.0 g±10% of the compounded composition. Other strength tablets and ointments may be used wherein amounts combined are suitably adjusted. In these or other embodiments, the compounded composition comprises between 5.5% and 6.5% w/w crushed doxycycline hyclate 100 mg tablets. The compounded composition may further comprise between 3.3% and 4.3% w/w crushed ketoconazole 200 mg tablets. The compounded composition may further comprise between 3.3% and 4.3% w/w crushed ciprofloxacin 750 mg tablets. In any of the above combinations, the compounded composition may comprise at least 60%, 75%, 80%, 85%, or 89% mupirocin ointment. In one example, mupirocin ointment makes up the remaining weight of the composition. For example, the compounded composition may comprise between 84.9% and 88.9% mupirocin ointment. Mupirocin is known to the art and is discussed supra. Antibacterial agents are known to the art and are discussed supra. Antifungal gents are known to the art and are discussed supra. Azithromycin is known to the art and is discussed supra. Azoles are known to the art and are discussed supra. Ciprofloxacin as well as pharmaceutically acceptable salts thereof are known to the art and are discussed supra. Clindamycin as well as pharmaceutically acceptable salts thereof are known to the art and are discussed supra. Doxycycline as well as pharmaceutically acceptable salts thereof are known to the art and are discussed supra. Fluoroquinolones are known to the art and are discussed supra. Ketoconazole is known to the art and is discussed supra. Tobramycin as well as pharmaceutically acceptable salts thereof are known to the art and are discussed supra.

In an aspect, a disclosed compounded composition can comprise a therapeutically effective amount of one or more additional anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

6. Miscellaneous

The compounded composition may include multiple anti-infectives in combination with mupirocin, such as mupirocin 2% ointment. The multiple anti-infectives may be selected from any combination of the antibacterial and antifungals described herein. In one example, one or more of the anti-infectives may comprise one or more antibacterials or pharmaceutically acceptable salt thereof selected from bacitracin, colistimethate, piperacillin-tazobactam, polymyxin B, streptomycin, or combination thereof and/or one or more one or more antifungals or pharmaceutically acceptable salt thereof selected from voriconazole, amphotericin B, or combination thereof. In these or other embodiments, one or more of the anti-infectives may comprise the antibacterial doxycycline or pharmaceutically acceptable salt and/or the antifungal ketoconazole or pharmaceutically acceptable salt thereof. In some embodiments, mupirocin may be provided in an ointment. In various embodiments, the compounded composition may include from about 20% to about 95%, about 60% to about 90%, about 70% to about 88%, about 75% to about 88% mupirocin 2% ointment w/w. As introduced above, the compounded composition may include additional anti-infectives such as a second antibacterial agent and an antifungal agent may comprise powders compounded with the mupirocin ointment. In an aspect, the compounded composition may include an amount of second antibacterial agent from about 1% to about 30%, about 1% to about 20%, about 1% to about 10%, about 1% to about 5%, about 4% to about 15%, about 4% to about 10%, or about 4% to about 8% w/w. In an aspect, the compounded composition may include an amount of antifungal agent from about 1% to about 30%, about 1% to about 20%, about 1% to about 10%, about 1% to about 5%, about 2% to about 15%, about 2% to about 10%, or about 2% to about 8% w/w. In various embodiments, the powders may comprise anti-infective tablets (ground, e.g., crushed), bulk powder, or anti-infective for injection. Anti-infectives for injection may comprise powder, typically available in vials, for reconstitution. In some embodiments, the compounded composition may include from about 1% to about 30%, about 1% to about 20%, about 4% to about 20%, about 4% to about 15% w/w anti-infective for injection. In various embodiments, the compounded composition comprises anti-infective for injection in an amount between about 3% and about 20% w/w. In an aspect, the anti-infective for injection comprises one or more of bacitracin for injection, colistimethate sodium for injection, pentasodium colistin methanesulfonate for injection, piperacillin-tazobactam for injection, polymyxin B for injection USP, streptomycin sulfate for injection, tobramycin sulfate for injection, voriconazole for injection, or amphotericin B for injection. In these or other embodiments, the compounded composition may include from about 1% to about 30%, about 1% to about 20%, about 1% to about 10%, about 3% to about 15%, or about 4% to about 12% crushed anti-infective tablets.

Disclosed herein is a compounded composition comprising a therapeutically effective amount of mupirocin, a therapeutically effective of amount of clindamycin or a pharmaceutically acceptable salt thereof, a therapeutically effective of amount of gentamicin or a pharmaceutically acceptable salt thereof, and a therapeutically effective of amount of econazole or a pharmaceutically acceptable salt thereof. A disclosed compounded composition comprising mupirocin, clindamycin or a salt thereof, gentamicin or a salt thereof, and econazole or a salt thereof can comprise a dry powder formulation or can comprise an ointment.

In an aspect, a disclosed compounded composition comprising mupirocin, clindamycin or a salt thereof, gentamicin or a salt thereof, and econazole or a salt thereof can comprise from about 0.5% w/w to about 1.4% w/w, from about 0.6% w/w to about 1.3% w/w, from about 0.7% w/w to about 1.2% w/w, from about 0.7% w/w to about 1.1% w/w, from about 0.8% w/w to about 1.0% w/w, or from about 0.9% w/w to about 1.0% w/w mupirocin.

In an aspect, a disclosed compounded composition comprising mupirocin, clindamycin or a salt thereof, gentamicin or a salt thereof, and econazole or a salt thereof can comprise from about 0.01% w/w to about 0.08% w/w or from about 0.04% w/w and about 0.06% w/w clindamycin or a pharmaceutically acceptable salt thereof. In an aspect, a disclosed compounded composition comprising mupirocin, clindamycin or a salt thereof, gentamicin or a salt thereof, and econazole or a salt thereof can comprise about 0.01% w/w, about 0.02% w/w, about 0.03% w/w, about 0.06% w/w, or about 0.07% w/w clindamycin or a pharmaceutically acceptable salt thereof.

In an aspect, a disclosed compounded composition comprising mupirocin, clindamycin or a salt thereof, gentamicin or a salt thereof, and econazole or a salt thereof can comprise from about 0.01% w/w to about 0.05% w/w, from about 0.01% w/w to about 0.04% w/w, from about 0.01% w/w to about 0.03% w/w, or from about 0.015% w/w to about 0.025% w/w gentamicin or a pharmaceutically acceptable salt thereof.

In an aspect, a disclosed compounded composition comprising mupirocin, clindamycin or a salt thereof, gentamicin or a salt thereof, and econazole or a salt thereof can comprise from about 0.1% w/w to about 0.6% w/w, from about 0.2% w/w to about 0.5% w/w, from about 0.2% w/w to about 0.4% w/w, or from about 0.025% w/w to about 0.035% w/w econazole or a pharmaceutically acceptable salt thereof.

In an aspect, a disclosed compounded composition comprising mupirocin, clindamycin or a salt thereof, gentamicin or a salt thereof, and econazole or a salt thereof can comprise from about 0.9% w/w to 1.0% w/w mupirocin, from about 0.04% w/w to about 0.06% w/w clindamycin or a pharmaceutically acceptable salt thereof, from about 0.01% w/w to about 0.03% w/w gentamicin or a pharmaceutically acceptable salt thereof, and from about 0.2% w/w to about 0.4% w/w econazole or a pharmaceutically acceptable salt thereof. In an aspect, a disclosed compounded composition can comprise about 0.9% w/w mupirocin, about 0.05% w/w clindamycin phosphate, about 0.02% w/w gentamicin sulfate, and about 0.3% w/w econazole nitrate.

Disclosed herein is a compounded composition comprising a therapeutically effective amount of doxycycline or a pharmaceutically acceptable salt thereof and a therapeutically effective amount of nystatin. A disclosed compounded composition comprising doxycycline or a salt thereof and nystatin can comprise a dry powder formulation or can comprise an ointment.

In an aspect, a disclosed compounded composition comprising doxycycline or a salt thereof and nystatin can comprise from about 1.0% w/w to about 10.0% w/w or from about 2.0% w/w to about 9.0% w/w doxycycline or a pharmaceutically acceptable salt thereof. In an aspect, a disclosed compounded composition comprising doxycycline or a salt thereof and nystatin can comprise about 3.0% w/w, about 4.0% w/w, about 5.0% w/w, about 6.0%, about 7.0% w/w, or about 8.0% w/w doxycycline or a pharmaceutically acceptable salt thereof. In an aspect, a disclosed compounded composition comprising doxycycline or a salt thereof and nystatin can comprise from about 50,000 to about 98,000 units per gram, from about 60,000 to about 90,000 units per gram, from about 70,000 to about 90,000 units per gram, or from about 80,000 to about 90,000 units per gram nystatin. In an aspect, a disclosed compounded composition comprising doxycycline or a salt thereof and nystatin can comprise from about 4.0% w/w to about 6.0% w/w doxycycline or a pharmaceutically acceptable salt thereof and from about 80,000 to about 90,000 units per gram nystatin. In an aspect, a disclosed compounded composition comprising doxycycline or a salt thereof and nystatin can comprise about 5.0% w/w doxycycline or a pharmaceutically acceptable salt thereof and about 87,825 units per gram nystatin.

Disclosed herein is a compounded composition comprising a therapeutically effective amount of tobramycin or a pharmaceutically acceptable salt thereof and a therapeutically effective amount of nystatin. A disclosed compounded composition comprising tobramycin or a salt thereof and nystatin can comprise a dry powder formulation or can comprise an ointment. In an aspect, a disclosed compounded composition comprising tobramycin or a salt thereof and nystatin can comprise from about 1.0% w/w to about 10.0% w/w or from about 2.0% w/w to about 9.0% w/w tobramycin or a pharmaceutically acceptable salt thereof. In an aspect, a disclosed compounded composition comprising tobramycin or a salt thereof and nystatin can comprise about 3.0% w/w, about 4.0% w/w, about 5.0% w/w, about 6.0%, about 7.0% w/w, or about 8.0% w/w tobramycin or a pharmaceutically acceptable salt thereof. In an aspect, a disclosed compounded composition comprising tobramycin or a salt thereof and nystatin can comprise from about 50,000 to about 98,000 units per gram, from about 60,000 to about 90,000 units per gram, from about 70,000 to about 90,000 units per gram, or from about 80,000 to about 90,000 units per gram nystatin. In an aspect, a disclosed compounded composition comprising tobramycin or a salt thereof and nystatin can comprise from about 4.0% w/w to about 6.0% w/w tobramycin or a pharmaceutically acceptable salt thereof and from about 80,000 to about 90,000 units per gram nystatin. In an aspect, a disclosed compounded composition comprising tobramycin or a salt thereof and nystatin can comprise about 5.0% tobramycin or a pharmaceutically acceptable salt thereof and about 87,825 units per gram nystatin.

Disclosed herein is a compounded composition comprising a therapeutically effective amount of clobetasol propionate and a therapeutically effective amount of fluconazole or urea. In an aspect, a disclosed compounded composition comprising clobetasol propionate and fluconazole or urea can comprise a dry powder formulation or can comprise an ointment.

In an aspect, a disclosed compounded composition comprising clobetasol propionate and fluconazole can comprise from about 0.02% w/w to about 0.10% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and fluconazole can comprise from about 1.0% w/w to about 5.0% w/w, from about 2.0% w/w to about 4.0% w/w, from about 2.0% w/w to about 3.0% w/w, or from about 2.0% w/w to about 4.0% w/w fluconazole. In an aspect, a disclosed compounded composition comprising clobetasol propionate and fluconazole can comprise from about 0.02% w/w to about 0.06% w/w clobetasol propionate and from about 2.0% w/w to about 4.0% w/w fluconazole. In an aspect, a disclosed compounded composition can comprise about 0.0485% w/w clobetasol propionate and about 3.0% w/w fluconazole. In an aspect, clobetasol propionate can comprise clobetasol propionate 0.05% ointment.

In an aspect, a disclosed compounded composition comprising clobetasol propionate and urea can comprise from about 0.02% w/w to about 0.10% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and urea can comprise from about 10.0% w/w to about 60.0% w/w, from about 20.0% w/w to about 50.0% w/w, from about 30.0% w/w to about 50.0% w/w, from about 30.0% w/w to about 40.0% w/w, or from about 40.0% w/w to about 50.0% w/w urea. In an aspect, a disclosed compounded composition comprising clobetasol propionate and urea can comprise from about 0.02% w/w to about 0.055% w/w clobetasol propionate and from about 30.0% w/w to about 50.0% w/w urea. In an aspect, a disclosed compounded composition comprising clobetasol propionate and urea can comprise about 0.03% w/w clobetasol propionate and about 40.0% w/w urea. In an aspect, clobetasol propionate can comprise clobetasol propionate 0.05% ointment.

Disclosed herein is a compounded composition comprising a therapeutically effective amount of clobetasol propionate and a therapeutically effective of amount of ketoconazole. A disclosed compounded composition can comprise a dry powder formulation or can comprise an ointment.

In an aspect, a disclosed compounded composition comprising clobetasol propionate and ketoconazole can comprise from about 0.02% w/w to about 0.1% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and ketoconazole can comprise from about 3.0% w/w to about 12.0% w/w, from about 4.0% w/w to about 10.0% w/w, from about 5% w/w to about 10% w/w, or from about 6.0% w/w to about 8.0% w/w ketoconazole. In an aspect, a disclosed compounded composition comprising clobetasol propionate and ketoconazole can comprise from about 0.04% w/w to about 0.05% w/w clobetasol propionate and from about 6.0% w/w to about 8.0% w/w ketoconazole. In an aspect, a disclosed compounded composition comprising clobetasol propionate and ketoconazole can comprise about 0.04% w/w clobetasol propionate and about 7.5% w/w ketoconazole. In an aspect, clobetasol propionate can comprise clobetasol propionate 0.05% ointment.

Disclosed herein is a compounded composition comprising a therapeutically effective amount of ketoconazole, a sufficient amount of an excipient base powder comprising a blend of micronized xylitol and poloxamers, and a sufficient amount of xylitol. A disclosed compounded composition can comprise a dry powder formulation or can comprise an ointment.

In an aspect, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. Excipient base powders are known to the art and discussed supra.

In an aspect, a disclosed compounded composition comprising ketoconazole, an excipient base powder, and xylitol can comprise from about 10.0% w/w to about 50.0% w/w, from about 20.0% w/w to about 40.0% w/w, or from about 25.0% w/w to about 35.0% w/w ketoconazole. In an aspect, a disclosed compounded composition comprising ketoconazole, an excipient base powder, and xylitol can comprise a weight ratio of excipient base powder to xylitol of about 1:1, about 1:2, about 1:3, about 1:4, about 1:5, about 1:6, about 1:7, from about 1:1 to about 1:7, from about 1:2 to about 1:6, or from about 1:4 to about 1:5. In an aspect, the weight ratio of excipient base powder to xylitol can be about 1:4.35. In an aspect, a disclosed compounded composition comprising ketoconazole, an excipient base powder, and xylitol can comprise about 30.0% w/w ketoconazole and a weight ratio of excipient base powder to xylitol of about 1:4 to about 1:5. In an aspect, a disclosed compounded composition comprising ketoconazole, an excipient base powder, and xylitol can comprise about 30.0% w/w ketoconazole and a weight ratio of excipient base powder to xylitol of about 1:4.35. In an aspect, a disclosed compounded composition comprising ketoconazole, LoxaSperse™, and xylitol can comprise about 30.0% w/w ketoconazole and a weight ratio of LoxaSperse™ to xylitol of about 1:4.35.

In an aspect, a disclosed compounded composition can comprise a therapeutically effective amount of one or more additional anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

7. Capsules

Disclosed herein is a capsule comprising a disclosed compounded composition. Capsules may include dry powder obtained from crushed tablets, bulk powders, antimicrobials for injection, or combinations thereof.

In an aspect, a disclosed capsule can comprise about 100 mg to about 2000 mg of a disclosed compounded composition. In an aspect, a disclosed capsule can comprise about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed compounded composition.

In an aspect, a disclosed capsule comprising a disclosed compounded composition can be broken apart such that its contents can be retrieved. In an aspect, a disclosed capsule can be dissolved in water such that its contents can be contacted with the water.

In an aspect, a disclosed capsule can comprise one or more additional anti-infective agents. In an aspect, the additional anti-infective agent can be a dry powder. In an aspect, the additional anti-infective agent can be an ointment. The additional anti-infective agent can be pure or substantially pure. The additional anti-infective agent can be obtained from a bulk source. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, a disclosed capsule can comprise one or more excipients or additives. In an aspect, excipients or additives include, but are not limited to, the following: solvents, surfactants, humectants, preservatives, flavorings, stabilizers (including antioxidants), binders, and colorants.

8. Kits Disclosed herein is kit, comprising: a plurality of containers, each container comprising a compounded composition.

In an aspect, the plurality of containers can comprise more than 1 container. In an aspect, the plurality can comprise at least 3 containers, at least 7 containers, or at least 10 containers, at least 14 containers, at least 21 containers, at least 30 containers, at least 60 containers, at least 90 containers, at least 120 containers, or at least 150 containers, or more than 150 containers.

In an aspect, the plurality of containers can comprise a 3 day's supply, or a week's supply, or a 10 day's supply, or a two week's supply, or a month's supply, or a two month's supply, or a three month's supply, or a six month's supply, or more than a six month's supply of a disclosed compounded composition.

In an aspect, a disclosed kit can comprise a footbath. Footbaths are known to the art and are discussed supra. In an aspect, a disclosed kit can comprise one or more funnels. In an aspect, a disclosed kit can comprise one or more mixing containers. In an aspect, a disclosed kit can comprise one or more scoops or spoons, such as a 5 cc scoop or spoon or a 1 cc scoop or spoon.

In an aspect, a disclosed kit can comprise one or more keys. In an aspect, a disclosed kit can comprise a diluent for a disclosed compounded composition. In an aspect, a diluent can comprise sodium hypochlorite. In an aspect, a diluent can comprise Dakin's solution. In an aspect, a disclosed kit can comprise one or more bottles of diluent.

In an aspect, a disclosed kit can comprise non-stick, hypo-allergenic tape, sterile pads, sterile applicators (e.g., sterile 6 inch applicators), or a combination thereof. In an aspect, a disclosed kit can comprise one or more bottles of a cleaning solution or suspension, such as a liquid skin cleanser. In an aspect, the cleaning solution or suspension can be Hibiclens.

In an aspect, the disclosed kit comprises a footbath starter pack. The footbath starter pack may be suitable for administering one or more of the compounded compositions described herein, e.g., footbath compositions and footbath solutions. In various aspects, the footbath starter pack includes a footbath, 1 to 2 bottle(s) of diluent, a funnel, a mixing container, and a measuring device for measuring powder medications, e.g., one or two spoons/scoops, such as those described above.

In one aspect, the compounded composition includes a compounded powder comprising about 25% (w/w) mupirocin and about 25% (w/w) itraconazole. The compounded powder may also include Loxasperse®-Xylifos™ Combination Powder, which may make up the remaining 50% of the compounded powder. A method of treating or preventing an infection, such as a foot infection, with such a composition using the footbath starter pack may comprise filling the footbath with warm water to a fill line indicated on the inside of the footbath. Using the funnel, adding 2 scoops of medication using a first spoon into the mixing container. For every tablespoon of powder, 15 ml of diluent may be added to the mixing container holding the powder. The mixture may then be mixed, e.g., by shaking or stirring. The footbath may then be turned on an water therein allowed to agitate. The solution/suspension mixture may then be added to the water. The subjects foot or portion thereof may be placed in the footbath for a suitable amount of time, such as 10 minutes, or other duration, such as described elsewhere herein. The footbath starter pack may be configured for use in administration of different compounded compositions and footbath compositions. For example, in one aspect, a footbath composition comprises mupirocin and itraconazole. The footbath compositions may comprises various rations of mupirocin to itraconazole, e.g., between about 1:9 and about 9:1, about 1:1, about 1:2, about 1:3, about 2:1, or about 3:1. A method of treating or preventing an infection, such as a foot infection, with such a composition using the footbath starter pack may comprise filling the footbath with warm water to a fill line indicated on the inside of the footbath. Using the funnel, adding 2 scoops of mupirocin powder using a second spoon, different from the first, and one scoop of itraconazole using the second spoon, may be added into the mixing container. For every tablespoon of powder, 15 ml of diluent may be added to the mixing container holding the powder. The mixture may then be mixed, e.g., by shaking or stirring. The footbath may then be turned on an water therein allowed to agitate. The solution/suspension mixture may then be added to the water. The subjects foot or portion thereof may be placed in the footbath for a suitable amount of time, such as 10 minutes, or other duration, such as described elsewhere herein.

In a further aspect, the compounded composition includes a compounded powder comprising azithromycin and fluconazole. In one example, the compounded composition includes a compounded powder comprising about 250 mg azithromycin and 200 mg fluconazole. A method of treating or preventing an infection, such as a foot infection, with such a composition using the footbath starter pack may comprise filling the footbath with warm water to a fill line indicated on the inside of the footbath. The method may further include opening one capsule and, using the plastic funnel, placing the entire contents of the capsule into the mixing container. For every tablespoon of powder, 15 ml of diluent may be added to the mixing container holding the powder. The mixture may then be mixed, e.g., by shaking or stirring. The footbath may then be turned on an water therein allowed to agitate. The solution/suspension mixture may then be added to the water. The subjects foot or portion thereof may be placed in the footbath for a suitable amount of time, such as 10 minutes, or other duration, such as described elsewhere herein.

In a further aspect, the footbath composition includes a combination ointment and powder. For example, in one aspect, the footbath composition comprises mupirocin 2% ointment and an antifungal agent, as disclosed herein. The antifungal agent may comprise, for example, one or more of ketoconazole, voriconazole, amphotericin, or nystatin. The antifungal agent may be a dry powder comprising crushed oral tablets, bulk powder, antifungal for injection, or combinations thereof. In one example, the antifungal agent includes nystatin topical powder. A method of treating or preventing an infection, such as a foot infection, with such a composition using the footbath starter pack may comprise filling the footbath with warm water to a fill line indicated on the inside of the footbath. The method may further include opening one bottle of nystatin 15 mg and placing the opening of the bottle into the neck of the mixing container and squeezing until all the powder is removed from the bottle. The method may further include opening one 22 g tube of mupirocin 2% ointment and sliding the metal key onto the end of the tube. The mouth of the mupirocin ointment tube may be positioned at the opening of the mixing container. Turning the key downward, the contents of the tube may be emptied into the mixing container. For every tablespoon of the footbath composition, 15 ml of diluent may be added to the mixing container holding the composition. The mixture may then be mixed, e.g., by shaking or stirring. The footbath may then be turned on an water therein allowed to agitate. The solution/suspension mixture may then be added to the water. The subjects foot or portion thereof may be placed in the footbath for a suitable amount of time, such as 10 minutes, or other duration, such as described elsewhere herein.

D. Methods of Making a Compounded Composition

Disclosed herein are methods of making a compounded composition.

1. A First Antibacterial Agent and a Second Antibacterial Agent

Disclosed herein is a method of making a compounded composition, the method comprising: mixing a therapeutically effective amount of a first antibacterial agent and a therapeutically effective amount of a second antibacterial agent to make a homogeneous compounded composition. A disclosed compounded composition can comprise a dry powder formulation or can comprise an ointment.

In an aspect, the mixing can comprise using an electronic mortar and pestle (EMP). In an aspect, a disclosed method can comprise milling the ingredients (using, for example, a three-roll mill). Mixing and milling can be done according to standards known to the skilled person in the art.

In an aspect, a disclosed method can comprise obtaining the first antibacterial agent, obtaining the second antibacterial agent, or a combination thereof. In an aspect, obtaining can comprise obtaining a bulk source of the first antibacterial agent, obtaining a bulk source of the second antibacterial agent, or a combination thereof.

Antibacterial agents are known to the art and are discussed supra.

In an aspect, a disclosed compounded composition comprising a first antibacterial agent and a second antibacterial agent can comprise from about 1.0% w/w to about 3.0% w/w of the first antibacterial agent. In an aspect, a disclosed compounded composition comprising a first antibacterial agent and a second antibacterial agent can comprise about 1.6% w/w, or about 1.7% w/w, or about 1.756% w/w, or about 1.77% w/w, or about 1.775% w/w, or about 1.8% w/w of the first antibacterial agent. In an aspect, a disclosed compounded composition comprising a first antibacterial agent and a second antibacterial agent can comprise from about 4.0% w/w to about 9.0% w/w or from about 6.0% w/w to about 8.0% w/w of the second antibacterial agent. In an aspect, a disclosed compounded composition comprising a first antibacterial agent and a second antibacterial agent comprise about 5.0% w/w or about 7.5% w/w of the second antibacterial agent.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

2. An Antibacterial Agent and an Antifungal Agent

Disclosed herein is a method of making a compounded composition, the method comprising: mixing a therapeutically effective amount of an antibacterial agent and a therapeutically effective amount of an antifungal agent to make a homogeneous compounded composition. A disclosed compounded composition can comprise a dry powder formulation or can comprise an ointment.

In an aspect, the mixing can comprise using an electronic mortar and pestle (EMP). In an aspect, a disclosed method can comprise milling the ingredients (using, for example, a three-roll mill). Mixing and milling can be done according to standards known to the skilled person in the art.

In an aspect, a disclosed method can comprise obtaining the antibacterial agent, obtaining the antifungal agent, or a combination thereof. In an aspect, obtaining can comprise obtaining a bulk source of one or more antibacterials of the antibacterial agent or obtaining a bulk source of one or more antifungals of the antifungal agent.

Antibacterial agents and antifungal agents are known to the art and are discussed supra.

In an aspect, a disclosed compounded composition comprising an antibacterial agent and an antifungal agent can comprise from about 1.0% w/w to about 3.0% w/w of the antibacterial agent. In an aspect, a disclosed compounded composition comprising an antibacterial agent and an antifungal agent can comprise about 1.6% w/w, or about 1.626 w/w, or about 1.7% w/w, or about 1.71% w/w, or about 1.756% w/w, or about 1.77% w/w, or about 1.775% w/w, or about 1.8% w/w of the antibacterial agent. In an aspect, a disclosed compounded composition comprising an antibacterial agent and an antifungal agent can comprise from about 2.0% w/w to about 9.0% w/w or from about 3.0% w/w to about 8.0% w/w of the antifungal agent. In various embodiments, first antibacterial comprises about 1% to about 1.9% w/w mupirocin and the antifungal comprises from about 0.2% to about 6% w/w voriconazole. In one example, the compounded composition comprises about 1.71% w/w mupirocin and 0.8% w/w voriconazole. The mupirocin may be mupirocin 2% ointment in an amount approximately 85.7% w/w of the compounded composition and the voriconazole may include voriconazole for injection in an amount about 0.8% w/w of the compounded composition.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

3. A First Antibacterial Agent, a Second Antibacterial Agent, and an Antifungal Agent Disclosed herein is a method of making a compounded composition, the method comprising: mixing a therapeutically effective amount of a first antibacterial agent, a therapeutically effective amount of a second antibacterial agent, and a therapeutically effective amount of an antifungal agent to make a homogeneous compounded composition. A disclosed compounded composition can comprise a dry powder formulation or can comprise an ointment.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art.

In an aspect, a disclosed method can comprise obtaining the first antibacterial agent, obtaining the second antibacterial agent, obtaining the antifungal agent, or a combination thereof. In an aspect, obtaining can comprise obtaining a bulk source of the first antibacterial agent, obtaining a bulk source of the second antibacterial agent, obtaining a bulk source of the antifungal agent, or a combination thereof.

Antibacterial agents are known to the art and are discussed supra. Antifungal agents are known to the art and are discussed supra.

In an aspect, a disclosed compounded composition comprising a first antibacterial agent, a second antibacterial agent, and an antifungal agent can comprise from about 1.0% w/w to about 3.0% w/w of the first antibacterial agent. In an aspect, a disclosed compounded composition comprising a first antibacterial agent, a second antibacterial agent, and an antifungal agent can comprise about 1.6% w/w, or about 1.756% w/w, or about 1.77% w/w, or about 1.775% w/w, or about 1.8% w/w of the first antibacterial agent. In an aspect, a disclosed compounded composition comprising a first antibacterial agent, a second antibacterial agent, and an antifungal agent can comprise from about 2.0% w/w to about 9.0% w/w or from about 3.0% w/w to about 8.0% w/w of the second antibacterial agent. In an aspect, a disclosed compounded composition comprising a first antibacterial agent, a second antibacterial agent, and an antifungal agent can comprise about 2.5% w/w, about 5.0% w/w, or about 7.5% w/w of the second antibacterial agent. In an aspect, a disclosed compounded composition comprising a first antibacterial agent, a second antibacterial agent, and an antifungal agent can comprise from about 2.0% w/w to about 9.0% w/w or from about 3.0% w/w to about 8.0% w/w of the antifungal agent. In an aspect, a disclosed compounded composition comprising a first antibacterial agent, a second antibacterial agent, and an antifungal agent can comprise about 2.5% w/w, about 5.0% w/w, or about 7.5% w/w of the antifungal agent.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin. In one example, the compounded composition comprises about 1.6% w/w mupirocin, about 0.8% w/w voriconazole, and about 4% w/w streptomycin. The mupirocin may be mupirocin 2% ointment in an amount approximately 80% w/w of the compounded composition, the voriconazole may include voriconazole for injection in an amount about 0.8% w/w of the compounded composition, and the streptomycin may comprise streptomycin sulfate for injection in an amount about 5.528% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin and about 0.2% to about 6% doxycycline. In one example, the compounded composition comprises about 1.55% w/w mupirocin, about 0.8% w/w voriconazole, about 4% w/w streptomycin, and about 1% w/w doxycycline. The mupirocin may be mupirocin 2% ointment in an amount approximately 77.6% w/w of the compounded composition, the voriconazole may include voriconazole for injection in an amount about 0.8% w/w of the compounded composition, the streptomycin may comprise streptomycin sulfate for injection in an amount about 5.528% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w tobramycin and about 0.2% to about 6% doxycycline. In one example, the compounded composition comprises about 1.62% w/w mupirocin, about 0.8% w/w voriconazole, about 1.2% w/w tobramycin, and about 1% w/w doxycycline. The mupirocin may be mupirocin 2% ointment in an amount approximately 81.3% w/w of the compounded composition, the voriconazole may include voriconazole for injection in an amount about 0.8% w/w of the compounded composition, the tobramycin may comprise tobramycin sulfate for injection in an amount about 1.8% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w ketoconazole, and the second antibacterial comprises from about 0.2% to about 6% w/w streptomycin and about 0.2% to about 6% doxycycline. In one example, the compounded composition comprises about 1.71% w/w mupirocin, about 2% w/w ketoconazole, about 4% w/w streptomycin, and about 2% w/w doxycycline. The mupirocin may be mupirocin 2% ointment in an amount approximately 85.7% w/w of the compounded composition, the ketoconazole may include ketoconazole 200 mg tablets in an amount about 3.875% w/w of the compounded composition, the streptomycin may comprise streptomycin sulfate for injection in an amount about 5.528% w/w of the compounded composition, and the doxycycline may comprise doxycycline hyclate 100 mg tablets in an amount about 4.87% w/w of the compounded composition.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising a first antibacterial agent, a second antibacterial agent, and an antifungal agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising a first antibacterial agent, a second antibacterial agent, and an antifungal agent.

4. Mupirocin and an Antibacterial Agent

Disclosed herein is a method of making a compounded composition, the method comprising: mixing a therapeutically effective amount of mupirocin and a therapeutically effective amount of an antibacterial agent to make a homogeneous compounded composition. A disclosed compounded composition can comprise a dry powder formulation or can comprise an ointment.

In an aspect, a disclosed method can comprise obtaining the mupirocin, obtaining the antibacterial agent, or a combination thereof. In an aspect, obtaining can comprise obtaining a bulk source of the mupirocin, obtaining a bulk source of the antibacterial agent, or a combination thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art.

Mupirocin is known to the art and is discussed supra. Antibacterial agents are known to the art and are discussed supra.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.756% w/w, or about 1.77% w/w, or about 1.775% w/w, or about 1.8% w/w mupirocin. In an aspect, a disclosed compounded composition comprising mupirocin and an antibacterial agent can comprise from about 4.0% w/w to about 9.0% w/w or from about 6.0% w/w to about 8.0% w/w of the antibacterial agent. In an aspect, a disclosed compounded composition comprising mupirocin and an antibacterial agent can comprise about 5.0% w/w or about 7.5% w/w of the antibacterial agent.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and an antibacterial agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and an antibacterial agent.

Mupirocin and Tobramycin or a Salt Thereof

Disclosed herein is a method of making a compounded composition, the method comprising: mixing a therapeutically effective amount of mupirocin and a therapeutically effective amount of tobramycin or a pharmaceutically acceptable salt thereof to make a homogeneous compounded composition. A disclosed compounded composition can comprise a dry powder formulation or can comprise an ointment.

In an aspect, a disclosed method can comprise obtaining the mupirocin, obtaining the tobramycin or a pharmaceutically acceptable salt thereof, or a combination thereof. In an aspect, obtaining can comprise obtaining a bulk source of the mupirocin, obtaining a bulk source of the tobramycin or a pharmaceutically acceptable salt thereof, or a combination thereof.

Mupirocin is known to the art and is discussed supra. Tobramycin as well as pharmaceutically acceptable salts thereof are known to the art and are discussed supra.

In an aspect, a disclosed compounded composition comprising mupirocin and tobramycin or a salt thereof can comprise from about 1.0% w/w to about 3.0% w/w mupirocin. In an aspect, a disclosed compounded composition comprising mupirocin and tobramycin or a salt thereof can comprise about 1.775% w/w mupirocin. In an aspect, a disclosed compounded composition comprising mupirocin and tobramycin or a salt thereof can comprise from about 7.0% to about 9.0% w/w of tobramycin or a pharmaceutically acceptable salt thereof. In an aspect, a disclosed compounded composition comprising mupirocin and tobramycin or a salt thereof can comprise about 7.5% w/w of tobramycin or a pharmaceutically acceptable salt thereof. In an aspect, a disclosed compounded composition comprising mupirocin and tobramycin or a salt thereof can comprise about 1.775% w/w mupirocin and about 7.5% w/w tobramycin or a pharmaceutically acceptable salt thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and tobramycin or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting.

Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 1

In an aspect, to make 1 g of the compounded composition, which has about 1.775% w/w mupirocin and about 7.5% w/w tobramycin sulfate, about 0.8875 g of mupirocin 2.0% ointment and about 0.1125 g of tobramycin sulfate for injection USP powder can be combined and mixed together according to a method described above.

Table 1 provides the approximate amount of mupirocin and tobramycin sulfate needed to make various amounts of the compounded composition.

TABLE 1

MUPIROCIN AND TOBRAMYCIN SULFATE

| Compounded Composition (in grams) | Mupirocin (2.0% ointment) | Tobramycin Sulfate (for injection USP |
|---|---|---|
| 1 | 0.8875 g | 0.1125 g |
| 4 | 3.55 g | 0.45 g |
| 8 | 7.1 g | 0.90 g |
| 25 | 22.1875 g | 2.8125 g |
| 50 | 44.375 g | 5.625 g |
| 240 | 213.0 g | 27.0 g |
| 1500 | 1331.25 g | 168.75 g |

As used in Example 1, the term "about" means a value falling within a range that is ±10% of the stated value. In an aspect, the skilled person can combine 0.8875 g±10% mupirocin 2.0% ointment (e.g., from about 0.79875 g-0.97625 g) and 0.1125 g±10% tobramycin sulfate for injection USP powder (e.g., from about 0.10125 g-0.12375 g) and mix together according to a method described above to make about 1.0 g±10% of the compounded composition.

Example 2

In an aspect, to make 1 g of the compounded composition, which has about 1.775% w/w mupirocin and about 7.5% w/w tobramycin, about 0.925 g of mupirocin 2.0% ointment and about 0.075 g of pure or substantially pure tobramycin powder can be combined and mixed together according to a method described above.

Table 2 provides the approximate amount of mupirocin and pure or substantially pure tobramycin needed to make various amounts of the compounded composition.

TABLE 2

MUPIROCIN AND PURE OR SUBSTANTIALLY PURE TOBRAMYCIN

| Compounded Composition (in grams) | Mupirocin (2.0% ointment) | Tobramycin (pure/substantially pure dry |
|---|---|---|
| 1 | 0.925 g | 0.075 g |
| 4 | 3.7 g | 0.3 g |
| 8 | 7.4 g | 0.6 g |
| 25 | 23.125 g | 1.875 g |
| 50 | 46.25 g | 3.75 g |
| 240 | 222.0 g | 18.0 g |
| 1500 | 1387.5 g | 112.5 g |

As used in Example 2, the term "about" means a value falling within a range that is ±10% of the stated value. In an aspect, the skilled person can combine 0.925 g±10% mupirocin 2.0% ointment (e.g., from about 0.8325 g-1.0175 g) and 0.075 g±10% pure or substantially pure dry tobramycin powder (e.g., from about 0.0675 g-0.0825 g and mix together according to a method described above to make about 1.0 g±10% of the compounded composition.

Mupirocin and Doxycycline or a Salt Thereof

Disclosed herein is a method of making a compounded composition, the method comprising: mixing a therapeutically effective amount of mupirocin and a therapeutically effective amount of doxycycline or a pharmaceutically acceptable salt thereof to make a homogeneous compounded composition. A disclosed compounded composition can comprise a dry powder formulation or can comprise an ointment.

In an aspect, a disclosed method can comprise obtaining the mupirocin, obtaining the doxycycline or a pharmaceutically acceptable salt thereof, or a combination thereof. In an aspect, obtaining can comprise obtaining a bulk source of the mupirocin, obtaining a bulk source of the doxycycline or a pharmaceutically acceptable salt thereof, or a combination thereof.

Mupirocin is known to the art and is discussed supra. Doxycycline as well as pharmaceutically acceptable salts thereof are known to the art and are discussed supra.

In an aspect, a disclosed compounded composition comprising mupirocin and doxycycline or a salt thereof can comprise from about 1.0% w/w to about 3.0% w/w mupirocin. In an aspect, a disclosed compounded composition comprising mupirocin and doxycycline or a salt thereof can comprise about 1.756% w/w mupirocin. In an aspect, a disclosed compounded composition comprising mupirocin and doxycycline or a salt thereof can comprise from about 4.0% to about 6.0% w/w doxycycline or a pharmaceutically acceptable salt thereof. In an aspect, a disclosed compounded composition comprising mupirocin and doxycycline or a salt thereof can comprise about 5.0% w/w doxycycline or a pharmaceutically acceptable salt thereof. In an aspect, a disclosed compounded composition comprising mupirocin and doxycycline or a salt thereof can comprise about 1.756% w/w mupirocin and about 5.0% w/w doxycycline or a pharmaceutically acceptable salt thereof.

In an aspect, the formula presented below can be used to identify the approximate amount of powder from crushed doxycycline hyclate tablets needed for 1 g of the compounded composition:

0.878.8

In an aspect, the average weight of a doxycycline hyclate tablet can be about 0.2435 g and can comprise about 100 mg of doxycycline. In an aspect, using the above-identified formula, the amount of powder from crushed doxycycline hyclate tablets can be determined to be about 0.12175 g (or 121.75 mg).

$$\underset{(0.2435 \text{ g})}{\text{average tablet weight}} \times \underset{(50\%)}{x\% \text{ of a tablet needed}} = \underset{(0.12175 \text{ g})}{\text{amount of powder from crushed tablets needed}}$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and doxycycline or a salt thereof into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and doxycycline or a salt thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and doxycycline or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 3

In an aspect, to make 1 g of the compounded composition, which has about 5.0% mupirocin and about 1.756% doxycycline or a pharmaceutically acceptable salt thereof, about 0.8782 g of mupirocin 2.0% ointment and about 0.12175 g of powder from crushed doxycycline hyclate tablets can be combined and mixed together according to a method described above.

Table 3 provides the approximate amount of mupirocin and doxycycline hyclate needed to make various amounts of the compounded composition.

TABLE 3

MUPIROCIN AND DOXYCYCLINE HYCLATE

| Compounded Composition (in grams) | Mupirocin (2.0% ointment) | Doxycycline Hyclate (powder from crushed |
|---|---|---|
| 1 | 0.8782 g | 0.12175 g |
| 4 | 3.5128 g | 0.487 g |
| 8 | 7.0256 g | 0.974 g |
| 25 | 21.955 g | 3.04375 g |
| 50 | 43.91 g | 6.0875 g |
| 240 | 210.768 g | 29.22 g |
| 1500 | 1317.3 g | 182.625 g |

As used in Example 3, the term "about" means a value falling within a range that is ±10% of the stated value. In an aspect, the skilled person can combine 0.8782 g±10% mupirocin 2.0% ointment (e.g., from about 0.79038 g-0.96602 g) and 0.12175 g±10% powder from crushed doxycycline hyclate tablets (e.g., from about 0.109575 g-0.133925 g) and mix together according to a method described above to make about 1.0 g±10% of the compounded composition.

Example 4

In an aspect, to make 1 g of the compounded composition, which has about 5.0% mupirocin and about 1.756% doxycycline, about 0.950 g of mupirocin 2.0% ointment and about 0.050 g of pure or substantially pure doxycycline powder can be combined and mixed together according to a method described above.

Table 4 provides the approximate amount of mupirocin and pure or substantially pure doxycycline needed to make various amounts of the compounded composition.

TABLE 4

MUPIROCIN AND PURE OR SUBSTANTIALLY PURE DOXYCYCLINE

| Compounded Composition (in grams) | Mupirocin (2.0% ointment) | Doxycycline (pure/substantially pure dry |
|---|---|---|
| 1 | 0.950 g | 0.050 g |
| 4 | 3.8 g | 0.2 g |
| 8 | 7.6 g | 0.4 g |
| 25 | 23.75 g | 1.25 g |
| 50 | 47.5 g | 2.5 g |
| 240 | 228.0 g | 12.0 g |
| 1500 | 1425.0 g | 75.0 g |

As used in Example 4, the term "about" means a value falling within a range that is ±10% of the stated value. In an aspect, the skilled person can combine 0.950 g±10% mupirocin 2.0% ointment (e.g., from about 0.855 g-1.045 g) and 0.050 g±10% pure or substantially pure doxycycline dry powder (e.g., from about 0.045 g-0.055 g) and mix together according to a method described above to make about 1.0 g±10% of the compounded composition.

Mupirocin and Azithromycin

A method of making a compounded composition, the method comprising: mixing a therapeutically effective amount of mupirocin and a therapeutically effective amount of azithromycin to make a homogeneous compounded composition. A disclosed compounded composition can comprise a dry powder formulation or can comprise an ointment.

In an aspect, a disclosed method can comprise obtaining the mupirocin, obtaining the azithromycin, or a combination thereof. In an aspect, obtaining can comprise obtaining a bulk source of the mupirocin, obtaining a bulk source of the azithromycin, or a combination thereof.

Mupirocin is known to the art and is discussed supra. Azithromycin is known to the art and is discussed supra.

In an aspect, a disclosed compounded composition comprising mupirocin and azithromycin can comprise from about 1.0% w/w to about 3.0% w/w mupirocin. In an aspect, a disclosed compounded composition comprising mupirocin and azithromycin can comprise about 1.8% w/w mupirocin. In an aspect, a disclosed compounded composition comprising mupirocin and azithromycin can comprise from about 4.0% w/w to about 6.0% w/w azithromycin. In an aspect, a disclosed compounded composition comprising mupirocin and azithromycin can comprise about 5.0% w/w azithromycin. In an aspect, a disclosed compounded composition comprising mupirocin and azithromycin can comprise about 1.8% w/w mupirocin and about 5.0% w/w azithromycin.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including anti-oxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and azithromycin into a container and sealing the container. In an aspect, a container can be a container disclosed herein. In an aspect, a disclosed method can comprise sterilizing the compounded composition comprising mupirocin and azithromycin.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and azithromycin can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 5

In an aspect, to make 1 g of the compounded composition, which has about 1.8% w/w mupirocin and about 5.0% w/w azithromycin, about 0.9 g of mupirocin 2.0% ointment and about 0.10 g of azithromycin for injection USP powder (500 mg azithromycin/1 g powder) can be combined and mixed together according to a method described above.

Table 5 provides the approximate amount of mupirocin and azithromycin needed to make various amounts of the compounded composition.

TABLE 5

MUPIROCIN AND AZITHROMYCIN

| Compounded Composition (in grams) | Mupirocin (2.0% ointment) | Azithromycin (500 mg/1 g powder for |
|---|---|---|
| 1 | 0.9 g | 0.10 g |
| 4 | 3.6 g | 0.40 g |
| 8 | 7.2 g | 0.80 g |
| 25 | 22.5 g | 2.5 g |
| 50 | 45.0 g | 5.0 g |
| 240 | 216.0 g | 24.0 g |
| 1500 | 1350.0 g | 150.0 g |

As used in Example 5, the term "about" means a value falling within a range that is ±10% of the stated value. In an aspect, the skilled person can combine 0.90 g±10% mupirocin 2.0% ointment (e.g., from about 0.81 g-0.99 g) and 0.10 g±10% azithromycin powder for injection USP (e.g., from about 0.09 g-0.11 g) and mix together according to a method described above to make about 1.0 g±10% of the compounded composition.

Mupirocin and Ciprofloxacin or a Salt Thereof

Disclosed herein is a method of making a compounded composition, the method comprising: mixing a therapeutically effective amount of mupirocin and a therapeutically effective amount of ciprofloxacin or a pharmaceutically acceptable salt thereof to make a homogeneous compounded composition. A disclosed compounded composition can comprise a dry powder formulation or can comprise an ointment.

In an aspect, a disclosed method can comprise obtaining the mupirocin, obtaining the ciprofloxacin or a pharmaceutically acceptable salt thereof, or a combination thereof. In an aspect, obtaining can comprise obtaining a bulk source of the mupirocin, obtaining a bulk source of ciprofloxacin or a pharmaceutically acceptable salt thereof, or a combination thereof.

Mupirocin is known to the art and is discussed supra. Ciprofloxacin as well as pharmaceutically acceptable salts thereof are known to the art and are discussed supra.

In an aspect, a disclosed compounded composition comprising mupirocin and ciprofloxacin or salt thereof can comprise from about 1.0% w/w to about 3.0% w/w, from about 1.2% w/w to about 2.5% w/w, from about 1.4% w/w to about 2.3% w/w, from about 1.4% w/w to about 2.2% w/w, from about 1.5% w/w to about 2.1% w/w, from about 1.6% w/w to about 2.0% w/w, from about 1.7% w/w to about 2.0% w/w, or from about 1.8% w/w to about 2.0% w/w mupirocin. In an aspect, a disclosed compounded composition comprising mupirocin and ciprofloxacin or salt thereof can comprise from about 1.0% w/w to about 5.0% w/w, from about 1.0% w/w to about 3.0% w/w, or from about 1.5% w/w to about 2.5% w/w ciprofloxacin or a pharmaceutically acceptable thereof. In an aspect, a disclosed compounded composition comprising mupirocin and ciprofloxacin or salt thereof can comprise from about 1.8% w/w to about 2.0% w/w mupirocin and from about 1.0% w/w to about 3.0% w/w ciprofloxacin or a pharmaceutically acceptable thereof. In an aspect, a disclosed compounded composition comprising mupirocin and ciprofloxacin or salt thereof can comprise about 1.95% w/w mupirocin and about 2.0% w/w ciprofloxacin or a pharmaceutically acceptable salt thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and ciprofloxacin or salt thereof into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and ciprofloxacin or salt thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and ciprofloxacin or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 6

In an aspect, to make 1 g of the compounded composition, which has about 1.95% w/w mupirocin and about 2.0% w/w ciprofloxacin, about 0.9767 g of mupirocin 2.0% ointment and about 0.023288 g of ciprofloxacin HCl USP monohydrate can be combined and mixed together according to a method described above.

Table 6 provides the approximate amount of mupirocin and ciprofloxacin hydrochloride needed to make various amounts of the compounded composition.

TABLE 6

MUPIROCIN AND CIPROFLOXACIN HYDROCHLORIDE

| Compounded Composition (in grams) | Mupirocin (2.0% ointment) | Ciprofloxacin HCl (USP monohydrate) |
| --- | --- | --- |
| 1 | 0.9767 g | 0.023288 g |
| 4 | 3.9068 g | 0.093152 g |
| 8 | 7.8136 g | 0.186304 g |
| 25 | 24.4175 g | 0.5822 g |
| 50 | 48.835 g | 1.1644 g |
| 240 | 234.408 g | 5.58912 g |
| 1500 | 1465.05 g | 34.932 g |

As used in Example 6, the term "about" means a value falling within a range that is ±10% of the stated value. In an aspect, the skilled person can combine 0.9767 g±10% mupirocin 2.0% ointment (e.g., from about 0.87903 g-1.07437 g) and 0.02328 g±10% ciprofloxacin HCl monohydrate powder (e.g., from about 0.02095 g-0.025616 g) and mix together according to a method described above to make about 1.0 g±10% of the compounded composition.

Mupirocin and Clindamycin or a Salt Thereof

Disclosed herein is method of making a compounded composition, the method comprising: mixing a therapeutically effective amount of mupirocin and a therapeutically effective amount of clindamycin or a pharmaceutically acceptable salt thereof to make a homogenous compounded composition. A disclosed compounded composition can comprise a dry powder formulation or can comprise an ointment.

In an aspect, a disclosed method can comprise obtaining the mupirocin, obtaining the clindamycin or a pharmaceutically acceptable salt thereof, or a combination thereof. In an aspect, obtaining can comprise obtaining a bulk source of the mupirocin, obtaining a bulk source of the clindamycin or a pharmaceutically acceptable salt thereof, or a combination thereof.

In an aspect, a disclosed compounded composition comprising mupirocin and clindamycin or a salt thereof can comprise from about 1.0% w/w to about 3.0% w/w mupirocin. In an aspect, a disclosed compounded composition comprising mupirocin and clindamycin or a salt thereof can comprise about 1.88% w/w mupirocin. In an aspect, a disclosed compounded composition comprising mupirocin and clindamycin or a salt thereof can comprise from about 4.0% to about 6.0% w/w clindamycin or a pharmaceutically acceptable salt thereof. In an aspect, a disclosed compounded composition comprising mupirocin and clindamycin or a salt thereof can comprise about 5.0% w/w clindamycin or a pharmaceutically acceptable salt thereof. In an aspect, a disclosed compounded composition comprising mupirocin and clindamycin or a salt thereof can comprise about 1.88% w/w mupirocin and about 5.0% w/w clindamycin or a pharmaceutically acceptable salt thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and clindamycin or a salt thereof into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and clindamycin or a salt thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and clindamycin or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 7

In an aspect, to make about 1.0 g of the compounded composition, which has about 1.88% mupirocin and about 5.0% clindamycin or a pharmaceutically acceptable salt thereof, about 0.940 g of mupirocin 2.0% ointment and about 0.050 g of clindamycin hydrochloride USP powder be combined and mixed together according to a method described above.

Table 7 provides the approximate amount of mupirocin and clindamycin hydrochloride needed to make various amounts of the compounded composition.

TABLE 7

MUPIROCIN AND CLINDAMYCIN HYDROCHLORIDE

| Compounded Composition (in grams) | Mupirocin (2.0% ointment) | Clindamycin HCl (USP powder) |
| --- | --- | --- |
| ~1 | 0.94 g | 0.050 g |
| ~4 | 3.8 g | 0.20 g |
| ~8 | 7.6 g | 0.40 g |
| ~25 | 23.75 g | 1.25 g |
| ~50 | 47.5 g | 2.5 g |
| ~240 | 228.0 g | 12.0 g |
| ~1500 | 1425.0 g | 75.0 g |

As used in Example 7, the term "about" means a value falling within a range that is ±10% of the stated value. In an aspect, the skilled person can combine 0.95 g±10% mupirocin 2.0% ointment (e.g., from about 0.855 g-1.045 g) and 0.05 g±10% clindamycin HCl powder USP (e.g., from about 0.045 g-0.055 g) and mix together according to a method described above to make about 1.0 g±10% of the compounded composition.

5. Mupirocin and an Antifungal Agent

Disclosed herein is a method of making a compounded composition, the method comprising: mixing a therapeutically effective amount of mupirocin and a therapeutically effective amount of an antifungal agent to make a homogeneous compounded composition. A disclosed compounded composition can comprise a dry powder formulation or can comprise an ointment.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise obtaining the mupirocin, obtaining the antifungal agent, or a combination thereof. In an aspect, obtaining can comprise obtaining a bulk source of the mupirocin, obtaining a bulk source of the antifungal agent, or a combination thereof.

Mupirocin is known to the art and is discussed supra. Antifungal agents are known to the art and are discussed supra.

In an aspect, a disclosed compounded composition comprising mupirocin and an antifungal agent can comprise from about 1.0% w/w to about 3.0% w/w of the mupirocin. In an aspect, a disclosed compounded composition comprising mupirocin and an antifungal agent can comprise about 1.6% w/w, or about 1.756% w/w, or about 1.77% w/w, or about 1.775% w/w, or about 1.8% w/w of the mupirocin. In an aspect, a disclosed compounded composition comprising mupirocin and an antifungal agent from about 4.0% w/w to about 9.0% w/w or from about 6.0% w/w to about 8.0% w/w of the antifungal agent. In an aspect, a disclosed compounded composition comprising mupirocin and an antifungal agent can comprise about 2.5% w/w, about 5.0% w/w, or about 7.5% w/w of the antifungal agent.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and an antifungal agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and an antifungal agent.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art.

Mupirocin and Ketoconazole

Disclosed herein is a method of making a compounded composition, the method comprising: mixing a therapeutically effective amount of mupirocin and a therapeutically effective amount of ketoconazole to make a homogeneous compounded composition. A disclosed compounded composition can comprise a dry powder formulation or can comprise an ointment.

In an aspect, a disclosed method can comprise obtaining the mupirocin, obtaining the ketoconazole, or a combination thereof. In an aspect, obtaining can comprise obtaining a bulk source of the mupirocin, obtaining a bulk source of ketoconazole, or a combination thereof.

Mupirocin is known to the art and is discussed supra. Ketoconazole is known to the art and is discussed supra.

In an aspect, a disclosed compounded composition comprising mupirocin and ketoconazole can comprise from about 1.0% w/w to about 3.0% w/w mupirocin. In an aspect, a disclosed compounded composition comprising mupirocin and ketoconazole can comprise about 1.77% w/w mupirocin. In an aspect, a disclosed compounded composition comprising mupirocin and ketoconazole can comprise from about 6.5% w/w to about 8.5% w/w ketoconazole. In an aspect, a disclosed compounded composition comprising mupirocin and ketoconazole can comprise about 7.5% w/w ketoconazole. In an aspect, a disclosed compounded composition comprising mupirocin and ketoconazole can comprise about 1.77% w/w mupirocin and about 7.5% w/w ketoconazole.

The formula presented below can be used to identify the identify the approximate amount of powder from crushed ketoconazole tablets needed for 1 gram of the compounded composition:

avg. tablet weight (g) x % of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets can be determined to be about 0.11625 g (or 116.25 mg).

average tablet weight $x\%$ of a tablet needed = amount of powder from crushed tablets needed (0.310 g)   (37.5%)   (0.11625 g)

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 8

In an aspect, to make 1 g of the compounded composition, which has about 1.77% w/w mupirocin and about 7.5% w/w ketoconazole, about 0.8838 g of mupirocin 2.0% ointment and about 0.11625 g of powder from crushed ketoconazole tablets can be combined and mixed together according to a method described above.

Table 8 provides the approximate amount of mupirocin and ketoconazole needed to make various amounts of the compounded composition.

TABLE 8

MUPIROCIN AND KETOCONAZOLE

| Compounded Composition (in grams) | Mupirocin (2.0% ointment) | Ketoconazole (powder from crushed |
|---|---|---|
| 1 | 0.8838 g | 0.11625 g |
| 4 | 3.5352 g | 0.465 g |
| 8 | 7.0704 g | 0.93 g |
| 25 | 22.095 g | 2.90625 g |
| 50 | 44.19 g | 5.8125 g |
| 240 | 212.112 g | 27.9 g |
| 1500 | 1325.7 g | 174.375 g |

As used in Example 8, the term "about" means a value falling within a range that is ±10% of the stated value. In an aspect, the skilled person can combine 0.8838 g±10% mupirocin 2.0% ointment (e.g., from about 0.79542 g-0.97218 g) and 0.11625 g±10% powder from crushed ketoconazole tablets (e.g., from about 0.104625 g-0.127875 g) and mix together according to a method described above to make about 1.0 g±10% of the compounded composition.

Mupirocin and Nystatin

Disclosed herein is method of making a compounded composition, the method comprising: mixing a therapeutically effective amount of mupirocin and a therapeutically effective amount of nystatin to make a homogeneous compounded composition. A disclosed compounded composition can comprise a dry powder formulation or can comprise an ointment.

In an aspect, a disclosed method can comprise obtaining the mupirocin, obtaining the nystatin powder, or a combination thereof. In an aspect, obtaining can comprise obtaining a bulk source of the mupirocin, obtaining a bulk source of the nystatin powder, or a combination thereof.

Mupirocin is known to the art and is discussed supra. Nystatin is known to the art and is discussed supra.

In an aspect, a disclosed compounded composition comprising mupirocin and nystatin can comprise from about 1.0% w/w to about 3.0% w/w mupirocin. In an aspect, a disclosed compounded composition comprising mupirocin and nystatin can comprise about 1.60% w/w mupirocin. In an aspect, a disclosed compounded composition comprising mupirocin and nystatin can comprise from about 15,000 units per gram to about 25,000 units per gram nystatin. In an aspect, a disclosed compounded composition comprising mupirocin and nystatin can comprise about 20,000 units per gram nystatin. In an aspect, a disclosed compounded composition comprising mupirocin and nystatin can comprise about 1.60% w/w mupirocin and about 20,000 units per gram nystatin.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition mupirocin and nystatin into a container and sealing the container. In an aspect, a container can be a container disclosed herein, such as, for example, a plastic tube, a glass or non-glass vial, a syringe, etc. In an aspect, a disclosed method can comprise sterilizing the compounded composition mupirocin and nystatin.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and nystatin can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 9

In an aspect, to make 1 g of the compounded composition, which has about 1.6% w/w mupirocin and about 20,000 units/g nystatin, about 0.80 g of mupirocin 2.0% ointment and about 0.20 g of nystatin powder (100,000 units/g) can be combined and mixed together according to a method described above.

Table 9 provides the approximate amount of mupirocin and nystatin needed to make various amounts of the compounded composition.

TABLE 9

MUPIROCIN AND NYSTATIN

| Compounded Composition (in grams) | Mupirocin (2.0% ointment) | Nystatin Powder (100,000 units/ |
|---|---|---|
| 1 | 0.80 g | 0.20 g |
| 4 | 3.2 g | 0.80 g |
| 8 | 6.4 g | 1.6 g |
| 25 | 20.0 g | 5.0 g |
| 50 | 40.0 g | 10.0 g |

TABLE 9-continued

MUPIROCIN AND NYSTATIN

| Compounded Composition (in grams) | Mupirocin (2.0% ointment) | Nystatin Powder (100,000 units/ |
|---|---|---|
| 240 | 192.0 g | 48.0 g |
| 1500 | 1200.0 g | 300.0 g |

As used in Example 9, the term "about" means a value falling within a range that is ±10% of the stated value. In an aspect, the skilled person can combine 0.80 g±10% mupirocin 2.0% ointment (e.g., from about 0.72 g-0.88 g) and 0.20 g±10% nystatin (e.g., from about 0.18 g-0.22 g) and mix together according to a method described above to make about 1.0 g±10% of the compounded composition.

6. Mupirocin, an Antibacterial Agent, and an Antifungal Agent

Disclosed herein is a method of making a compounded composition, the method comprising: mixing a therapeutically effective amount of mupirocin, a therapeutically effective amount of an antibacterial agent, and a therapeutically effective amount of an antifungal agent to make a homogeneous compounded composition. A disclosed compounded composition can comprise a dry powder formulation or can comprise an ointment.

In an aspect, a disclosed method can comprise obtaining the mupirocin, obtaining the antibacterial agent, obtaining the antifungal agent, or a combination thereof. In an aspect, obtaining can comprise obtaining a bulk source of the mupirocin, obtaining a bulk source of the antibacterial agent, obtaining a bulk source of the antifungal agent, or a combination thereof. In an aspect, obtaining can comprise crushing oral tablets containing an antibacterial or antifungal. In an aspect, obtaining can comprise obtaining an ointment of an antibacterial or antifungal.

Mupirocin is known to the art and is discussed supra. Antibacterial agents are known to the art and are discussed supra. Antifungal agents are known to the art and are discussed supra.

In an aspect, a disclosed compounded composition comprising mupirocin, an antibacterial agent, and an antifungal agent can comprise from about 1.0% w/w to about 3.0% w/w mupirocin. In an aspect, a disclosed compounded composition comprising mupirocin, an antibacterial agent, and an antifungal agent can comprise about 1.6% w/w, or about 1.7% w/w or about 1.756% w/w, or about 1.77% w/w, or about 1.775% w/w, or about 1.8% w/w mupirocin. In an aspect, a disclosed compounded composition comprising mupirocin, an antibacterial agent, and an antifungal agent can comprise from about 4.0% w/w to about 9.0% w/w or from about 6.0% w/w to about 8.0% w/w of the antibacterial agent. In an aspect, a disclosed compounded composition comprising mupirocin, an antibacterial agent, and an antifungal agent can comprise about 5.0% w/w or about 7.5% w/w of the antibacterial agent. In an aspect, a disclosed compounded composition comprising mupirocin, an antibacterial agent, and an antifungal agent can comprise from about 4.0% w/w to about 9.0% w/w or from about 6.0% w/w to about 8.0% w/w of the antifungal agent. In an aspect, a disclosed compounded composition comprising mupirocin, an antibacterial agent, and an antifungal agent can comprise about 5.0% w/w or about 7.5% w/w of the antifungal agent.

In an aspect, a disclosed compounded composition comprises a therapeutically effective amount of mupirocin, a therapeutically effective amount of an additional or second antibacterial agent, and a therapeutically effective amount of an antifungal agent selected from one or more antifungals described herein, such as one or more of ketoconazole, voriconazole, or amphotericin B. The second antibacterial agent may comprise one or more of doxycycline, bacitracin, colistimethate, piperacillin-tazobactam, polymyxin B, or streptomycin. In one embodiment, the second antibacterial agent comprises doxycycline and one or more of bacitracin, colistimethate, piperacillin-tazobactam, polymyxin B, or streptomycin. Other antibacterials may be used in addition to or instead of doxycycline, bacitracin, colistimethate, piperacillin-tazobactam, polymyxin B, or streptomycin, such as the antibacterials described herein.

In one embodiment, a disclosed compounded composition comprising mupirocin and doxycycline or a salt thereof comprises an antifungal agent comprising ketoconazole. In an aspect, a disclosed compounded composition can comprise about 1.6% w/w mupirocin, about 5.0% w/w doxycycline or a pharmaceutically acceptable salt thereof, and about 5.0% w/w ketoconazole. In an aspect, a disclosed compounded composition can comprise about 1.8% w/w mupirocin, about 2.5% w/w doxycycline or a pharmaceutically acceptable salt thereof, and about 2.5% w/w ketoconazole.

In an aspect, a disclosed compounded composition can comprise mupirocin, an antifungal agent, and a second antibacterial agent. In one example, the antifungal agent includes ketoconazole and the second antibacterial agent includes one or more antibacterials (which may include pharmaceutically acceptable salts) selected from bacitracin, colistimethate, piperacillin-tazobactam, polymyxin B, streptomycin, or doxycycline. In one such example, the antifungal agent includes ketoconazole and the second antibacterial agent includes doxycycline and one or more antibacterials selected from bacitracin, colistimethate, piperacillin-tazobactam, polymyxin B, or streptomycin. In an aspect, the mupirocin can comprise an ointment (for example, a mupirocin 2.0% ointment), the doxycycline or a pharmaceutically acceptable salt thereof can comprise a dry powder, and the ketoconazole can comprise a dry powder. In an aspect, a disclosed compounded composition can comprise from about 1.6% to about 1.8% w/w mupirocin, from about 1.0% to about 5.0% w/w doxycycline or a pharmaceutically acceptable salt thereof, and from about 1.0% to about 5.0% w/w ketoconazole. In an aspect, a disclosed compounded composition can comprise from about 1.6 to about 1.7% w/w mupirocin, from about 1.0% to about 5.0% w/w doxycycline, from about 2% to about 6% w/w streptomycin, and from about 1.0% to about 5.0% w/w ketoconazole. In another embodiment, streptomycin may be replaced by about antibacterial. For example, streptomycin may be replaced by an antibacterial selected from bacitracin, colistimethate, piperacillin-tazobactam, or polymyxin B in an amount from about 2% to about 6% w/w. In another embodiment, streptomycin may be replaced by an antifungal. For example, streptomycin may be replaced by an antifungal selected from voriconazole or amphotericin B in an amount from about 1% to about 5% w/w. In one example, a disclosed compounded composition can comprise about 1.7% w/w mupirocin, about 2% w/w doxycycline, about 4% w/w streptomycin, and about 2.5% w/w ketoconazole.

In one aspect, a disclosed compounded composition comprises a compounded ointment comprising doxycycline, tobramycin, mupirocin, and ketoconazole. The doxycycline may comprise crushed doxycycline hyclate tablets, e.g., 100 mg tablets. The tobramycin may comprise tobramycin sulfate for injection powder. The mupirocin may comprise mupirocin 2% ointment. The ketoconazole may comprise crushed ketoconazole tablets, e.g., 200 mg tablets.

A method of compounding a compounded composition comprising mupirocin, doxycycline, streptomycin, and ketoconazole may comprise grinding a suitable amount of doxycycline hyclate tablets and ketoconazole tablets and combining the powder from the crushed tablets with a suitable amount of streptomycin sulfate for injection powder and a suitable volume of mupirocin 2% ointment. For example, compounding a compounded composition comprising about 2% w/w doxycycline, about 1.71% w/w mupirocin, about 4% w/w streptomycin, and about 2.5% w/w ketoconazole may include crushing doxycycline hyclate tablets and ketoconazole tablets and combining the powder from the crushed tablets with a suitable amount of tobramycin sulfate for injection powder and a suitable volume of mupirocin 2% ointment. Each gram of the compounded composition contains about 2% doxycycline (or 20 mg doxycycline), which is equivalent to 0.20 tablets of 100 mg doxycycline tablets, which is equivalent to about 48.7 mg (20% of 243.5 mg total weight of a 100 mg doxycycline tablet). Each gram of compounded composition contains about 2.5% ketoconazole (or 25 mg ketoconazole) which is equivalent to about 0.125 tablets of 200 mg ketoconazole tablets, which is equivalent to about 38.75 mg (25% of 310 mg total weight of a 100 mg ketoconazole tablet). Each gram of compounded composition contains about 4% streptomycin, equivalent to about 40 mg streptomycin USP, equivalent to about 55.28 mg of streptomycin sulfate, which may reflect usage of about 4% of 1 vial of streptomycin 1 g vials per gram of compounded composition. The powders may be added to a suitable amount of mupirocin ointment to formulate the desired concentration of the compounded composition ointment. For example, for every gram of compounded composition ointment, the powders may be combined with about 0.863 g of mupirocin 2% ointment. The combined mixture may be suitably processed in an ointment mill as described elsewhere herein. The compounded composition may be packaged in suitable packaging, e.g., tubes or syringes. As noted elsewhere herein, the term "about" means a value falling within a range that is ±10% of the stated value. Thus, in an aspect, the skilled person can combine 0.8573 g±10% mupirocin 2.0% ointment, 0.0487 g±10% powder from crushed doxycycline hyclate 100 mg tablets, 0.05528 g±10% streptomycin sulfate USP powder for injection, and 0.03875 g±10% powder from crushed ketoconazole 200 mg tablets and mix together according to a method described above to make about 1.0 g±10% of the compounded composition. Other strength tablets and ointments may be used wherein amounts combined are suitably adjusted.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

In an aspect, the mixing can comprise using an electronic mortar and pestle (EMP). In an aspect, a disclosed method can comprise milling the mixture of ingredients (using, for example, a three-roll mill). Mixing and milling can be done according to standards known to the skilled person in the art.

In one example, a method of making a compounded composition comprising 1.7% w/w mupirocin, about 2% w/w doxycycline, about 4% w/w streptomycin, and about 2.5% w/w ketoconazole comprises obtaining mupirocin, doxycycline, streptomycin, and ketoconazole. In an aspect, mupirocin may comprise mupirocin 2% ointment and can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, the average weight of a ketoconazole tablet can be about 0.310 grams and can comprise about 200 mg of ketoconazole. In an aspect, the formula presented below can be used to identify the approximate amount of powder from crushed commercially available ketoconazole tablets needed for 1 g of the compounded composition:

| avg. tablet weight (g) × | % of a tablet needed = | amt. of powder from crushed tablet needed (g) |
|---|---|---|
| (0.3100 g) | (25.0%) | (0.0775 g) |

In an aspect, a disclosed compounded composition comprising mupirocin, tobramycin or a salt thereof, and ketoconazole can comprise from about 1.4% w/w to about 2.0% w/w, from about 1.5% w/w to about 1.9% w/w, or from about 1.6% w/w to about 1.8% w/w mupirocin. In an aspect, a disclosed compounded composition comprising mupirocin, tobramycin or a salt thereof, and ketoconazole can comprise about 1.695% w/w or about 1.8475% w/w mupirocin. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w tobramycin or a pharmaceutically acceptable salt thereof. In an aspect, a disclosed compounded composition comprising mupirocin, tobramycin or a salt thereof, and ketoconazole can comprise about 2.5% w/w or about 5.0% w/w tobramycin or a pharmaceutically acceptable salt thereof. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w ketoconazole. In an aspect, a disclosed compounded composition comprising mupirocin, tobramycin or a salt thereof, and ketoconazole can comprise about 2.5% w/w or about 5.0% w/w ketoconazole.

In an aspect, a disclosed compounded composition comprising mupirocin, tobramycin or a salt thereof, and ketoconazole can comprise from about 1.695% w/w mupirocin, about 5.0% w/w tobramycin or a pharmaceutically acceptable salt thereof, and about 5.0% w/w ketoconazole.

In an aspect, a disclosed compounded composition comprising mupirocin, tobramycin or a salt thereof, and ketoconazole can comprise from about 1.8475% w/w mupirocin, about 2.5% w/w tobramycin or a pharmaceutically acceptable salt thereof, and about 2.5% w/w ketoconazole.

In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, tobramycin or a salt thereof, and ketoconazole into a container and sealing the container. In an aspect, a container can be a container disclosed herein, such as, for example, a syringe. In an aspect, a disclosed method can comprise sterilizing the compounded composition comprising mupirocin, tobramycin or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, tobramycin or a pharmaceutically acceptable salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 13

In an aspect, to make 1 g of the compounded composition, which has about 1.8475% w/w mupirocin, about 2.5% w/w tobramycin or a pharmaceutically acceptable salt thereof, and about 2.5% w/w ketoconazole, about 0.92375 g of mupirocin 2.0% ointment, about 0.0375 g of tobramycin sulfate for injection USP powder, and about 0.03875 g of powder from crushed ketoconazole tablets.

Table 13 provides the approximate amount of mupirocin, tobramycin sulfate, and ketoconazole needed to make various amounts of the compounded composition.

TABLE 13

MUPIROCIN, TOBRAMYCIN SULFATE, AND KETOCONAZOLE

| Compounded Composition (in grams) | Mupirocin (2.0% ointment) | Tobramycin Sulfate (USP powder for injection) | Ketoconazole (powder from crushed tablets) |
|---|---|---|---|
| 1 | 0.92375 g | 0.0375 g | 0.03875 g |
| 4 | 3.695 g | 0.15 g | 0.155 g |
| 8 | 7.39 g | 0.30 g | 0.31 g |
| 25 | 23.09375 g | 0.9375 g | 0.96875 g |
| 50 | 46.1875 g | 1.875 g | 1.9375 g |
| 240 | 221.7 g | 9.0 g | 9.3 g |
| 1500 | 1385.625 g | 56.25 g | 58.125 g |

As used in Example 13, the term "about" means a value falling within a range that is ±10% of the stated value. In an aspect, the skilled person can combine 0.92375 g±10% mupirocin 2.0% ointment (e.g., from about 0.8313 g-1.0161 g), 0.0375 g±10% tobramycin sulfate USP powder for injection (e.g., from about 0.03375 g-0.04125 g), and 0.03875 g±10% powder from crushed ketoconazole tablets (e.g., from about 0.03487 g-0.04262 g) and mix together according to a method described above to make about 1.0 g±10% of the compounded composition.

Mupirocin, Doxycycline or a Salt Thereof, and Fluconazole

Disclosed herein is a method of making a compounded composition, the method comprising: mixing a therapeutically effective amount of mupirocin, a therapeutically effective amount of doxycycline or a pharmaceutically acceptable salt thereof, and a therapeutically effective amount of fluconazole to make a homogeneous compounded composition. A disclosed compounded composition can comprise a dry powder formulation or can comprise an ointment.

In an aspect, a disclosed method can comprise obtaining the mupirocin, obtaining the doxycycline or a pharmaceutically acceptable salt thereof, obtaining the fluconazole, or a combination thereof. In an aspect, obtaining can comprise obtaining a bulk source of the mupirocin, obtaining a bulk source of the doxycycline or a pharmaceutically acceptable salt thereof, obtaining a bulk source of the fluconazole, or a combination thereof.

Mupirocin is known to the art and is discussed supra. Doxycycline as well as pharmaceutically acceptable salts thereof are known to the art and are discussed supra. Fluconazole is known to the art and is discussed supra.

In an aspect, a disclosed compounded composition comprising mupirocin, doxycycline or a salt thereof, and fluconazole can comprise from about 1.0% w/w to about 3.0% w/w mupirocin. In an aspect, a disclosed compounded composition comprising mupirocin, doxycycline or a salt thereof, and fluconazole can comprise about 1.655% w/w mupirocin. In an aspect, a disclosed compounded composition comprising mupirocin, doxycycline or a salt thereof, and fluconazole can comprise from about 1.5% w/w to about 3.5% w/w fluconazole. In an aspect, a disclosed compounded composition comprising mupirocin, doxycycline or a salt thereof, and fluconazole can comprise about 2.5% w/w fluconazole. In an aspect, a disclosed compounded composition comprising mupirocin, doxycycline or a salt thereof, and fluconazole can comprise from about 4.0% to about 6.0% w/w doxycycline or the pharmaceutically acceptable salt thereof. In an aspect, a disclosed compounded composition comprising mupirocin, doxycycline or a salt thereof, and fluconazole about 5.0% w/w doxycycline or a pharmaceutically acceptable salt thereof. In an aspect, a disclosed compounded composition comprising mupirocin, doxycycline or a salt thereof, and fluconazole can comprise about 1.655% w/w mupirocin, about 5.0% w/w doxycycline or a pharmaceutically acceptable salt thereof, and about 2.5% w/w fluconazole.

In an aspect, the formula presented below can be used to identify the approximate amount of powder from crushed doxycycline hyclate tablets needed for 1 g of the compounded composition:

avg. tablet weight (g) $x$ % of a tablet needed=amt. of powder from crushed tablets needed (g)

In an aspect, the average weight of a doxycycline hyclate tablet can be about 0.2435 grams and can comprise about 100 mg of doxycycline. In an aspect, using the above-identified formula, the amount of powder from crushed doxycycline hyclate tablets can be determined to be about 0.12175 g (or 121.75 mg).

average tablet weight × % of a tablet needed = amount of powder from crushed tablets needed (0.2435 g)   (50%)   (0.12175 g)

In an aspect, the formula presented below can be used to identify the approximate amount of powder from crushed fluconazole tablets needed for 1 g of the compounded composition:

In an aspect, the average weight of a fluconazole tablet can be about 0.405 grams and can comprise about 200 mg of fluconazole. In an aspect, using the above-identified formula, the amount of powder from crushed fluconazole tablets can be determined to be about 0.050625 g (or 50.625 mg).

average tablet weight × % of a tablet needed = amount of powder from crushed tablets needed (0.405 g)   (12.5%)   (0.050625 g)

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, doxycycline or a salt thereof, and fluconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, doxycycline or a salt thereof, and fluconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, doxycycline or a pharmaceutically acceptable salt thereof, and fluconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450).

The milled compounded composition can then be mixed again using, for example, an EMP, and then distributed into one or more containers, such as one or more containers disclosed herein (e.g., a plastic tube, a glass or non-glass vial, a syringe, etc.).

Example 10

In an aspect, to make 1 g of the compounded composition, which has about 1.655% w/w mupirocin, about 5.0% w/w doxycycline or a pharmaceutically acceptable salt thereof, and about 2.5% w/w fluconazole, about 0.8276 g of mupirocin 2.0% ointment, about 0.12175 g of powder from crushed doxycycline hyclate tablets, and about 0.050625 g of powder from crushed fluconazole tablets can be combined and mixed together according to a method described above.

Table 10 provides the approximate amount of mupirocin, doxycycline hyclate, and fluconazole needed to make various amounts of the compounded composition.

TABLE 10

MUPIROCIN, DOXYCYCLINE HYCLATE, AND FLUCONAZOLE

| Compounded Composition (in grams) | Mupirocin (2.0% ointment) | Doxycycline Hyclate (powder from crushed tablets) | Fluconazole (powder from crushed tablets) |
| --- | --- | --- | --- |
| 1 | 0.8276 g | 0.12175 g | 0.050625 g |
| 4 | 3.3104 g | 0.487 g | 0.2025 g |
| 8 | 6.6208 g | 0.974 g | 0.405 g |
| 25 | 20.69 g | 3.04375 g | 1.26562 g |
| 50 | 41.38 g | 6.0875 g | 2.53125 g |
| 240 | 198.624 g | 29.22 g | 12.15 g |
| 1500 | 1241.4 g | 182.625 g | 75.9375 g |

As used in Example 10, the term "about" means a value falling within a range that is ±10% of the stated value. In an aspect, the skilled person can combine 0.8276 g±10% mupirocin 2.0 ointment (e.g., from about 0.74484 g-0.91036 g), 0.12175 g±10% powder from crushed doxycycline hyclate tablets (e.g., from about 0.109575 g-0.133925 g), and 0.050625 g±10% powder from crushed fluconazole tablets (e.g., from about 0.0455625 g-0.0556875 g) and mix together according to a method described above to make about 1.0 g±10% of the compounded composition.

Mupirocin, Doxycycline or a Salt Thereof, and Ketoconazole

Disclosed herein is a method of making a compounded composition, the method comprising: mixing a therapeutically effective amount of mupirocin, a therapeutically effective amount of a doxycycline or a pharmaceutically acceptable salt thereof, and a therapeutically effective amount of a ketoconazole to make a homogeneous compounded composition. A disclosed compounded composition can comprise a dry powder formulation or can comprise an ointment.

In an aspect, a disclosed method can comprise obtaining the mupirocin, obtaining the doxycycline or a pharmaceutically acceptable salt thereof, obtaining the ketoconazole, or a combination thereof. In an aspect, obtaining can comprise obtaining a bulk source of the mupirocin, obtaining a bulk source of the doxycycline or a pharmaceutically acceptable salt thereof, obtaining a bulk source of the ketoconazole, or a combination thereof.

Mupirocin is known to the art and is discussed supra. Doxycycline as well as pharmaceutically acceptable salts thereof are known to the art and are discussed supra. Ketoconazole is known to the art and is discussed supra.

In an aspect, a disclosed compounded composition comprising mupirocin, doxycycline or a salt thereof, and ketoconazole can comprise from about 1.0% w/w to about 3.0% w/w mupirocin. In an aspect, a disclosed compounded composition comprising mupirocin, doxycycline or a salt thereof, and ketoconazole can comprise about 1.6% w/w or about 1.8% w/w mupirocin. In an aspect, a disclosed compounded composition comprising mupirocin, doxycycline or a salt thereof, and ketoconazole can comprise from about 1.5% to about 3.5% w/w or from about 4.0% to about 6.0% w/w doxycycline or a pharmaceutically acceptable salt thereof. In an aspect, a disclosed compounded composition comprising mupirocin, doxycycline or a salt thereof, and ketoconazole can comprise about 2.5% w/w or 5.0% w/w doxycycline or a pharmaceutically acceptable salt thereof. In an aspect, a disclosed compounded composition comprising mupirocin, doxycycline or a salt thereof, and ketoconazole can comprise from about 1.5% w/w to about 3.5% w/w or from about 4.0% to about 6.0% w/w ketoconazole. In an aspect, a disclosed compounded composition comprising mupirocin, doxycycline or a salt thereof, and ketoconazole can comprise about 2.5% w/w or about 5.0% w/w ketoconazole. In an aspect, a disclosed compounded composition comprising mupirocin, doxycycline or a salt thereof, and ketoconazole can comprise about 1.6% w/w mupirocin, about 5.0% w/w doxycycline or a pharmaceutically acceptable salt thereof, and about 5.0% w/w ketoconazole.

In an aspect, a disclosed compounded composition comprising mupirocin, doxycycline or a salt thereof, and ketoconazole can comprise about 1.8% w/w mupirocin, about 2.5% w/w doxycycline or a pharmaceutically acceptable salt thereof, and about 2.5% w/w ketoconazole.

In an aspect, the formula presented below can be used to identify the approximate amount of powder from crushed doxycycline hyclate tablets needed for 1 g of the compounded composition:

avg. tablet weight (g) x % of a tablet needed=amt. of powder from crushed tablets needed (g)

In an aspect, the average weight of a doxycycline hyclate tablet can be about 0.2435 grams and can comprise about 100 mg of doxycycline. In an aspect, using the above-identified formula, the amount of powder from crushed doxycycline hyclate tablets needed for 1 g of the compounded composition can be determined to be about 0.060875 g (or 60.875 mg).

average tablet weight × % of a tablet needed = amount of powder from crushed tables needed (0.2435 g)         (25.0%)         (0.060875 g)

In an aspect, using the above-identified formula, the amount of powder from crushed doxycycline hyclate tablets needed for 1 g of the compounded composition can be determined to be about 0.12175 g (or 121.75 mg).

average tablet weight × % of a tablet needed = amount of powder from crushed tables needed (0.2435 g)         (50%)         (0.12175 g)

In an aspect, the formula presented below can be used to identify the approximate amount of powder from crushed ketoconazole tablets needed for 1 g of the compounded composition:

avg. tablet weight (g) x % of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets needed for 1 g of the compounded composition can be determined to be about 0.0775 g (or 77.5 mg).

$$\text{avg. tablet weight (g)} \times \text{\% of a tablet needed} = \text{amt. of powder from crushed tablets needed (g)}$$

$$(0.3100 \text{ g}) \quad (25.0\%) \quad (0.0775 \text{ g})$$

In an aspect, using the above-identified formula, the amount of powder from crushed ketoconazole tablets needed for 1 g of the compounded composition can be determined to be about 0.03875 g (or 38.75 mg).

$$\text{avg. tablet weight (g)} \times \text{\% of a tablet needed} = \text{amt. of powder from crushed tablets needed (g)}$$

$$(0.3100 \text{ g}) \quad (12.5\%) \quad (0.03875 \text{ g})$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, doxycycline or a salt thereof, and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, doxycycline or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, doxycycline or a pharmaceutically acceptable salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 11

In an aspect, to make 1 g of the compounded composition, which has about 1.6% w/w mupirocin, about 5.0% w/w doxycycline or a pharmaceutically acceptable salt thereof, and about 5.0% w/w ketoconazole, about 0.8008 g of mupirocin 2.0% ointment, about 0.12175 g of powder from crushed doxycycline hyclate tablets, and about 0.0775 g of powder from crushed ketoconazole tablets can be combined and mixed together according to a disclosed method described above.

Table 11 provides the approximate amount of mupirocin, doxycycline hyclate, and ketoconazole needed to make various amounts of the compounded composition.

TABLE 11

MUPIROCIN, DOXYCYCLINE HYCLATE, AND KETOCONAZOLE

| Compounded Composition (in grams) | Mupirocin (2.0% ointment) | Doxycycline Hyclate (powder from crushed tablets) | Ketoconazole (powder from crushed tablets) |
| --- | --- | --- | --- |
| 1 | 0.8008 g | 0.12175 g | 0.0775 g |
| 4 | 3.2032 g | 0.487 g | 0.31 g |
| 8 | 6.4064 g | 0.974 g | 0.62 g |
| 25 | 20.02 g | 3.04375 g | 1.9375 g |
| 50 | 40.04 g | 6.0875 g | 3.875 g |
| 240 | 192.192 g | 29.22 g | 18.6 g |
| 1500 | 1201.2 g | 182.625 g | 116.25 g |

As used in Example 11, the term "about" means a value falling within a range that is ±10% of the stated value. In an aspect, the skilled person can combine 0.8008 g±10% mupirocin 2.0% ointment (e.g., from about 0.72072 g-0.88088 g), 0.12175 g±10% powder from crushed doxycycline hyclate tablets (e.g., from about 0.109575 g-0.133925 g), and 0.0775 g±10% powder from crushed ketoconazole tablets (e.g., from about 0.06975 g-0.08525 g) and mix together according to a method described above to make about 1.0 g±10% of the compounded composition.

Example 12

In an aspect, to make 1 g of the compounded composition, which has about 1.8% w/w mupirocin, about 2.5% w/w doxycycline or a pharmaceutically acceptable salt thereof, and about 2.5% w/w ketoconazole, about 0.9004 g of mupirocin 2.0% ointment, about 0.060875 g of powder from crushed doxycycline hyclate tablets, and about 0.03875 g of powder from crushed ketoconazole tablets can be combined and mixed together according to a disclosed method described above.

Table 12 provides the approximate amount of mupirocin, doxycycline hyclate, and ketoconazole needed to make various amounts of the compounded composition.

TABLE 12

MUPIROCIN, DOXYCYCLINE HYCLATE, AND KETOCONAZOLE

| Compounded Composition (in grams) | Mupirocin (2.0% ointment) | Doxycycline Hyclate (powder from crushed tablets) | Ketoconazole (powder from crushed tablets) |
| --- | --- | --- | --- |
| 1 | 0.9004 g | 0.060875 g | 0.03875 g |
| 4 | 3.6016 g | 0.2435 g | 0.155 g |
| 8 | 7.2032 g | 0.487 g | 0.31 g |
| 25 | 22.51 g | 1.521875 g | 0.96875 g |
| 50 | 45.02 g | 3.04375 g | 1.9375 g |
| 240 | 216.096 g | 14.61 g | 9.3 g |
| 1500 | 1350.6 g | 91.3125 g | 58.125 g |

As used in Example 12, the term "about" means a value falling within a range that is ±10% of the stated value. In an aspect, the skilled person can combine 0.9004 g±10% mupirocin 2.0% ointment (e.g., from about 0.81036 g-0.99044 g), 0.060875 g±10% powder from crushed doxycycline hyclate tablets (e.g., from about 0.0547875 g-0.0669625 g), and 0.03875 g±10% powder from crushed ketoconazole tablets (e.g., from about 0.034875 g-0.042625 g) and mix together according to a method described above to make about 1.0 g±10% of the compounded composition.

Mupirocin, Tobramycin or a Salt Thereof, and Ketoconazole

Disclosed herein is a method of making a compounded composition, the method comprising: mixing a therapeutically effective amount of mupirocin, a therapeutically effective amount of tobramycin or a pharmaceutically acceptable salt thereof, and a therapeutically effective amount of ketoconazole to make a homogeneous compounded composition. A disclosed compounded composition can comprise a dry powder formulation or can comprise an ointment.

In an aspect, a disclosed method can comprise obtaining the mupirocin, obtaining the tobramycin or a pharmaceutically acceptable salt thereof, obtaining the ketoconazole, or a combination thereof. In an aspect, obtaining can comprise obtaining a bulk source of the mupirocin, obtaining a bulk source of the tobramycin or a pharmaceutically acceptable salt thereof, obtaining a bulk source of ketoconazole, or a combination thereof.

Mupirocin is known to the art and is discussed supra. Tobramycin as well as pharmaceutically acceptable salts thereof are known to the art and are discussed supra. Ketoconazole is known to the art and is discussed supra.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, the average weight of a ketoconazole tablet can be about 0.310 grams and can comprise about 200 mg of ketoconazole. In an aspect, the formula presented below can be used to identify the approximate amount of powder from crushed commercially available ketoconazole tablets needed for 1 g of the compounded composition:

| avg. tablet weight (g) × | % of a tablet needed = | amt. of powder from crushed tablets needed (g) |
| --- | --- | --- |
| (0.3100 g) | (25.0%) | (0.0775 g) |

In an aspect, a disclosed compounded composition comprising mupirocin, tobramycin or a salt thereof, and ketoconazole can comprise from about 1.4% w/w to about 2.0% w/w, from about 1.5% w/w to about 1.9% w/w, or from about 1.6% w/w to about 1.8% w/w mupirocin. In an aspect, a disclosed compounded composition comprising mupirocin, tobramycin or a salt thereof, and ketoconazole can comprise about 1.695% w/w or about 1.8475% w/w mupirocin. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w tobramycin or a pharmaceutically acceptable salt thereof. In an aspect, a disclosed compounded composition comprising mupirocin, tobramycin or a salt thereof, and ketoconazole can comprise about 2.5% w/w or about 5.0% w/w tobramycin or a pharmaceutically acceptable salt thereof. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w ketoconazole. In an aspect, a disclosed compounded composition comprising mupirocin, tobramycin or a salt thereof, and ketoconazole can comprise about 2.5% w/w or 5.0% w/w ketoconazole.

In an aspect, a disclosed compounded composition comprising mupirocin, tobramycin or a salt thereof, and ketoconazole can comprise from about 1.695% w/w mupirocin, about 5.0% w/w tobramycin or a pharmaceutically acceptable salt thereof, and about 5.0% w/w ketoconazole.

In an aspect, a disclosed compounded composition comprising mupirocin, tobramycin or a salt thereof, and ketoconazole can comprise from about 1.8475% w/w mupirocin, about 2.5% w/w tobramycin or a pharmaceutically acceptable salt thereof, and about 2.5% w/w ketoconazole.

In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, tobramycin or a salt thereof, and ketoconazole into a container and sealing the container. In an aspect, a container can be a container disclosed herein, such as, for example, a syringe. In an aspect, a disclosed method can comprise sterilizing the compounded composition comprising mupirocin, tobramycin or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, tobramycin or a pharmaceutically acceptable salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 13

In an aspect, to make 1 g of the compounded composition, which has about 1.8475% w/w mupirocin, about 2.5% w/w tobramycin or a pharmaceutically acceptable salt thereof, and about 2.5% w/w ketoconazole, about 0.92375 g of mupirocin 2.0% ointment, about 0.0375 g of tobramycin sulfate for injection USP powder, and about 0.03875 g of powder from crushed ketoconazole tablets.

Table 13 provides the approximate amount of mupirocin, tobramycin sulfate, and ketoconazole needed to make various amounts of the compounded composition.

TABLE 13

MUPIROCIN, TOBRAMYCIN SULFATE, AND KETOCONAZOLE

| Compounded Composition (in grams) | Mupirocin (2.0% ointment) | Tobramycin Sulfate (USP powder for injection) | Ketoconazole (powder from crushed tablets) |
| --- | --- | --- | --- |
| 1 | 0.92375 g | 0.0375 g | 0.03875 g |
| 4 | 3.695 g | 0.15 g | 0.155 g |
| 8 | 7.39 g | 0.30 g | 0.31 g |
| 25 | 23.09375 g | 0.9375 g | 0.96875 g |
| 50 | 46.1875 g | 1.875 g | 1.9375 g |
| 240 | 221.7 g | 9.0 g | 9.3 g |
| 1500 | 1385.625 g | 56.25 g | 58.125 g |

As used in Example 13, the term "about" means a value falling within a range that is ±10% of the stated value. In an aspect, the skilled person can combine 0.92375 g±10% mupirocin 2.0% ointment (e.g., from about 0.8313 g-1.0161 g), 0.0375 g±10% tobramycin sulfate USP powder for injection (e.g., from about 0.03375 g-0.04125 g), and 0.03875 g±10% powder from crushed ketoconazole tablets (e.g., from about 0.03487 g-0.04262 g) and mix together according to a method described above to make about 1.0 g±10% of the compounded composition.

Example 14

In an aspect, to make about 1 g of the compounded composition, which has about 1.695% w/w mupirocin, about 5.0% w/w tobramycin or a pharmaceutically acceptable salt thereof, and about 5.0% w/w ketoconazole, about 0.8475 g of mupirocin 2.0% ointment, about 0.075 g of tobramycin sulfate for injection USP powder, and about 0.0775 g of powder from crushed ketoconazole tablets.

Table 14 provides the approximate amount of mupirocin, tobramycin sulfate, and ketoconazole needed to make various amounts of the compounded composition.

TABLE 14

MUPIROCIN, TOBRAMYCIN SULFATE, AND KETOCONAZOLE

| Compounded Composition (in grams) | Mupirocin (2.0% ointment) | Tobramycin Sulfate (USP powder for injection) | Ketoconazole (powder from crushed tablets) |
| --- | --- | --- | --- |
| 1 | 0.8475 g | 0.075 g | 0.0775 g |
| 4 | 3.39 g | 0.30 g | 0.31 g |
| 8 | 6.78 g | 0.60 g | 0.62 g |
| 25 | 21.1875 g | 1.875 g | 1.9375 g |
| 50 | 42.375 g | 3.75 g | 3.875 g |
| 240 | 203.4 g | 18.0 g | 18.6 g |
| 1500 | 1271.25 g | 112.5 g | 116.25 g |

As used in Example 14, the term "about" means a value falling within a range that is ±10% of the stated value. In an aspect, the skilled person can combine 0.8475 g±10% mupirocin 2.0% ointment (e.g., from about 0.7627 g-0.9322 g), 0.075 g±10% tobramycin sulfate USP powder for injection (e.g., from about 0.0675 g-0.0825 g), and 0.0775 g±10% powder from crushed ketoconazole tablets (e.g., from about 0.06975 g-0.08525 g) and mix together according to a method described above to make about 1.0 g±10% of the compounded composition.

Mupirocin, Tobramycin or a Salt Thereof, and Fluconazole

Disclosed herein is a method of making a compounded composition, the method comprising: mixing a therapeutically effective amount of mupirocin, a therapeutically effective amount of tobramycin or a pharmaceutically acceptable salt thereof, and a therapeutically effective amount of fluconazole to make a homogeneous compounded composition. A disclosed compounded composition can comprise a dry powder formulation or can comprise an ointment.

In an aspect, a disclosed method can comprise obtaining the mupirocin, obtaining the tobramycin or a pharmaceutically acceptable salt thereof, obtaining the fluconazole, or a combination thereof. In an aspect, obtaining can comprise obtaining a bulk source of the mupirocin, obtaining a bulk source of the tobramycin or a pharmaceutically acceptable salt thereof, obtaining a bulk source of fluconazole, or a combination thereof.

Mupirocin is known to the art and is discussed supra. Tobramycin as well as pharmaceutically acceptable salts thereof are known to the art and are discussed supra. Fluconazole is known to the art and is discussed supra.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, the formula presented below can be used to identify the approximate amount of powder from crushed fluconazole tablets needed for 1 g of the compounded composition:

average tablet weight $x$ % of a tablet needed=amount of powder from crushed tablets needed (g)

In an aspect, the average weight of a fluconazole tablet can be about 0.405 grams and can comprise about 200 mg of fluconazole. In an aspect, using the above-identified formula, the amount of powder from crushed fluconazole tablets can be determined.

| average tablet weight × | % of a tablet needed = | amount of powder from crushed tablets needed (g) |
|---|---|---|
| (0.405 g) | (12.5%) | (0.050625 g) |

In an aspect, a disclosed compounded composition comprising mupirocin, tobramycin or a salt thereof, and fluconazole can comprise about 1.8% w/w mupirocin, about 2.5% w/w tobramycin or a pharmaceutically acceptable salt thereof, and about 2.5% w/w fluconazole. In an aspect, a disclosed compounded composition comprising mupirocin, tobramycin or a salt thereof, and fluconazole can comprise about 1.8475% w/w mupirocin, about 2.5% w/w tobramycin or a pharmaceutically acceptable salt thereof, and about 2.5% w/w fluconazole.

In an aspect, a disclosed compounded composition comprising mupirocin, tobramycin or a salt thereof, and fluconazole can comprise about 1.7% w/w mupirocin, about 5.0% w/w tobramycin or a pharmaceutically acceptable salt thereof, and about 5.0% w/w fluconazole. In an aspect, a disclosed compounded composition comprising mupirocin, tobramycin or a salt thereof, and fluconazole can comprise about 1.695% w/w mupirocin, about 5.0% w/w tobramycin or a pharmaceutically acceptable salt thereof, and about 5.0% w/w fluconazole.

In an aspect, a disclosed compounded composition comprising mupirocin, tobramycin or a salt thereof, and fluconazole can comprise from about 1.7% w/w to about 1.8% w/w mupirocin, about 5.0% w/w tobramycin or a pharmaceutically acceptable salt thereof, and about 2.5% w/w fluconazole. In an aspect, a disclosed compounded composition comprising mupirocin, tobramycin or a salt thereof, and fluconazole can comprise about 1.749% w/w mupirocin, about 5.0% w/w tobramycin or a pharmaceutically acceptable salt thereof, and about 2.5% w/w fluconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, tobramycin or a salt thereof, and fluconazole into a container and sealing the container. In an aspect, a container can be a container disclosed herein, such as, for example, a syringe. In an aspect, a disclosed method can comprise sterilizing the compounded composition comprising mupirocin, tobramycin or a salt thereof, and fluconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, tobramycin or a pharmaceutically acceptable salt thereof, and fluconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 15

In an aspect, to make 1 g of the compounded composition, which has about 1.749% w/w mupirocin, about 5.0% w/w tobramycin or a pharmaceutically acceptable salt thereof, and about 2.5% w/w fluconazole, about 0.8744 g of mupirocin 2.0% ointment, about 0.075 g of tobramycin sulfate for injection USP powder, and about 0.050625 g of powder from crushed fluconazole tablets can be combined and mixed together according to a disclosed method described above.

Table 15 provides the approximate amount of mupirocin, tobramycin sulfate, and fluconazole needed to make various amounts of the compounded composition.

TABLE 15

MUPIROCIN, TOBRAMYCIN SULFATE, AND FLUCONAZOLE

| Compounded Composition (in grams) | Mupirocin (2.0% ointment) | Tobramycin Sulfate (USP powder for injection) | Fluconazole (powder from crushed tablets) |
|---|---|---|---|
| 1 | 0.8744 g | 0.075 g | 0.050625 g |
| 4 | 3.4976 g | 0.3 g | 0.2025 g |
| 8 | 6.9952 g | 0.6 g | 0.405 g |
| 25 | 21.86 g | 1.875 g | 1.265625 g |
| 50 | 43.72 g | 3.75 g | 2.53125 g |
| 240 | 209.856 g | 18.0 g | 12.15 g |
| 1500 | 1311.6 g | 112.5 g | 75.9375 g |

As used in Example 15, the term "about" means a value falling within a range that is ±10% of the stated value. In an aspect, the skilled person can combine 0.8744 g±10% mupirocin 2.0% ointment (e.g., from about 0.78696 g-0.96184 g), 0.075 g±10% tobramycin sulfate USP powder for injection (e.g., from about 0.0675 g-0.0825 g), and 0.050625 g±10% powder from crushed fluconazole tablets (e.g., from about 0.0455625 g-0.0556875 g) and mix together according to a method described above to make about 1.0 g±10% of the compounded composition.

Example 16

In an aspect, to make 1 g of the compounded composition, which has about 1.8% w/w mupirocin, about 2.5% w/w tobramycin or a pharmaceutically acceptable salt thereof, and about 2.5% w/w fluconazole, about 0.92375 g of mupirocin 2.0% ointment, about 0.0375 g of tobramycin sulfate for injection USP powder, and about 0.03875 g of powder from crushed fluconazole tablets.

Table 16 provides the approximate amount of mupirocin, tobramycin sulfate, and fluconazole needed to make various amounts of the compounded composition.

TABLE 16

MUPIROCIN, TOBRAMYCIN SULFATE, AND FLUCONAZOLE

| Compounded Composition (in grams) | Mupirocin (2.0% ointment) | Tobramycin Sulfate (USP powder for injection) | Fluconazole (powder from crushed tablets) |
|---|---|---|---|
| 1 | 0.92375 g | 0.0375 g | 0.03875 g |
| 4 | 3.695 g | 0.15 g | 0.155 g |
| 8 | 7.39 g | 0.30 g | 0.31 g |
| 25 | 23.09375 g | 0.9375 g | 0.96875 g |
| 50 | 46.1875 g | 1.875 g | 1.9375 g |
| 240 | 221.7 g | 9.0 g | 9.3 g |
| 1500 | 1385.625 g | 56.25 g | 58.125 g |

As used in Example 16, the term "about" means a value falling within a range that is ±10% of the stated value. In an aspect, the skilled person can combine 0.92375 g±10% mupirocin 2.0% ointment (e.g., from about 0.83137 g-1.01612 g), 0.0375 g±10% tobramycin sulfate powder for injection (e.g., from about 0.03375 g-0.04125 g), and 0.03875 g±10% powder from crushed fluconazole tablets (e.g., from about 0.03487 g-0.042625 g) and mix together according to a method described above to make about 1.0 g±10% of the compounded composition.

Example 17

In an aspect, to make about 1 g of the compounded composition, which has about 1.7% w/w mupirocin, about 5.0% w/w tobramycin or a pharmaceutically acceptable salt thereof, and about 5.0% w/w fluconazole, about 0.8475 g of mupirocin 2.0% ointment, about 0.075 g of tobramycin sulfate for injection USP powder, and about 0.0775 g of powder from crushed fluconazole tablets.

Table 17 provides the approximate amount of mupirocin, tobramycin sulfate, and fluconazole needed to make various amounts of the compounded composition.

TABLE 17

MUPIROCIN, TOBRAMYCIN SULFATE, AND FLUCONAZOLE

| Compounded Composition (in grams) | Mupirocin (2.0% ointment) | Tobramycin Sulfate (USP powder for injection) | Fluconazole (powder from crushed tablets) |
|---|---|---|---|
| 1 | 0.8475 g | 0.075 g | 0.0775 g |
| 4 | 3.39 g | 0.30 g | 0.31 g |
| 8 | 6.78 g | 0.60 g | 0.62 g |
| 25 | 21.1875 g | 1.875 g | 1.9375 g |
| 50 | 42.375 g | 3.75 g | 3.875 g |
| 240 | 203.4 g | 18.0 g | 18.6 g |
| 1500 | 1271.25 g | 112.5 g | 116.25 g |

As used in Example 17, the term "about" means a value falling within a range that is ±10% of the stated value. In an aspect, the skilled person can combine 0.8475 g±10% mupirocin 2.0% ointment (e.g., from about 0.76275 g-0.9322 g), 0.075 g±10% powder from tobramycin sulfate powder for injection (e.g., from about 0.0675 g-0.0825 g), and 0.0775 g±10% powder from crushed fluconazole tablets (e.g., from about 0.06975 g-0.08525 g) and mix together according to a method described above to make about 1.0 g±10% of the compounded composition.

Mupirocin, an Azole, and a Fluoroquinolone

Disclosed herein is a method of making a compounded composition, the method comprising: mixing a therapeutically effective amount of mupirocin, a therapeutically effective amount of a fluoroquinolone, and a therapeutically effective amount of an azole to make a homogeneous compounded composition.

In an aspect, a disclosed method can comprise obtaining the mupirocin, obtaining the fluoroquinolone, obtaining the azole, or a combination thereof. In an aspect, obtaining can comprise obtaining a bulk source of the mupirocin, obtaining a bulk source of the fluoroquinolone, obtaining a bulk source of the azole, or a combination thereof.

Mupirocin is known to the art and is discussed supra. Fluoroquinolones are known to the skilled person and are discussed supra. Azoles are known to the skilled person and are discussed supra.

In an aspect, a disclosed compounded composition comprising mupirocin, a fluoroquinolone, and an azole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, a fluoroquinolone, and an azole can comprise about 1.8453% w/w mupirocin.

In an aspect, a disclosed compounded composition comprising mupirocin, a fluoroquinolone, and an azole can comprise from about 1.0% w/w to about 6.0% w/w, from about 1.5% w/w to about 5.0% w/w, from about 2.5% w/w to about 5.0% w/w, from about 2.0% w/w to about 4%, from about 2.0% w/w to about 4.0% w/w, or from about 2.5% w/w to about 3.0% w/w of the fluoroquinolone. In an aspect, a disclosed compounded composition comprising mupirocin, a fluoroquinolone, and an azole can comprise about 2.5% w/w of the fluoroquinolone.

In an aspect, a disclosed compounded composition comprising mupirocin, a fluoroquinolone, and an azole can comprise from about 1.0% w/w to about 6.0% w/w, about 1.5% w/w to about 5.0% w/w, from about 2.5% w/w to about 5.0% w/w, from about 2.0% w/w to about 4.0% w/w, from about 2.0% w/w to about 4.0% w/w, from about 2.5% w/w to about 3.0% w/w of the azole. In an aspect, a disclosed compounded composition comprising mupirocin, a fluoroquinolone, and an azole can comprise about 2.5% w/w of the azole.

In an aspect, a disclosed compounded composition comprising mupirocin, a fluoroquinolone, and an azole can comprise about the same amount of an azole and a fluoroquinolone. In an aspect, a disclosed compounded composition comprising mupirocin, a fluoroquinolone, and an azole can comprise about 1.8453% w/w mupirocin, about 2.5% w/w of the fluoroquinolone, and about 2.5% w/w of the azole. In an aspect, a disclosed compounded composition comprising mupirocin, a fluoroquinolone, and an azole can comprise about 1.768% w/w mupirocin, about 5.0% w/w of the fluoroquinolone, and about 2.5% w/w of the azole. In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, a fluoroquinolone, and an azole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, a fluoroquinolone, and an azole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, the fluoroquinolone, and the azole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Mupirocin, Ciprofloxacin or a Salt Thereof, and Ketoconazole

Disclosed herein is a method of making a compounded composition, the method comprising: mixing a therapeutically effective amount of mupirocin, a therapeutically effective amount of ciprofloxacin or a pharmaceutically acceptable salt thereof, and a therapeutically effective amount of ketoconazole to make a homogeneous compounded composition.

In an aspect, a disclosed method can comprise obtaining mupirocin, obtaining ciprofloxacin or a pharmaceutically acceptable salt thereof, obtaining ketoconazole, or a combination thereof. In an aspect, obtaining can comprise obtaining a bulk source of mupirocin, obtaining a bulk source of ciprofloxacin or a pharmaceutically acceptable salt thereof, obtaining a bulk source of ketoconazole, or a combination thereof.

Mupirocin is known to the art and is discussed supra. Ciprofloxacin as well as pharmaceutically acceptable salts thereof are known to the art and are discussed supra. Ketoconazole is known to the art and is discussed supra.

In an aspect, a disclosed compounded composition comprising mupirocin, ciprofloxacin or a salt thereof, and ketoconazole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, ciprofloxacin or a salt thereof, and ketoconazole can comprise about 1.768% w/w or 1.8453% w/w mupirocin. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ciprofloxacin or a pharmaceutically acceptable salt thereof. In an aspect, a disclosed compounded composition comprising mupirocin, ciprofloxacin or a salt thereof, and ketoconazole can comprise about 2.5% w/w or about 5.0% w/w ciprofloxacin or a pharmaceutically acceptable salt thereof. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ketoconazole. In an aspect, a disclosed compounded composition comprising mupirocin, ciprofloxacin or a salt thereof, and ketoconazole can comprise about 2.5% w/w or about 5.0% w/w ketoconazole.

In an aspect, a disclosed compounded composition can comprise about 1.8453% w/w mupirocin, about 2.5% w/w ciprofloxacin or a pharmaceutically acceptable salt thereof, and about 2.5% w/w ketoconazole.

In an aspect, a disclosed compounded composition can comprise from about 1.768% w/w mupirocin, about 5.0% w/w ciprofloxacin or a pharmaceutically acceptable salt thereof, and about 2.5% w/w ketoconazole.

In an aspect, the formula presented below can be used to identify the approximate amount of powder from crushed commercially available ciprofloxacin tablets needed for 1 g of the compounded composition:

avg. tablet weight (g) x % of a tablet needed=amt. of powder from crushed tablets needed (g)

In an aspect, the average weight of a ciprofloxacin tablet can be about 1.158 grams and can comprise about 750 mg of ciprofloxacin.

| average tablet weight× | % of a tablet needed = | amount of powder from crushed tablets needed |
|---|---|---|
| (1.158 g) | (6.67%) | (0.07723 g) |

| average tablet weight× | % of a tablet needed = | amount of powder from crushed tablets needed |
|---|---|---|
| (1.158 g) | (3.33%) | (0.03856 g) |

In an aspect, the formula presented below can be used to identify the approximate amount of powder from crushed commercially available ketoconazole tablets needed for 1 g of the compounded composition:

avg. tablet weight (g) x % of a tablet needed=amt. of powder from crushed tablets needed (g)

In an aspect, the average weight of a ketoconazole tablet can be about 0.310 grams and can comprise about 200 mg of ketoconazole.

| avg. tablet weight (g) × | % of a tablet needed = | amt. of powder from crushed tablets needed (g) |
|---|---|---|
| (0.3100 g) | (12.5%) | (0.03875 g) |

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, ciprofloxacin or a salt thereof, and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, ciprofloxacin or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, ciprofloxacin or a salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 18

In an aspect, to make 1 g of the compounded composition, which has about 1.8453% w/w mupirocin, about 2.5% w/w ciprofloxacin or a pharmaceutically acceptable salt thereof, and about 2.5% w/w ketoconazole, about 0.9227 g of mupirocin 2.0% ointment, about 0.03856 g of powder from crushed ciprofloxacin tablets, about 0.03875 mg of powder from crushed ketoconazole tablets can be combined and mixed together according to a disclosed method described above.

Table 18 provides the approximate amount of mupirocin, ciprofloxacin, and ketoconazole needed to make various amounts of the compounded composition.

TABLE 18

MUPIROCIN, CIPROFLOXACIN OR A SALT THEREOF, AND KETOCONAZOLE

| Compounded Composition (in grams) | Mupirocin (2.0% ointment) | Ciprofloxacin (powder from crushed tablets) | Ketoconazole (powder from crushed tablets) |
|---|---|---|---|
| 1 | 0.9227 g | 0.03856 g | 0.03875 g |
| 4 | 3.6908 g | 0.15424 g | 0.155 g |
| 8 | 7.3816 g | 0.30848 g | 0.310 g |
| 25 | 23.0675 g | 0.964 g | 0.96875 g |
| 50 | 46.135 g | 1.928 g | 1.9375 g |
| 240 | 221.448 g | 9.2544 g | 9.3 g |
| 1500 | 1384.05 g | 57.84 g | 58.125 g |

As used in Example 18, the term "about" means a value falling within a range that is ±10% of the stated value. In an aspect, the skilled person can combine 0.9227 g±10% mupirocin 2.0% ointment (e.g., from about 0.83043 g-1.01497 g), 0.03856 g±10% powder from crushed ciprofloxacin tablets (e.g., from about 0.034704 g-0.042416 g), and 0.03875 g±10% powder from crushed ketoconazole tablets (e.g., from about 0.034875 g-0.042625 g) and mix together according to a method described above to make about 1.0 g±10% of the compounded composition.

Example 19

In an aspect, to make 1 g of the compounded composition, which has about 1.768% w/w mupirocin, about 5.0% w/w ciprofloxacin or a pharmaceutically acceptable salt thereof, and about 2.5% w/w ketoconazole, 0.8841 g of mupirocin 2% ointment, about 0.07723 g of powder from crushed ciprofloxacin tablets, and about 0.03875 g of powder from crushed ketoconazole tablets (about 12.5% of a crushed 200 mg ketoconazole tablet) can be combined and mixed together according to a disclosed method described above.

Table 19 provides the approximate amount of mupirocin, ciprofloxacin, and ketoconazole powder needed to make various amounts of the compounded composition.

TABLE 19

MUPIROCIN, CIPROFLOXACIN OR A SALT THEREOF, AND KETOCONAZOLE

| Compounded Composition (in grams) | Mupirocin (2.0% ointment) | Ciprofloxacin (powder from crushed tablets) | Ketoconazole (powder from crushed tablets) |
|---|---|---|---|
| 1 | 0.8841 g | 0.07723 g | 0.03875 g |
| 4 | 3.5364 g | 0.30892 g | 0.155 g |
| 8 | 7.0728 g | 0.61784 g | 0.31 g |
| 25 | 22.1025 g | 1.93075 g | 0.96875 g |
| 50 | 44.205 g | 3.8615 g | 1.9375 g |
| 240 | 212.184 g | 18.5352 g | 9.3 g |
| 1500 | 1326.15 g | 115.845 g | 58.125 g |

As used in Example 19, the term "about" means a value falling within a range that is ±10% of the stated value. In an aspect, the skilled person can combine 0.8841 g±10% mupirocin 2.0% ointment (e.g., from about 0.79569 g-0.97251 g), 0.07723 g±10% powder from crushed ciprofloxacin tablets (e.g., from about 0.069507 g-0.084953 g), and 0.03875 g±10% powder from crushed ketoconazole tablets (e.g., from about 0.034875 g-0.042625 g) and mix together according to a method described above to make about 1.0 g±10% of the compounded composition.

Mupirocin, Azithromycin, and Ketoconazole

Disclosed herein is a method of making a compounded composition, the method comprising: mixing a therapeutically effective amount of mupirocin, a therapeutically effective amount of azithromycin, and a therapeutically effective amount of a ketoconazole to make a homogeneous compounded composition. A disclosed compounded composition can comprise a dry powder formulation or can comprise an ointment.

In an aspect, a disclosed method can comprise obtaining the mupirocin, obtaining the azithromycin, obtaining the ketoconazole, or a combination thereof. In an aspect, obtaining can comprise obtaining a bulk source of the mupirocin, obtaining a bulk source of the azithromycin, obtaining a bulk source of the ketoconazole, or a combination thereof.

Mupirocin is known to the art and is discussed supra. Azithromycin is known to the art and is discussed supra. Ketoconazole is known to the art and is discussed supra.

In an aspect, a disclosed compounded composition comprising mupirocin, azithromycin, and ketoconazole can comprise from about 1.0% w/w to about 3.0% w/w mupirocin. In an aspect, a disclosed compounded composition comprising mupirocin, azithromycin, and ketoconazole can comprise about 1.645% w/w mupirocin. In an aspect, a disclosed compounded composition comprising mupirocin, azithromycin, and ketoconazole can comprise from about 4.0% to about 6.0% w/w azithromycin. In an aspect, a disclosed compounded composition comprising mupirocin, azithromycin, and ketoconazole can comprise about 5.0% w/w azithromycin. In an aspect a disclosed compounded composition comprising mupirocin, azithromycin, and ketoconazole can comprise from about 4.0% to about 6.0% w/w ketoconazole. In an aspect, a disclosed compounded composition comprising mupirocin, azithromycin, and ketoconazole can comprise about 5.0% w/w ketoconazole. In an a disclosed compounded composition comprising mupirocin, azithromycin, and ketoconazole can comprise about 1.645% w/w mupirocin, about 5.0% w/w azithromycin, and about 5.0% w/w ketoconazole.

In an aspect, the formula presented below can be used to identify the approximate amount of powder from crushed ketoconazole tablets needed for 1 g of the compounded composition:

avg. tablet weight (g) $\times$ % of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets needed for 1 g of the compounded composition can be determined to be about 0.0775 g (or 77.5 mg).

avg. tablet weight (g) $\times$    % of a tablet needed =    amt. of powder from crushed tablets needed (g)

(0.3100 g)      (25.0%)      (0.0775 g)

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising mupirocin, azithromycin, and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, azithromycin, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, azithromycin, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 20

In an aspect, to make 1 g of the compounded composition, which has about 1.645% w/w mupirocin, about 5.0% w/w azithromycin, and about 5.0% w/w ketoconazole, about 0.8225 g of mupirocin 2.0% ointment, about 0.100 g of azithromycin for injection USP powder (500 mg azithromycin/1 g powder), and about 0.0775 g of powder from crushed ketoconazole tablets can be combined and mixed together according to a disclosed method described above.

Table 20 provides the approximate amount of mupirocin, azithromycin, and ketoconazole needed to make various amounts of the compounded composition.

TABLE 20

MUPIROCIN, AZITHROMYCIN, AND KETOCONAZOLE

| Compounded Composition (in grams) | Mupirocin (2.0% ointment) | Azithromycin (500 mg/1 g powder for | Ketoconazole (powder from crushed tablets) |
|---|---|---|---|
| 1 | 0.8225 g | 0.100 g | 0.0775 g |
| 4 | 3.29 g | 0.400 g | 0.31 g |
| 8 | 6.58 g | 0.800 g | 0.62 g |
| 25 | 20.5625 g | 2.5 g | 1.9375 g |
| 50 | 41.125 g | 5.0 g | 3.875 g |
| 240 | 197.4 g | 24.0 g | 18.6 g |
| 1500 | 1233.75 g | 150.0 g | 116.25 g |

As used in Example 20, the term "about" means a value falling within a range that is ±10% of the stated value. In an aspect, the skilled person can combine 0.8225 g±10% mupirocin 2.0% ointment (e.g., from about 0.74025 g-0.90475 g), 0.10 g±10% azithromycin powder (e.g., from about 0.09 g-0.11 g), and 0.0775 g±10% powder from crushed ketoconazole tablets (e.g., from about 0.06975 g-0.08525 g) and mix together according to a method described above to make about 1.0 g±10% of the compounded composition.

7. Miscellaneous
Mupirocin, Clindamycin or a Salt Thereof, Gentamicin or a Salt Thereof, and Econazole or a Salt Thereof Disclosed herein is method of making a compounded composition, the method comprising: mixing a therapeutically effective amount of mupirocin, a therapeutically effective of amount of clindamycin or a pharmaceutically acceptable salt thereof (e.g., phosphate), a therapeutically effective of amount of gentamicin or a pharmaceutically acceptable salt thereof (e.g., sulfate), and a therapeutically effective of amount of econazole or a pharmaceutically acceptable salt thereof (e.g., nitrate) to make a homogeneous compounded composition. A disclosed compounded composition can comprise a dry powder formulation or can comprise an ointment.

In an aspect, a disclosed method can comprise obtaining mupirocin, obtaining the clindamycin or a pharmaceutically acceptable salt thereof (e.g., phosphate), obtaining the gentamicin or a pharmaceutically acceptable salt thereof (e.g., sulfate), obtaining the econazole or a pharmaceutically acceptable salt thereof (e.g., nitrate), or a combination thereof. In an aspect, obtaining can comprise obtaining a bulk source of the mupirocin, obtaining a bulk source of the clindamycin or a pharmaceutically acceptable salt thereof (e.g., phosphate), obtaining a bulk source of the gentamicin or a pharmaceutically acceptable salt thereof (e.g., sulfate), obtaining a bulk source of econazole or a pharmaceutically acceptable salt thereof (e.g., nitrate), or a combination thereof.

Mupirocin is known to the art and is discussed supra. Clindamycin as well as pharmaceutically acceptable salts thereof are known to the art and are discussed supra. Gentamicin as well as pharmaceutically acceptable salts thereof are known to the art and are discussed supra. Econazole as well as pharmaceutically acceptable salts thereof are known to the art and are discussed supra.

In an aspect, a disclosed compounded composition comprising mupirocin, clindamycin or a salt thereof, gentamicin or a salt thereof, and econazole or a salt thereof can comprise from about 0.5% w/w to about 1.4% w/w, from about 0.6% w/w to about 1.3% w/w, from about 0.7% w/w to about 1.2% w/w, from about 0.7% w/w to about 1.1% w/w, from about 0.8% w/w to about 1.0% w/w, or from about 0.9% w/w to about 1.0% w/w mupirocin.

In an aspect, a disclosed compounded composition comprising mupirocin, clindamycin or a salt thereof, gentamicin or a salt thereof, and econazole or a salt thereof can comprise from about 0.01% w/w to about 0.08% w/w or from about 0.04% w/w and about 0.06% w/w clindamycin or a pharmaceutically acceptable salt thereof (e.g., phosphate). In an aspect, a disclosed compounded composition comprising mupirocin, clindamycin or a salt thereof, gentamicin or a salt thereof, and econazole or a salt thereof can comprise about 0.01% w/w, about 0.02% w/w, about 0.03% w/w, about 0.06% w/w, or about 0.07% w/w clindamycin or a pharmaceutically acceptable salt thereof (e.g., phosphate).

In an aspect, a disclosed compounded composition comprising mupirocin, clindamycin or a salt thereof, gentamicin or a salt thereof, and econazole or a salt thereof can comprise from about 0.01% w/w to about 0.05% w/w, from about 0.01% w/w to about 0.04% w/w, from about 0.01% w/w to about 0.03% w/w, or from about 0.015% w/w to about 0.025% w/w gentamicin or a pharmaceutically acceptable salt thereof (e.g., sulfate).

In an aspect, a disclosed compounded composition comprising mupirocin, clindamycin or a salt thereof, gentamicin or a salt thereof, and econazole or a salt thereof can comprise from about 0.1% w/w to about 0.6% w/w, from about 0.2% w/w to about 0.5% w/w, from about 0.2% w/w to about 0.4% w/w, or from about 0.025% w/w to about 0.035% w/w econazole or a pharmaceutically acceptable salt thereof (e.g., nitrate).

In an aspect, a disclosed compounded composition comprising mupirocin, clindamycin or a salt thereof, gentamicin or a salt thereof, and econazole or a salt thereof can comprise from about 0.9% w/w to 1% w/w mupirocin, from about 0.04% w/w to about 0.06% w/w clindamycin or a pharmaceutically acceptable salt thereof (e.g., phosphate), from about 0.01% w/w to about 0.03% w/w gentamicin or a pharmaceutically acceptable salt thereof (e.g., sulfate), and from about 0.2% to about 0.4% w/w econazole or a pharmaceutically acceptable salt thereof (e.g., nitrate). In an aspect, a disclosed compounded composition can comprise about 0.9% w/w mupirocin, about 0.05% w/w clindamycin or a pharmaceutically acceptable salt thereof (e.g., phosphate), about 0.02% w/w gentamicin or a pharmaceutically acceptable salt thereof (e.g., sulfate), and about 0.3% w/w econazole or a pharmaceutically acceptable salt thereof (e.g., nitrate).

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including anti-oxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition into a container and sealing the container. In an aspect, a container can be a container disclosed herein, such as, for example, a syringe. In an aspect, a disclosed method can comprise sterilizing the compounded composition.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, clindamycin or a pharmaceutically acceptable salt thereof (e.g., phosphate), gentamicin or a pharmaceutically acceptable salt thereof (e.g., sulfate), and econazole or a pharmaceutically acceptable salt thereof (e.g., nitrate) can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 21

In an aspect, to make 1 g of the compounded composition comprising about 0.9% w/w mupirocin, about 0.05% w/w clindamycin phosphate, about 0.02% w/w gentamicin sulfate, and about 0.3% w/w econazole nitrate, about 0.45 g of mupirocin 2.0% ointment, about 0.05 g of clindamycin phosphate 1.0% gel ointment, about 0.20 g gentamicin sulfate 0.1% ointment, and about 0.30 g econazole nitrate 1.0% cream can be combined and mixed together according to a method described above.

Table 21 provides the approximate amount of mupirocin, clindamycin phosphate, gentamicin sulfate, and econazole nitrate needed to make various amounts of the compounded composition.

TABLE 21

MUPIROCIN, CLINDAMYCIN PHOSPHATE, GENTAMICIN SULFATE, AND ECONAZOLE NITRATE

| Compounded Composition (in grams) | Mupirocin (2.0% ointment) | Clindamycin Phosphate (1.0% gel) | Gentamicin Sulfate (0.1% ointment) | Econazole Nitrate (1.0% cream) |
|---|---|---|---|---|
| 1 | 0.45 g | 0.05 g | 0.20 g | 0.30 g |
| 4 | 1.8 g | 0.2 g | 0.80 g | 1.2 g |
| 8 | 3.6 g | 0.4 g | 1.6 g | 2.4 g |
| 25 | 11.25 g | 1.25 g | 5.0 g | 7.5 g |
| 50 | 22.5 g | 2.5 g | 10.0 g | 15.0 g |
| 240 | 108.0 g | 12.0 g | 48.0 g | 72.0 g |
| 1500 | 675.0 g | 75.0 g | 300.0 g | 450.0 g |

As used in Example 21, the term "about" means a value falling within a range that is ±10% of the stated value. In an aspect, the skilled person can combine 0.45 g±10% mupirocin 2.0% ointment (e.g., from about 0.405 g-0.495 g), 0.05 g±10% clindamycin phosphate 1.0% gel (e.g., from about 0.045 g-0.055 g), 0.20 g±10% gentamicin sulfate 0.1% ointment (e.g., from about 0.18 g-0.22 g), and 0.30 g±10% econazole nitrate 1.0% ointment (e.g., from about 0.27 g-0.33 g) and mix together according to a method described above to make about 1.0 g±10% of the compounded composition.

Doxycycline or a Salt Thereof and Nystatin

Disclosed herein is method of making a compounded composition, the method comprising: mixing a therapeutically effective amount of doxycycline and a therapeutically effective amount of nystatin to make a homogeneous compounded composition. A disclosed compounded composition can comprise a dry powder formulation or can comprise an ointment.

In an aspect, a disclosed method can comprise obtaining the doxycycline or a pharmaceutically acceptable salt thereof, obtaining the nystatin, or a combination thereof. In an aspect, obtaining can comprise obtaining a bulk source of the doxycycline or a pharmaceutically acceptable salt thereof, obtaining a bulk source of the nystatin, or a combination thereof.

Doxycycline as well as pharmaceutically acceptable salts thereof are known to the art and are discussed supra. Nystatin is known to the art and is discussed supra.

In an aspect, the average weight of a doxycycline hyclate tablet can be about 0.2435 grams and can comprise about 100 mg of doxycycline.

In an aspect, the formula presented below can be used to identify the approximate amount of powder from crushed doxycycline hyclate tablets needed for 1 g of the compounded composition:

avg. tablet weight (g) x % of a tablet needed=amt. of powder from crushed tablets needed (g)

In an aspect, the average weight of a doxycycline hyclate tablet can be about 0.2435 grams and can comprise about 100 mg of doxycycline. Thus, In an aspect, using the above-identified formula, the amount of powder from crushed doxycycline hyclate tablets can be determined to be about 0.12175 g (or 121.75 mg).

average tablet weight × % of a tablet needed = amount of powder from crushed tables needed (g)

(0.2435 g)    (50.0%)    (0.12175 g)

In an aspect, a disclosed compounded composition comprising doxycycline or a salt thereof and nystatin can comprise from about 1.0% w/w to about 10.0% w/w or from about 2.0% w/w to about 9.0% w/w doxycycline or a pharmaceutically acceptable salt thereof. In an aspect, a disclosed compounded composition comprising doxycycline or a salt thereof and nystatin can comprise about 3.0% w/w, about 4.0% w/w, about 5.0% w/w, about 6.0% w/w, about 7.0% w/w, or about 8.0% w/w doxycycline or a pharmaceutically acceptable salt thereof. In an aspect, a disclosed compounded composition comprising doxycycline or a salt thereof and nystatin can comprise from about 50,000 to about 98,000 units per gram, from about 60,000 to about 90,000 units per gram, from about 70,000 to about 90,000 units per gram, and from about 80,000 to about 90,000 units per gram nystatin. In an aspect, a disclosed compounded composition comprising doxycycline or a salt thereof and nystatin can comprise from about 4.0% w/w to about 6.0% w/w doxycycline and from about 80,000 to about 90,000 units per gram nystatin. In an aspect, a disclosed compounded composition comprising doxycycline or a salt thereof and nystatin can comprise about 5.0% w/w doxycycline and about 87,825 units per gram nystatin.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising doxycycline or a salt thereof and nystatin into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising doxycycline or a salt thereof and nystatin.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, doxycycline or a pharmaceutically acceptable salt thereof and nystatin can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 22

In an aspect, to make 1 g of the compounded composition, which has about 5.0% w/w doxycycline and about 87,825 units per gram nystatin, about 0.12175 mg of powder from crushed doxycycline hyclate tablets and about 0.8782 g of nystatin can be combined and mixed together according to a method described above.

Table 22 provides the approximate amount doxycycline hyclate and nystatin needed to make various amounts of the compounded composition.

TABLE 22

DOXYCYCLINE HYCLATE AND NYSTATIN

| Compounded Composition (in | Doxycycline Hyclate (powder from crushed | Nystatin Powder (100,000 units/gram) |
|---|---|---|
| 1 | 0.12175 g | 0.8782 g |
| 4 | 0.487 g | 3.5128 g |
| 8 | 0.974 g | 7.0256 g |
| 25 | 3.04375 g | 21.955 g |
| 50 | 6.0875 g | 43.91 g |
| 240 | 29.22 g | 210.768 g |
| 1500 | 182.625 g | 1317.3 g |

As used in Example 22, the term "about" means a value falling within a range that is ±10% of the stated value. In an aspect, the skilled person can combine 0.12175 g±10% powder from crushed doxycycline hyclate tablets (e.g., from about 0.109575 g-0.133925 g) and 0.8782 g±10% nystatin powder (e.g., from about 0.79038 g-0.96602 g) and mix together according to a method described above to make about 1.0 g±10% of the compounded composition.

Tobramycin or Salt Thereof and Nystatin

Disclosed herein is method of making a compounded composition, the method comprising: mixing a therapeutically effective amount of tobramycin or a pharmaceutically acceptable thereof and a therapeutically effective amount of nystatin to make a homogeneous compounded composition. A disclosed compounded composition can comprise a dry powder formulation or can comprise an ointment.

In an aspect, a disclosed method can comprise obtaining the tobramycin or a pharmaceutically acceptable thereof, obtaining the nystatin, or a combination thereof. In an aspect, obtaining can comprise obtaining a bulk source of the tobramycin or a pharmaceutically acceptable thereof, obtaining a bulk source of the nystatin, or a combination thereof.

Tobramycin as well as pharmaceutically acceptable salts thereof are known to the art and are discussed supra. Nystatin is known to the art and is discussed supra.

In an aspect, a disclosed compounded composition comprising tobramycin or a salt thereof and nystatin can comprise from about 2.5% w/w to about 7.5% w/w tobramycin or a pharmaceutically acceptable salt thereof. In an aspect, a disclosed compounded composition comprising tobramycin or a salt thereof and nystatin can comprise about 5.0% w/w tobramycin or a pharmaceutically acceptable salt thereof. In an aspect, a disclosed compounded composition comprising tobramycin or a salt thereof and nystatin can comprise from about 800,000 units per gram to about 100,000 units per gram nystatin. In an aspect, a disclosed compounded composition comprising tobramycin or a salt thereof and nystatin can comprise about 92,500 units per gram nystatin. In an aspect, a disclosed compounded composition comprising tobramycin or a salt thereof and nystatin can comprise about 5.0% w/w tobramycin or a pharmaceutically acceptable salt thereof and about 92,500 units per gram nystatin.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising tobramycin or a salt thereof and nystatin into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising tobramycin or a salt thereof and nystatin.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, tobramycin or a pharmaceutically acceptable salt thereof and nystatin can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 23

In an aspect, to make 1 g of the compounded composition, about 0.075 g of tobramycin sulfate powder for injection USP and about 0.925 g of nystatin powder can be combined and mixed together according to a method described above.

Table 23 provides the approximate amount of tobramycin sulfate and nystatin needed to make various amounts of the compounded composition.

TABLE 23

| TOBRAMYCIN SULFATE AND NYSTATIN | | |
|---|---|---|
| Compounded Composition (in grams) | Tobramycin Sulfate (USP powder for | Nystatin Powder (100,000 units/ |
| 1 | 0.075 g | 0.925 g |
| 4 | 0.3 g | 3.7 g |
| 8 | 0.6 g | 7.4 g |
| 25 | 1.875 g | 23.125 g |
| 50 | 3.75 g | 46.25 g |
| 240 | 18.0 g | 222.0 g |
| 1500 | 112.5 g | 1387.5 g |

As used in Example 23, the term "about" means a value falling within a range that is ±10% of the stated value. In an aspect, the skilled person can combine 0.075 g±10% tobramycin sulfate for injection USP powder (e.g., from about 0.0675 g-0.0825 g) and 0.925 g±10% nystatin powder (e.g., from about 0.8325 g-1.0175 g) and mix together according to a method described above to make about 1.0 g±10% of the compounded composition.

Clobetasol Propionate and Fluconazole or Urea

Disclosed herein is method of making a compounded composition, the method comprising: mixing a therapeutically effective amount of clobetasol propionate and a therapeutically effective amount of fluconazole or urea to make a homogeneous compounded composition. A disclosed compounded composition can comprise a dry powder formulation or can comprise an ointment.

In an aspect, a disclosed method can comprise obtaining the clobetasol propionate, obtaining the fluconazole, obtaining the urea, or a combination thereof. In an aspect, obtaining can comprise obtaining a bulk source of the clobetasol propionate, obtaining a bulk source of the fluconazole, obtaining a bulk source of the urea, or a combination thereof.

Clobetasol propionate is known to the art and is discussed supra. Fluconazole is known to the art and is discussed supra. Urea is known to the art and is discussed supra.

In an aspect, a disclosed compounded composition comprising clobetasol propionate and fluconazole can comprise from about 0.02% w/w to about 0.10% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and fluconazole can comprise from about 1.0% w/w to about 5.0% w/w, from about 2.0% w/w to about 4.0% w/w, from about 2.0% w/w to about 3.0% w/w, or from about 2.0% w/w to about 4.0% w/w fluconazole. In an aspect, a disclosed compounded composition comprising clobetasol propionate and fluconazole can comprise from about 0.02% w/w to about 0.06% w/w clobetasol propionate and from about 2.0% w/w to about 4.0% w/w fluconazole. In an aspect, a disclosed compounded composition comprising clobetasol propionate and fluconazole can comprise about 0.0485% w/w clobetasol propionate and about 3.0% w/w fluconazole. In an aspect, clobetasol propionate can comprise clobetasol propionate 0.05% ointment.

In an aspect, a disclosed compounded composition comprising clobetasol propionate and urea can comprise from about 0.02% w/w to about 0.10% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and urea can comprise from about 10.0% w/w to about 60.0% w/w, from about 20.0% w/w to about 50.0% w/w, from about 30.0% w/w to about 50.0% w/w, from about 30.0% w/w to about 40.0% w/w, or from about 40.0% w/w to about 50.0% w/w urea. In an aspect, a disclosed compounded composition comprising clobetasol propionate and urea can comprise from about 0.02% w/w to about 0.055% w/w clobetasol propionate and from about 30.0% to about 50.0% w/w urea. In an aspect, a disclosed compounded composition comprising clobetasol propionate and urea can comprise from about 0.02% to about 0.04% w/w clobetasol propionate and from about 30.0% to about 50.0% w/w urea. In an aspect, a disclosed compounded composition comprising clobetasol propionate and urea can comprise about 0.03% w/w clobetasol propionate and about 40.0% w/w urea. In an aspect, clobetasol propionate can comprise clobetasol propionate 0.05% ointment.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising clobetasol propionate and fluconazole or urea into a container and sealing the container. In an aspect, a container can be a container disclosed herein, such as, for example, a syringe. In an aspect, a disclosed method can comprise sterilizing the compounded composition comprising clobetasol propionate and fluconazole or urea.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, clobetasol propionate and fluconazole or urea can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 24

In an aspect, to make 1.0 g of the compounded composition comprising about 0.0485% w/w clobetasol propionate and about 3.0% w/w fluconazole, about 0.97 g of clobetasol propionate 0.05% ointment and 0.03 g of powder from crushed fluconazole tablets can be combined and mixed together according to a method described above.

Table 24 provides the approximate amount of clobetasol propionate and fluconazole needed to make various amounts of the compounded composition.

TABLE 24

CLOBETASOL PROPIONATE AND FLUCONAZOLE

| Compounded Composition (in grams) | Clobetasol Propionate (0.05% ointment) | Fluconazole (powder from crushed |
|---|---|---|
| 1 | 0.97 g | 0.03 g |
| 4 | 3.88 g | 0.12 g |
| 8 | 7.76 g | 0.24 g |
| 25 | 24.25 g | 0.75 g |
| 50 | 48.5 g | 1.5 g |
| 240 | 232.8 g | 7.2 g |
| 1500 | 1455.0 g | 45.0 g |

As used in Example 24, the term "about" means a value falling within a range that is ±10% of the stated value. In an aspect, the skilled person can combine 0.97 g±10% clobetasol propionate 0.05% ointment (e.g., from about 0.873 g-1.067 g) and 0.03 g±10% powder from crushed fluconazole tablets (e.g., from about 0.027 g-0.33 g) and mix together according to a method described above to make about 1.0 g±10% of the compounded composition.

Example 25

In an aspect, to make 1.0 g of the compounded composition, which has about 0.03% w/w clobetasol propionate and about 40.0% w/w urea, about 0.60 g of clobetasol propionate 0.05% ointment and about 0.40 g of urea USP 99.6 powder can be combined and mixed together according to a method described above.

Table 25 provides the approximate amount of clobetasol propionate and urea needed to make various amounts of the compounded composition.

TABLE 25

CLOBETASOL PROPIONATE AND UREA

| Compounded Composition (in grams) | Clobetasol Propionate (0.05% ointment) | Urea (USP Powder) |
|---|---|---|
| 1 | 0.60 g | 0.40 g |
| 4 | 2.4 g | 1.6 |
| 8 | 4.8 g | 3.2 g |
| 25 | 15.0 g | 10.0 g |
| 50 | 30.0 g | 20.0 g |
| 240 | 144.0 g | 96.0 g |
| 1500 | 900.0 g | 600.0 g |

As used in Example 25, the term "about" means a value falling within a range that is ±10% of the stated value. In an aspect, the skilled person can combine 0.60 g±10% clobetasol propionate 0.05% ointment (e.g., from about 0.54 g-0.66 g) and 0.40 g±10% urea USP powder (e.g., from about 0.36 g-0.44 g) and mix together according to a method described above to make about 1.0 g±10% of the compounded composition.

Clobetasol Propionate and Ketoconazole

Disclosed herein is method of making a compounded composition, the method comprising: mixing a therapeutically effective amount of clobetasol propionate and a therapeutically effective of amount of ketoconazole to make a homogeneous compounded composition. A disclosed compounded composition can comprise a dry powder formulation or can comprise an ointment.

In an aspect, a disclosed method can comprise obtaining clobetasol propionate, obtaining the ketoconazole, or a combination thereof. In an aspect, obtaining can comprise obtaining a bulk source of the clobetasol propionate, obtaining a bulk source of the ketoconazole, or a combination thereof.

Clobetasol propionate is known to the art and is discussed supra. Ketoconazole is known to the art and is discussed supra.

The formula presented below can be used to identify the approximate amount of powder from crushed ketoconazole tablets needed for 1 gram of the compounded composition:

avg. tablet weight (g) x % of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets can be determined to be about 0.11625 g (or 116.25 mg).

| average tablet weight× | % of a tablet needed = | amount of powder from crushed tablets needed (g) |
|---|---|---|
| (0.310 g) | (37.5%) | (0.11625 g) |

In an aspect, a disclosed compounded composition comprising clobetasol propionate and ketoconazole can comprise from about 0.02% w/w to about 0.1% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and ketoconazole can comprise from about 3.0% w/w to about 12.0% w/w, from about 4.0% w/w to about 10.0% w/w, from about 5.0% w/w to about 10.0% w/w, or from about 6.0% w/w to about 8.0% w/w ketoconazole. In an aspect, a disclosed compounded composition comprising clobetasol propionate and ketoconazole can comprise from about 0.04% w/w to about 0.05% w/w clobetasol propionate and from about 6.0% w/w to about 8.0% w/w ketoconazole. In an aspect, a disclosed compounded composition comprising clobetasol propionate and ketoconazole can comprise about 0.044% clobetasol propionate and about 7.5% w/w ketoconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising clobetasol propionate and ketoconazole into a container and sealing the container. In an aspect, a container can be a container disclosed herein, such as, for example, a syringe. In an aspect, a disclosed method can comprise sterilizing the compounded composition comprising clobetasol propionate and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, clobetasol propionate and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 26

In an aspect, to make 1 g of the compounded composition, which has about 0.044% w/w clobetasol propionate and about 7.5% w/w ketoconazole, about 0.8838 g of clobetasol propionate 0.05% ointment and about 0.11625 mg of powder from crushed ketoconazole tablets can be combined and mixed together according to a method described above.

Table 26 provides the approximate amount of clobetasol propionate and ketoconazole needed to make various amounts of the compounded composition.

TABLE 26

CLOBETASOL PROPIONATE AND KETOCONAZOLE

| Compounded Composition (in grams) | Clobetasol Propionate (0.05% ointment) | Ketoconazole (powder from crushed |
|---|---|---|
| 1 | 0.8838 g | 0.11625 g |
| 4 | 3.5352 g | 0.465 g |
| 8 | 7.0704 g | 0.93 g |
| 25 | 22.095 g | 2.90625 g |
| 50 | 44.19 g | 5.8125 g |
| 240 | 212.112 g | 27.9 g |
| 1500 | 1325.7 g | 174.375 g |

As used in Example 26, the term "about" means a value falling within a range that is ±10% of the stated value. In an aspect, the skilled person can combine 0.8838 g±10% clobetasol propionate 0.05% ointment (e.g., from about 0.79542 g-0.97218 g) and 0.11625 g±10% powder from crushed ketoconazole tablets (e.g., from about 0.104625 g-0.127875 g) and mix together according to a method described above to make about 1.0 g±10% of the compounded composition.

Ketoconazole, an Excipient Base Powder, and Xylitol

Disclosed herein is a method of making a compounded composition, the method comprising: mixing a therapeutically effective amount of ketoconazole, a sufficient amount of an excipient base powder comprising a blend of micronized xylitol and poloxamers, and a sufficient amount of xylitol to make a homogeneous compounded composition.

In an aspect, a disclosed method can comprise obtaining ketoconazole, obtaining an excipient base powder, obtaining xylitol, or a combination thereof. In an aspect, obtaining can comprise obtaining a bulk source of ketoconazole, obtaining a bulk source of an excipient base powder, obtaining a bulk source of xylitol, or a combination thereof.

Ketoconazole is known to the art and is discussed supra. Xylitol is known to the art and is discussed supra.

In an aspect of a disclosed compounded composition, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder. In an aspect, XyliFos™ excipient base powder can comprise xylitol, poloxamer 407, hydroxylpropyl betadex, and epigallocatechin gallate. In an aspect, an excipient base powder can be obtained from a bulk source. In an aspect, an excipient base powder can be commercially available.

In an aspect, the formula presented below can be used to identify the approximate amount of powder from crushed commercially available ketoconazole tablets needed for 1 g of the compounded composition:

avg. tablet weight (g) x % of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets needed for 1 g of the compounded composition can be determined to be about 0.465 g (or 465 mg).

avg. tablet weight (g)× % of a tablet needed =  amt. of powder from crushed tablets needed (g)

(0.3100 g)        (150.0%)        (0.465 g)

In an aspect, a disclosed compounded composition comprising ketoconazole, an excipient base powder, and xylitol can comprise from about 10.0% w/w to about 50.0% w/w, from about 20.0% w/w to about 40.0% w/w, or from about 25.0% w/w to about 35.0% w/w ketoconazole. In an aspect, a disclosed compounded composition comprising ketoconazole, an excipient base powder, and xylitol can comprise a weight ratio of LoxaSperse™ to xylitol of about 1:1, about 1:2, about 1:3, about 1:4, about 1:5, about 1:6, about 1:7, from about 1:1 to about 1:7, from about 1:2 to about 1:6, or from about 1:4 to about 1:5. In an aspect, the weight ratio of LoxaSperse™ to xylitol is about 1:4.35. In an aspect, a disclosed compounded composition comprising ketoconazole, an excipient base powder, and xylitol can comprise about 30% w/w ketoconazole and a weight ratio of LoxaSperse™ to xylitol of about 1:4 to about 1:5. In an aspect, a disclosed compounded composition comprising ketoconazole, an excipient base powder, and xylitol can comprise about 30% w/w ketoconazole and a weight ratio of LoxaSperse™ to xylitol of about 1:4.35.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional anti-infective agents with the compounded composition. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra. In an aspect, a disclosed method can comprise obtaining the additional anti-infective agent. In an aspect, obtaining can comprise obtaining a bulk source of the anti-infective agent.

In an aspect, a disclosed method can comprise packaging the compounded composition comprising ketoconazole, an excipient base powder, and xylitol into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising ketoconazole, an excipient base powder, and xylitol.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, ketoconazole, an excipient base powder, and xylitol can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 27

In an aspect, to make 1 g of the compounded composition, about 0.465 g of powder from crushed ketoconazole tablets, about 0.1 g of an excipient base powder (e.g., LoxaSperse™), and about 0.435 g of xylitol can be combined and mixed together according to a method described above.

Table 27 provides the approximate amount of ketoconazole, excipient base powder, and xylitol needed to make various amounts of the compounded composition.

TABLE 27

KETOCONAZOLE, AN EXCIPIENT BASE POWDER, AND XYLITOL

| Compounded Composition (in grams) | Ketoconazole (powder from crushed tablets) | Excipient Base Powder (dry powder) | Xylitol |
|---|---|---|---|
| 1 | 0.465 g | 0.1 g | 0.435 g |
| 4 | 1.86 g | 0.4 g | 1.74 g |
| 8 | 3.72 g | 0.8 g | 3.48 g |
| 25 | 11.625 g | 2.5 g | 10.875 g |
| 50 | 23.25 g | 5.0 g | 21.75 g |
| 240 | 111.6 g | 24.0 g | 104.4 g |
| 1500 | 697.5 g | 150.0 g | 652.5 g |

As used in Example 27, the term "about" means a value falling within a range that is ±10% of the stated value. In an aspect, the skilled person can add 0.465 g±10% powder from crushed ketoconazole tablets (e.g., from about 0.4185 g-0.5115 g), 0.1 g±10% excipient base powder (e.g., from about 0.09 g-0.11 g), and 0.435 g±10% xylitol (e.g., from about 0.3915 g-0.4785 g) can be combined and mixed together according to a method described above to make about 1.0 g±10% of the compounded composition.

E. Methods of Treating or Preventing an Infection Using a Compounded Composition Disclosed herein is a method of treating or preventing an infection, the method comprising: applying to the skin of a subject a compounded composition, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

Disclosed herein is a method of treating or preventing an infection, the method comprising: preparing a homogeneous compounded composition comprising (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein; and applying to the skin of a subject the compounded composition.

In an aspect, a disclosed method can comprise orally administering to the subject a pharmaceutical composition comprising one or more anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, a disclosed method can comprise pre-treating the subject's hands. In an aspect, a subject can apply a liquid skin cleanser (e.g., Hibiclens) to his hands. Using water, the subject can wash his hands with the Hibiclens for at least 5 seconds, at least 10 seconds, at least 15 seconds, at least 20 seconds, or at least 30 seconds.

In an aspect, a disclosed method can comprise repeating the applying step until the bacterial infection, suspected bacterial infection, the fungal infection, or the suspected fungal infection is eradicated or appears to be eradicated. In an aspect, a disclosed method can comprise repeating the applying step twice daily until the bacterial infection, suspected bacterial infection, the fungal infection, or the suspected fungal infection is eradicated or appears to be eradicated. In an aspect, a disclosed method can comprise repeating the applying step twice daily for a pre-determined amount of time. In an aspect, the pre-determined amount of time can comprise at least 5 days, at least 7 days, at least 10 days, at least 14 days, at least 21 days, at least 30 days, or more than 30 days. In an aspect, the pre-determined amount can comprise an amount of time lasting at least 5-7 days, at least 7-10 days, at least 10-14 days, at least 14-21 days, at least 21-30 days, at least 30 days, or more than 30 days.

In an aspect, applying the compounded composition can comprise contacting the compounded composition with the subject's skin until the compounded composition has been absorbed or substantially absorbed by the skin. In an aspect, applying can comprise using a sterile applicator to contact the compounded composition with the skin. In an aspect, applying can comprise contacting about 2 g to about 6 g, or about 3 g to about 5 g, or about 4 g of the compounded composition with the subject's skin. In an aspect, a disclosed compounded composition can be applied to skin in conjunction with an occlusive dressing. In an aspect, a disclosed method can comprise applying a covering to the skin affected by the infection.

In an aspect, a disclosed compounded composition can be mixed with a diluent to form a solution or suspension and then applied to the subject's skin. Diluents are discussed supra. In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL. In an aspect, a disclosed method can comprise cleaning and drying a mixing container.

In an aspect, a disclosed compounded composition can be applied to the subject's skin as a dry powder or as an ointment. In an aspect, a disclosed compounded composition can be applied to the subject's skin as a cream, or lotion, or emulsion, or gel. For example, the compounded composition may comprise a compounded ointment as described herein. any disclosed compounded composition formulated in an ointment.

In one embodiment, a method of treating an infection comprises applying to infected skin a compounded composition ointment comprising a therapeutically effective amount of mupirocin ointment (e.g., mupirocin 2% ointment) and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise anti-infective for injection powder compounded with the mupirocin ointment.

In one embodiment, a method of treating an infection comprises applying to infected skin a compounded composition ointment comprising a therapeutically effective amount of mupirocin ointment (e.g., mupirocin 2% ointment) and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise anti-infective for injection powder compounded with the mupirocin ointment. For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof.

In one embodiment, a method of treating an infection comprises applying to infected skin a compounded composition ointment comprising a therapeutically effective amount of mupirocin ointment (e.g., mupirocin 2% ointment) and a therapeutically effective amount of an antifungal agent comprising one or more antifungals or pharmaceutically acceptable salt thereof selected from ketoconazole, voriconazole, amphotericin B, or combinations thereof. All or a portion of the antifungal agent may comprise anti-infective for injection powder compounded with the mupirocin ointment.

In one embodiment, a method of treating an infection comprises applying to infected skin a compounded composition ointment comprising a therapeutically effective amount of mupirocin ointment (e.g., mupirocin 2% ointment), a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof. All or a portion of the antibacterial agent may comprise anti-infective for injection powder compounded with the mupirocin ointment. For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof. All or a portion of the antifungal agent may comprise anti-infective for injection powder compounded with the mupirocin ointment.

In one embodiment, a method of treating an infection comprises applying to infected skin a compounded composition ointment comprising a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise anti-infective for injection powder compounded with the mupirocin ointment. For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof. All or a portion of the antifungal agent may comprise anti-infective for injection powder compounded with the mupirocin ointment. For example, ketoconazole may comprise crushed tablets of ketoconazole and the one or more antifungals or pharmaceutically acceptable salt thereof selected from For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof may be obtained from powder for injection formats.

In an aspect, the subject can be diagnosed with or can be suspected of having a bacterial infection or a fungal infection that affects the subject's skin. In an aspect, the subject can have diabetes, can be obese, can be immunocompromised, can be non-ambulatory, or can have poor blood flow, or a combination thereof. In an aspect, the subject can routinely wear thick socks or wear heavy boots.

In an aspect, a disclosed method can comprise preparing a disclosed compounded composition. Disclosed and discussed supra are methods of preparing a disclosed compounded composition, such as, for example, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

In an aspect, a disclosed method of treating or preventing an infection can comprise modifying one or more aspect of the disclosed method. For example, in an aspect, a disclosed method can comprise changing or altering the amount of the disclosed compounded composition applied to a subject's skin, or by changing the frequency of the subject's use of the compounded composition, or by changing the duration of time that the subject uses the compounded composition, or by substituting one compounded composition for another compounded composition, or a combination thereof.

F. Methods of Treating or Preventing a Foot Infection Using a Compounded Composition Disclosed herein is a method of treating or preventing a foot infection, the method comprising: (i) adding a compounded composition to water contained within a footbath; (ii) agitating the water contained within the footbath; and (iii) contacting the agitated water with at least a part of one or both feet of a subject.

Disclosed herein is a method of treating or preventing a foot infection, the method comprising: (i) agitating water contained within a footbath; (ii) adding a compounded composition to the water contained with the footbath; and (iii) contacting the agitated water with at least a part of one or both feet of a subject.

Disclosed herein is a method of treating or preventing a foot infection, the method comprising: (i) mixing a compounded composition with a diluent to create a solution or suspension; (ii) adding the solution or suspension to water contained within a footbath; (iii) agitating the water contained within the footbath; and (iv) contacting the agitated water with at least part of one or both feet of a subject.

Disclosed herein is a method of treating or preventing a foot infection, the method comprising: (i) mixing a compounded composition with a diluent to create a solution or suspension; (ii) agitating water contained within a footbath; (iii) adding the solution or suspension to the water contained within the footbath; and (iv) contacting the agitated water with at least part of one or both feet of a subject.

Disclosed herein is a method of treating or preventing a foot infection, the method comprising: (i) adding a compounded composition to water contained within a footbath; (ii) agitating the water contained within the footbath; and (iii) contacting the agitated water with at least a part of one or both feet of a subject, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

Disclosed herein is a method of treating or preventing a foot infection, the method comprising: (i) agitating water contained within a footbath; (ii) adding a compounded composition to the water contained within the footbath; and (iii) contacting the agitated water with at least a part of one or both feet of a subject. The compounded composition may be any compounded composition, e.g., compounded ointment, described herein.

Disclosed herein is a method of treating or preventing a foot infection, the method comprising: (i) mixing a compounded composition with a diluent to create a solution or suspension; (ii) adding the solution or suspension to water contained within a footbath; (iii) agitating the water contained within the footbath; and (iv) contacting the agitated water with at least part of one or both feet of a subject, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

Disclosed herein is a method of treating or preventing a foot infection, the method comprising: (i) mixing a compounded composition with a diluent to create a solution or suspension; (ii) agitating water contained within a footbath; (iii) adding the solution or suspension to the water contained within the footbath; and (iv) contacting the agitated water with at least part of one or both feet of a subject, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

In an aspect, the subject can have diabetes, can be obese, can be immunocompromised, can be non-ambulatory, or can have poor blood flow, or a combination thereof. In an aspect, the subject can routinely wear thick socks or wear heavy boots. In an aspect, the subject has been diagnosed with or is suspected of having a bacterial infection that affects at least part of one or both feet. In an aspect, the subject has been diagnosed with or is suspected of having a bacterial infection and a fungal infection that affect at least part of one or both feet. In an aspect, the subject has been diagnosed with or is suspected of having a fungal infection that affects at least part of one or both feet.

In an aspect, a disclosed method can comprise orally administering to the subject a pharmaceutical composition comprising one or more anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, adding a disclosed compounded composition to the water contained within a footbath can comprise adding to the water between about 10 g to about 40 g of a disclosed compounded composition, or about 20 g to about 30 g of a disclosed compounded composition, or about 25 g of a disclosed compounded composition.

In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL.

In an aspect, a disclosed method can comprise adding the diluent to the water contained in the footbath. In an aspect, the diluent can comprise sodium hypochlorite. In an aspect, the diluent can comprise Dakin's solution. In an aspect, the amount of diluent can be about 20 mL to about 60 mL, or about 30 to about 50 mL, or about 20 mL, or about 30 mL, or about 40 mL, or about 50 mL, or about 60 mL.

In an aspect, adding the solution or suspension comprising the compounded composition and the diluent can be added to the footbath already having water, thereby increasing the water level in the footbath.

In an aspect, a disclosed method can comprise heating the water contained within the footbath. In an aspect, a disclosed method can comprise agitating the water contained within the footbath. In an aspect, a footbath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the footbath. Motors and agitators are known to the art. In an aspect, mechanical agitation can serve to distribute the compounded composition, the diluent, or the solution or suspension comprising the compounded composition and the diluent throughout the water contained within the footbath. Heating agents and/or means to heat water in a compartment are known to the art.

In an aspect of a disclosed method, a disclosed compound composition can be added to the water contained within the footbath while the water is being heated. In an aspect of a disclosed method, a disclosed compound composition can be added to the water contained within the footbath while the water is being agitated.

In an aspect, agitation can ensure dissolution of the compounded composition or the dissolution of solution or suspension comprising the compounded composition.

In an aspect, agitation can ensure optimal contact of the compounded composition with at least a part of the subject's foot or feet.

In an aspect, a disclosed method can comprise repeating daily steps (i)-(iii) or steps (i)-(iv). In an aspect, a disclosed method can comprise repeating daily steps (i)-(iii) or steps (i)-(iv) until the bacterial infection, suspected bacterial infection, the fungal infection, or the suspected fungal infection is eradicated or appears to be eradicated. In an aspect, a disclosed method can comprise repeating twice daily the applying step for a pre-determined amount of time. In an aspect, the pre-determined amount of time can comprise at least 5 days, at least 7 days, at least 10 days, at least 14 days, at least 21 days, at least 30 days, or more. In an aspect, the pre-determined amount can comprise an amount of time lasting at least 5-7 days, at least 7-10 days, at least 10-14 days, at least 14-21 days, at least 21-30 days, or at least 30 days.

In an aspect, contacting can comprise placing at least part of one or both feet of the subject in the footbath. In an aspect, contacting can comprise placing at least part of one or both feet of the subject in the footbath for about 5 to about 15 minutes. In an aspect, contacting can comprise placing at least part of one or both feet of the subject in the footbath for about 10 minutes.

In an aspect, the method can comprise removing the compounded composition from a container, such as, for example, a tube, a packet, a capsule, a syringe, a vial, etc., prior to adding the compounded composition to the water. In an aspect, the method can comprise removing the compounded composition from a container, such as, for example, a tube, a packet, a capsule, a syringe, a vial, etc., prior to adding the composition to the diluent. In an aspect, a capsule can be broken apart and the contents of the capsule can be added to the water in the footbath. In an aspect, an intact capsule can be added to the water in the footbath.

In an aspect, a disclosed method can comprise emptying the water from the footbath. In an aspect, a disclosed method can comprise cleaning the footbath. In an aspect, a disclosed method can comprise drying the footbath.

In an aspect, a disclosed method can comprise preparing a disclosed compounded composition. Methods of preparing a disclosed compounded composition are discussed supra.

In an aspect, a disclosed method of treating or preventing a foot infection can comprise modifying one or more aspect of the disclosed method. For example, in an aspect, a method can be altered by changing the amount of a disclosed compounded composition added to a footbath, by changing the frequency of the subject's use of the footbath, or by changing the duration of time that the subject's foot or feet contact the water contained within the footbath, or by substituting one disclosed compounded composition for another disclosed compounded composition, or a combination thereof.

In various aspects, a method of treating or preventing an infection, such as a foot infection, may comprise making or administering any of the disclosed compounded compositions to an affected skin surface of a subject. In some aspects, the compounded composition comprises a footbath composition for application to a foot of a subject. In one aspect, any of the disclosed compounded compositions may be administered in a footbath solution. For example, added into a mixing container along with a suitable amount of diluent.

The composition may be provided in a syringe, for example, for ease of addition with the diluent. The contents (e.g., 25 g) may be added to a suitable amount of diluent, as described herein, and mixed, e.g., in a mixing container. The amount of diluent may be about 15 ml diluent per tablespoon of the ointment. Other ratios may be used, e.g., between about 10 ml and about 50 ml, about 10 ml and about 40 ml, about 10 ml and about 30 ml, about 10 ml and about 20 ml, about 10 ml and about 15 ml, about 15 ml and about 50 ml, about 15 ml and about 40 ml, about 15 ml and about 30 ml, about 10 ml and about 25 ml, about 15 ml and about 20 ml, about 20 ml and about 50 ml, about 20 ml and about 40 ml, about 20 ml and about 30 ml, or about 20 ml and about 25 ml. Furthermore, the compounded composition ointment may be formulated with higher or lower concentrations of actives in the ointment and amounts of the compounded composition ointment added to diluent for administration may thereby adjusted accordingly. Mixing may include shaking or stirring to form a footbath solution. In a further aspect, the footbath solution may be further agitated. In one aspect, the mixing container comprises a footbath. In another aspect, the contents of the mixing container may be added to a footbath. Administering the footbath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily.

In various aspects, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

Disclosed herein is a compounded composition comprising a therapeutically effective amount of mupirocin, a therapeutically effective amount of azithromycin, and a therapeutically effective amount of ketoconazole. A disclosed compounded composition comprising mupirocin, azithromycin, and ketoconazole can comprise a dry powder formulation or can comprise an ointment.

In an aspect, a disclosed compounded composition comprising mupirocin, azithromycin, and ketoconazole can comprise from about 1.0% w/w to about 3.0% w/w mupirocin. In an aspect, a disclosed compounded composition comprising mupirocin, azithromycin, and ketoconazole can comprise about 1.645% w/w mupirocin. In an aspect, a disclosed compounded composition comprising mupirocin, azithromycin, and ketoconazole can comprise from about 4.0% w/w to about 6.0% w/w azithromycin. In an aspect, a disclosed compounded composition comprising mupirocin, azithromycin, and ketoconazole can comprise about 5.0% w/w azithromycin. In an aspect, a disclosed compounded composition comprising mupirocin, azithromycin, and ketoconazole can comprise from about 4.0% w/w to about 6.0% w/w ketoconazole. In an aspect, a disclosed compounded composition comprising mupirocin, azithromycin, and ketoconazole can comprise about 5.0% w/w ketoconazole. In an aspect, a disclosed compounded composition comprising mupirocin, azithromycin, and ketoconazole can comprise about 1.645% w/w mupirocin, about 5.0% w/w azithromycin, and about 5.0% w/w ketoconazole.

In various aspects, a disclosed composition to treat or prevent an infection, such as a foot infection, includes a footbath composition. The footbath composition may be or be prepared with suitable diluent to form a footbath solution, which may be a mixture, emulsion, solution, suspension, etc. In some aspects, a footbath solution may comprise a footbath composition comprising between about 0.1 g and about 1.0 g, about 0.1 g to 0.8 g, about 0.1 g and about 0.5 g, about 0.1 g and about 0.3 g, about 0.2 g and about 0.8 g, about 0.2 g and about 0.5 g, about 0.2 g and about 0.3 g, or about 0.5 g and about 0.8 g doxycycline; between about 10 g and about 40 g, about 10 g to 30 g, about 10 g and about 25 g, about 10 g and about 15 g, about 20 g and about 40 g, about 20 g and about 30 g, about 20 g and about 25 g, or about 25 g and about 35 g mupirocin 2% ointment or equivalent mupirocin; between about 5 g and about 35 g, about 5 g to 20 g, about 5 g and about 15 g, about 10 g and about 35 g, about 10 g and about 20 g, about 10 g and about 15 g, about 15 g and about 35 g, or about 15 g and about 25 g nystatin topical powder in a suitable amount of diluent, as described herein. In one aspect, the footbath solution includes three 100 mg capsules of doxycycline (0.3 g of doxycycline), one 22 g tube of mupirocin 2% ointment (440 mg of mupirocin), and one 15 g container of nystatin topical powder (15 g of nystatin powder) in a suitable volume of diluent. In various aspects, additional active ingredients may be added to the footbath.

In various aspects, a method of treating or preventing an infection, such as a foot infection, may comprise making administering any of the disclosed footbath compositions or solutions to a subject. For example, a footbath composition may comprise three 100 mg capsules of doxycycline (0.3 g of doxycycline), one 22 g tube of mupirocin 2% ointment (440 mg of mupirocin), and one 15 g container of nystatin topical powder (15 g of nystatin powder) and may be added into a mixing container along with a suitable amount of diluent. The contents may be mixed, e.g., shaken or stirred, to form a footbath solution. In a further aspect, the footbath solution may be further agitated. In one aspect, the mixing container comprises a footbath. In another aspect, the contents of the mixing container may be added to a footbath. Administering the footbath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily. In one aspect a 30 day supply may include ninety 100 mg capsules of doxycycline (9 g doxycycline); thirty 22 g tubes of mupirocin 2% ointment (660 g of mupirocin); and thirty 15 g containers of nystatin topical powder (450 g of nystatin powder).

In various aspects, the method of treating or preventing an infection, such as a foot infection, may include making or administering any of the above footbath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

In various aspects, the composition to treat or prevent an infection, such as a foot infection, includes the compounded composition as described herein. The compounded composition may comprise a footbath composition that may be or be prepared with suitable diluent to form a footbath solution, which may be a mixture, emulsion, solution, suspension, etc. as described herein. In some aspects, a footbath solution may comprise a footbath composition comprising compounded powder of multiple medications, which may be provided in a capsule, comprising between about 0.1 g and about 1.0 g, about 0.1 g to 0.8 g, about 0.1 g and about 0.5 g, about 0.1 g and about 0.3 g, about 0.2 g and about 0.8 g, about 0.2 g and about 0.5 g, about 0.2 g and about 0.3 g, or about 0.5 g and about 0.8 g doxycycline; between about 10 g and about 40 g, about 10 g to 30 g, about 10 g and about 25 g, about 10 g and about 15 g, about 20 g and about 40 g, about 20 g and about 30 g, about 20 g and about 25 g, or about 25 g and about 35 g mupirocin 2% ointment or equivalent mupirocin; and between about 5 g and about 35 g, about 5 g to 20 g, about 5 g and about 15 g, about 10 g and about 35 g, about 10 g and about 20 g, about 10 g and about 15 g, about 15 g and about 35 g, or about 15 g and about 25 g nystatin topical powder. The footbath solution may comprise the footbath composition in a suitable volume of diluent, as described herein. In one aspect, the footbath composition comprises a capsule containing about 100 mg doxycycline, about 30 mg mupirocin, and about 30 mg clotrimazole. In a further aspect, the footbath solution comprises the contents of the capsule mixed in a suitable volume of diluent. In various aspects, additional active ingredients may be added to the footbath.

In one aspect, a method of treating or preventing a foot infection, such as a foot infection, may comprise making or administering any of the above footbath compositions or solutions. In one example, the contents of a capsule may be added to a mixing container along with a suitable amount of diluent. The contents may be mixed, e.g., shaken or stirred, to form a footbath solution. In a further aspect, the footbath solution may be further agitated. In one aspect, the mixing container comprises a footbath. In another aspect, the contents of the mixing container may be added to a footbath. Administering the footbath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily.

In various aspects, the method of treating or preventing and infection, such as a foot infection, may include making or administering any of the above footbath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

G. Methods of Treating or Preventing an Infection Using an Intranasally Administered Compounded Composition Disclosed herein is a method of treating or preventing an infection, the method comprising: (i) intranasally administering to a subject a solution or suspension comprising a compounded composition. Disclosed herein is a method of treating or preventing an infection, the method comprising: (i) mixing a compounded composition with a diluent to create a solution or suspension; and (ii) intranasally administering to a subject the solution or suspension.

Disclosed herein is a method of treating or preventing an infection, the method comprising: (i) intranasally administering to a subject a solution or suspension comprising a compounded composition, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

Disclosed herein is a method of treating or preventing an infection, the method comprising: (i) mixing a compounded composition with a diluent to create a solution or suspension; and (ii) intranasally administering to a subject the solution or suspension, wherein the compounded composition comprises (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional anti-infectives according to any of the compounded compositions described herein.

In an aspect, the subject can have diabetes, can be obese, can be immunocompromised, can be non-ambulatory, or can have poor blood flow, or a combination thereof. In an aspect, the subject has been diagnosed with or can be suspected of having (i) cancer that affects at least a part of the respiratory tract, (ii) emphysema, (iii) pneumonia, (iv) bronchitis, (v) tuberculosis, (vi) asthma, or (vii) a combination thereof. In an aspect, the subject has been diagnosed with or is suspected of having a bacterial infection that affects at least a part of the subject's respiratory tract or a respiratory organ. In an aspect, the subject has been diagnosed with or is suspected of having a bacterial infection and a fungal infection that affect at least a part of the subject's respiratory tract or a respiratory organ. In an aspect, the subject has been diagnosed with or is suspected of having a fungal infection that affects at least one part of the subject's respiratory tract or a respiratory organ.

In an aspect, a disclosed method can comprise orally administering to the subject a pharmaceutical composition comprising one or more anti-infective agents. In an aspect, the additional anti-infective agent can be an antibacterial agent. Antibacterial agents are known to the art and discussed supra. In an aspect, the additional anti-infective agent can be an antifungal agent. Antifungal agents are known to the art and discussed supra.

In an aspect, mixing the compounded composition with the diluent can comprise adding about 1 g to about 30 g of the compounded composition to the diluent. In an aspect, mixing the compounded composition with the diluent can comprise adding about 1 g, or about 5 g, or about 10 g, or about 15 g, or about 20 g, or about 25 g, or about 30 g of the compounded composition to the diluent. In an aspect, mixing the compounded composition to the diluent can comprise adding about 10 g and about 20 g, about 15 g and about 30 g, about 20 g and about 30 g, or about 22 g and about 27 g of the compounded composition with the diluent.

In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL.

In an aspect, the diluent can comprise sodium hypochlorite. In an aspect, the diluent can comprise Dakin's solution. In an aspect, the amount of diluent can be about 20 mL to about 60 mL, or about 30 to about 50 mL, or about 20 mL, or about 30 mL, or about 40 mL, or about 50 mL, or about 60 mL.

In an aspect, a disclosed method can comprise repeating daily the administering step. In an aspect, a disclosed method can comprise repeating daily the administering step until the bacterial infection or suspected bacterial infection or the fungal infection or the suspected fungal infection is eradicated or appears to be eradicated.

In an aspect, a disclosed method can comprise repeating daily the mixing step or the administering step or repeating both steps. In an aspect, a disclosed method can comprise repeating daily the mixing step or the administering step or reporting both the steps until the bacterial infection, suspected bacterial infection, the fungal infection, or the suspected fungal infection is eradicated or appears to be eradicated.

In an aspect, a disclosed method can comprise repeating the mixing step or the administering step or both the mixing step and the administering step for a pre-determined amount of time. In an aspect, the pre-determined amount of time can comprise at least 5 days, at least 7 days, at least 10 days, at least 14 days, at least 21 days, at least 30 days, or more. In an aspect, the pre-determined amount can comprise an amount of time lasting at least 5-7 days, at least 7-10 days, at least 10-14 days, at least 14-21 days, at least 21-30 days, or at least 30 days.

In an aspect, intranasally administering can comprise delivering to the subject the solution or suspension via the subject's nares. In an aspect, delivering the solution or suspension to the nares can comprise using irrigation, or using a nasal spray, or using a metered inhaler, or using nebulization, or using particle dispersion. In an aspect, delivering the solution or suspension can comprise a sinus rinse, which can use positive pressure to clean or irrigate the nasal passages and maintain the head of the subject in an upright position. A sinus rinse delivery device known to the art is the NeilMed® device. The art is familiar with each of these techniques, the equipment required to effect each of these techniques, and the means to prepare the compounded composition for each technique of intranasal administration.

In an aspect, a small particle nebulization delivery system can be configured to nebulize the solution or suspension comprising a disclosed compounded composition to produce small particles or droplets. In an aspect, small particles or droplets can have aerosol characteristics, wherein the particle size of the majority (e.g., at least 50%, at least 60%, at least 70%, at least 80%, at least 90%, or more) of the particles or droplets formed by the nebulization can be less than about 10 microns, or less than about 8 microns, or less than about 5 microns, or less than about 3 microns. In an aspect, the particles or droplets can be about 3-about 10 microns, or about 3 microns-about 8 microns, or about 3 microns-about 5 microns, or about 5 microns-about 8 microns, or about 5 microns-about 10 microns, or about 8 microns-about 10 microns.

In an aspect, a large particle nebulization delivery system can be configured to nebulize the solution or suspension comprising a disclosed compounded composition to produce large particles or droplets. In an aspect, small particles or droplets can have aerosol characteristics, wherein the particle size of the majority (e.g., at least 50%, at least 60%, at least 70%, at least 80%, at least 90%, or more) of the particles or droplets formed by the nebulization can be more than about 10 microns, or more than about 15 microns, or more than about 20 microns, or more than about 25 microns. In an aspect, the particles or droplet can be about 10 microns-about 25 microns, or about 10 microns-about 20 microns, or about 10 microns-about 15 microns, or about 15 microns-about 25 microns, or about 15 microns-about 20 microns, or about 20 microns-about 25 microns.

In an aspect, a disclosed method can comprise cleaning the device.

In an aspect, a disclosed method can comprise preparing a compounded composition. Methods of preparing a disclosed compounded composition are discussed supra.

In an aspect, a disclosed method of treating or preventing an infection using an intranasally administered compounded composition can comprise modifying one or more aspect of the disclosed method. For example, in an aspect, a method can be modified by changing the amount of a disclosed compounded composition intranasally administered, by changing the frequency of the subject's use of intranasal administration, or by substituting one disclosed compounded composition for another disclosed compounded composition, or a combination thereof.

What is claimed is:

1. A method for treating one or both of a bacterial infection or fungal infection of a foot of a subject, the method comprising:
    providing a compounded ointment comprising mupirocin 2% ointment in an amount at least 60% w/w of the compounded ointment and an anti-infective for injection powder in an amount from about 1% to about 20% w/w of the compounded ointment, wherein the anti-infective for injection powder comprises one or more of bacitracin for injection, colistimethate sodium for injection, pentasodium colistin methanesulfonate for injection, piperacillin-tazobactam for injection, polymyxin B for injection, streptomycin sulfate for injection, voriconazole for injection, tobramycin sulfate for injection, or amphotericin B for injection; and
    providing a diluent for mixing with the compounded ointment to prepare a footbath solution for contacting a skin area of a foot of a subject that is infected or suspected to be infected.

2. The method of claim 1, wherein the anti-infective for injection comprises voriconazole for injection.

3. The method of claim 2, wherein the compounded ointment comprising mupirocin 2% ointment in an amount about 86% w/w of the compounded ointment and the voriconazole for injection in an amount about 0.8% w/w of the compounded ointment.

4. The method of claim 2, wherein the anti-infective for injection powder further comprises streptomycin sulfate for injection.

5. The method of claim 4, wherein the compounded ointment comprises mupirocin 2% ointment in an amount about 80% w/w of the compounded ointment, voriconazole for injection in an amount about 0.8% w/w of the compounded ointment, and streptomycin sulfate for injection in an amount about 5.528% w/w of the compounded ointment.

6. The method of claim 4, further comprising compounding the compounded ointment comprising combining crushed doxycycline hyclate tablet powder with the mupirocin 2% ointment and the anti-infective for injection powder.

7. The method of claim 4, wherein the compounded ointment comprises mupirocin 2% ointment in an amount about 77.6% w/w of the compounded ointment, voriconazole for injection in an amount about 0.8% w/w of the compounded ointment, streptomycin sulfate for injection in an amount about 5.528% w/w of the compounded ointment, and crushed doxycycline hyclate tablet powder in an amount sufficient to obtain about 1% w/w doxycycline in the compounded ointment.

8. The method of claim 1, wherein the anti-infective for injection powder comprises tobramycin for injection, and wherein the compounded ointment further comprises crushed doxycycline hyclate tablet powder compounded with the mupirocin 2% ointment and the anti-infective for injection powder.

9. The method of claim 8, wherein the compounded ointment comprises mupirocin 2% ointment in an amount about 81.3% w/w of the compounded ointment, voriconazole for injection in an amount about 0.8% w/w of the compounded ointment, tobramycin sulfate for injection in an amount about 1.8% w/w of the compounded ointment, and crushed doxycycline hyclate tablet powder in an amount sufficient to obtain about 1% w/w doxycycline in the compounded ointment.

10. The method of claim 1, wherein the anti-infective for injection powder comprises streptomycin sulfate for injection, and wherein the compounded ointment further comprises crushed doxycycline hyclate tablet powder and crushed ketoconazole tablet powder compounded with the mupirocin 2% ointment and the anti-infective for injection powder.

11. The method of claim 10, wherein the compound composition comprises mupirocin 2% ointment in an amount about 85.7% w/w of the compounded ointment, streptomycin sulfate for injection in an amount about 5.528% w/w of the compounded ointment, a sufficient amount of crushed doxycycline hyclate tablet powder to obtain about 2% w/w doxycycline in the compounded ointment, and crushed ketoconazole tablet powder in an amount sufficient to obtain about 2.5% w/w ketoconazole in the compounded ointment.

12. A homogeneous compounded ointment, the compounded ointment comprising:
    mupirocin 2% ointment in an amount at least 60% w/w, and
    an anti-infective for injection in an amount from about 1% to about 20% w/w, wherein the anti-infective for injection comprises one or more of bacitracin for injection, colistimethate sodium for injection, pentasodium colistin methanesulfonate for injection, piperacillin-tazobactam for injection, polymyxin B for injection, streptomycin sulfate for injection, voriconazole for injection, tobramycin sulfate for injection, or amphotericin B for injection.

13. The compounded ointment of claim 12, wherein the anti-infective for injection comprises voriconazole for injection, and wherein the compounded ointment comprises about 86% w/w mupirocin 2% ointment and about 0.8% w/w voriconazole for injection.

14. The compounded ointment of claim 12, wherein the anti-infective for injection comprises voriconazole for injection and streptomycin sulfate for injection, and wherein the compounded ointment comprises about 80% w/w mupirocin 2% ointment, about 0.8% w/w voriconazole for injection, and about 5.528% w/w streptomycin sulfate for injection.

15. The compounded ointment of claim 12, wherein the anti-infective for injection comprises voriconazole for injection and streptomycin sulfate for injection, wherein the compounded ointment further comprises about 1% w/w doxycycline, and wherein the compounded ointment comprises about 77.6% w/w mupirocin 2% ointment, about 0.8% w/w voriconazole for injection, about 5.528% w/w streptomycin sulfate for injection, and about 2.435% w/w doxycycline hyclate 100 mg tablet.

16. The compounded ointment of claim 12, wherein the anti-infective for injection comprises voriconazole for injection and tobramycin sulfate for injection, wherein the compounded ointment further comprises about 1% w/w doxycycline, and wherein the compounded ointment comprises about 81.3% w/w mupirocin 2% ointment, about 0.8% w/w voriconazole for injection, about 1.8% w/w tobramycin sulfate for injection, and about 2.435% w/w doxycycline hyclate 100 mg tablet.

17. The compounded ointment of claim 12, wherein the anti-infective for injection comprises streptomycin sulfate for injection, wherein the compounded ointment further comprises about 2% doxycycline and about 2.5% ketoconazole, and wherein the compounded ointment comprises about 85.7% w/w mupirocin 2% ointment, about 5.528% w/w streptomycin sulfate for injection, about 4.87% w/w doxycycline hyclate 100 mg tablet, and about 3.875% ketoconazole 200 mg tablet.

* * * * *